US012678440B2

(12) United States Patent
Chen et al.

(10) Patent No.: US 12,678,440 B2
(45) Date of Patent: Jul. 14, 2026

(54) COMPOSITIONS AND METHODS FOR TREATING MISFOLDED PROTEIN OCULAR DISORDERS

(71) Applicants: CASE WESTERN RESERVE UNIVERSITY, Cleveland, OH (US); UNIVERSITY OF PITTSBURGH—OF THE COMMONWEALTH SYSTEM OF HIGHER EDUCATION, Pittsburgh, PA (US)

(72) Inventors: Yuanyuan Chen, Pittsburgh, PA (US); Krzysztof Palczewski, Cleveland, OH (US)

(73) Assignees: CASE WESTERN RESERVE UNIVERSITY, Cleveland, OH (US); UNIVERSITY OF PITTSBURGH OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 819 days.

(21) Appl. No.: 17/802,325

(22) PCT Filed: Feb. 26, 2021

(86) PCT No.: PCT/US2021/019813
§ 371 (c)(1),
(2) Date: Aug. 25, 2022

(87) PCT Pub. No.: WO2021/173929
PCT Pub. Date: Sep. 2, 2021

(65) Prior Publication Data

US 2024/0374599 A1 Nov. 14, 2024

Related U.S. Application Data

(60) Provisional application No. 62/981,819, filed on Feb. 26, 2020.

(51) Int. Cl.

| | |
|---|---|
| ***A61K 31/519*** | (2006.01) |
| ***A61K 31/4545*** | (2006.01) |
| ***A61K 31/5025*** | (2006.01) |
| ***A61K 31/506*** | (2006.01) |
| ***A61P 27/02*** | (2006.01) |

(52) U.S. Cl.
CPC ........ *A61K 31/519* (2013.01); *A61K 31/4545* (2013.01); *A61K 31/5025* (2013.01); *A61K 31/506* (2013.01); *A61P 27/02* (2018.01)

(58) Field of Classification Search
CPC .............. A61K 31/519; A61K 31/4545; A61K 31/5025; A61K 31/506; A61K 31/454; A61K 31/444; A61P 27/02
See application file for complete search history.

(56) References Cited

U.S. PATENT DOCUMENTS

| | | | |
|---|---|---|---|
| 7,166,570 | B2 | 1/2007 | Hunter et al. |
| 2010/0087474 | A1 | 4/2010 | Kaushal et al. |

FOREIGN PATENT DOCUMENTS

| | | | |
|---|---|---|---|
| WO | 2013/163758 | A1 | 11/2013 |
| WO | 2018201146 | A1 | 11/2018 |
| WO | 2019169306 | A1 | 9/2019 |

OTHER PUBLICATIONS

Pasqualetto, Gaia et al. "Computational Studies towards the Identification of Novel Rhodopsin-Binding Compounds as Chemical Chaperones for Misfolded Opsins." Molecules (Basel, Switzerland) vol. 25,21 4904. Oct. 23, 2020, doi: 10.3390/molecules25214904 (Year: 2020).*

European Application No. 27159866.3, Search Report dated Jan. 29, 2024.

Surguchev A et al: "Conformational diseases: Looking into the eyes", Brain Research Bulletin, Elsevier Science Ltd, Oxford, GB, vol. 81, No. 1, Jan. 15, 2010 Jan. 15, 2010), pp. 12-24.

Yuanyuan Chen et al: "A novel small molecule chaperone of rod opsin and its potential therapy for retinal degeneration", Nature Communications, vol. 9, No. 1, May 17, 2018 (May 17, 2018).

Lin Jonathan H. et al.: "Misfolded Proteins and Retinal Dystrophies" In: "Retinal Degenerative Diseases", Dec. 28, 2009 (Dec. 28, 2009), Springer New York, New York, NY.

Rodgers Jessica et al: "Defining the impact of melanopsin missense polymorphisms using in vivo functional rescue", Human Molecular Genetics, vol. 27, No. 15, Apr. 30, 2018 (Apr. 30, 2018), pp. 2589-2603.

European Application No. 21759866.3, Extended Search Report dated Jul. 29, 2024.

Ghasemi Falavarjani Ket al: "Intra-silicone oil injection of methotrexate at the end of vitrectomy for advanced proliferative diabetic retinopathy", EYE, [Online] vol. 29, No. 9, Jul. 10, 2015 (Jul. 10, 2015), pp. 1199-1203.

Hardwig Paul W et al: "Intraocular Methotrexate in Ocular Diseases Other Than Primary Central Nervous System Lymphoma", American Journal of Ophthalmology, vol. 142, No. 5, Oct. 20, 2006 (Oct. 20, 2006), pp. 883-885.

Mashima Asako et al: "Successful Treatment of Necrotizing Retinitis with Epstein-Barr Virus-Positive Ocular Fluid by Intravitreal Methotrexate Injection", Ocular Immunology and Inflammation, [Online] vol. 28, No. 4, Jul. 3, 2019 (Jul. 3, 2019), pp. 552-555.

Khatua Deb Kumar et al: "Distinctively complete inhibition of fibrillation of serum albumins by methotrexate in vitro experimental and modelling studies to understand the tuning of protein misfolding-related aggregations", New Journal of Chemistry, [Online] vol. 43, No. 48, Nov. 18, 2019 (Nov. 18, 2019), pp. 18983-18987.

(Continued)

*Primary Examiner* — Tracy Vivlemore
(74) *Attorney, Agent, or Firm* — Tarolli, Sundheim, Covell & Tummino LLP

(57) ABSTRACT

A method of treating an inherited ocular disorder associated with or caused by a misfolded ocular protein in a subject in need thereof includes administering to the subject a compound that promotes clearance of misfolded ocular protein.

20 Claims, 24 Drawing Sheets

Specification includes a Sequence Listing.

(56) References Cited

OTHER PUBLICATIONS

Luibl Volker et al: "Drusen deposits associated with aging and age-related macular degeneration contain nonfibrillar amyloid oligomers", The Journal of Clinical Investigation, Bm J Group, [Online] vol. 116, No. 2, Feb. 1, 2006 (Feb. 1, 2006), pp. 378-385.
Sundstrom Jeffrey M. et al: "Proteomic Analysis of Early Diabetic Retinopathy Reveals Mediators of Neurodegenerative Brain Diseases", Investigative Opthalmology & Visual Science, [Online] vol. 59, No. 6, May 4, 2018 (May 4, 2018), p. 2264.
Applicant: Case Western Reserve University; "Compositions and Methods for Treating Misfolded Protein Ocular Disorders"; International Application No. PCT/US2021/019813 Filed Feb. 26, 2021; PCT International Search Report Authorized Officer Blaine r. Copenheaver dated May 13, 2021; 3 pgs.
Liu, et al.; "Pharmacological Clearane of Misfolded Rhodopsin for the Treatment of RHO-associated Retinitis Pigmentosa"; the FASEB Journal, 2020, pp. 10146-10167.
European Application No. 21759866.3, Office Action dated Aug. 4, 2025.
Australian Application No. 2021225926, Examination Report dated Dec. 24, 2025.

* cited by examiner

A

Hek293(RHO$^{P23H}$-Rluc)

Hek293(RHO$^{WT}$-Rluc)

B

Life Chemicals (50,560)

UC
(10,011)

MIPE    FDA    LOPAC    Spectrum
(1,912) (2,816) (1,280)    (2,400)

C

■ RHO$^{P23H}$-Rluc
RHO$^{WT}$-Rluc

Rluc Activity (%)

EC$_{50}$: 0.43 μM

Log$_{10}$[CL-009] (M)

H

CL-001
(2.1 µM)

CL-002
(1.6 µM)

CL-003
(0.59 µM)

CL-004
(0.47 µM)

CL-005
(1.3 µM)

CL-006
(1.7 µM)

CL-007
(2.9 µM)

CL-008
(1.6 µM)

CL-009
(3.3 µM)

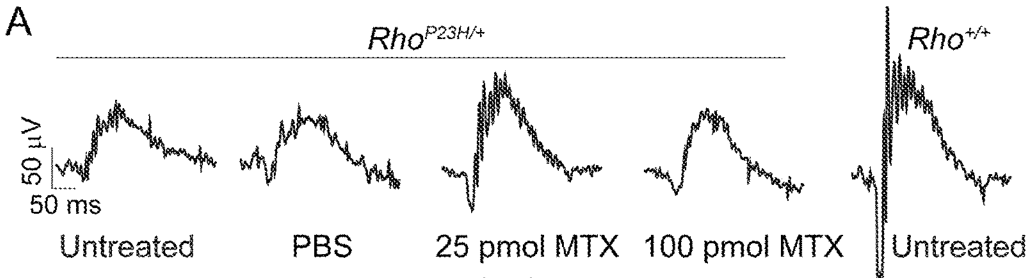
Fig. 6A
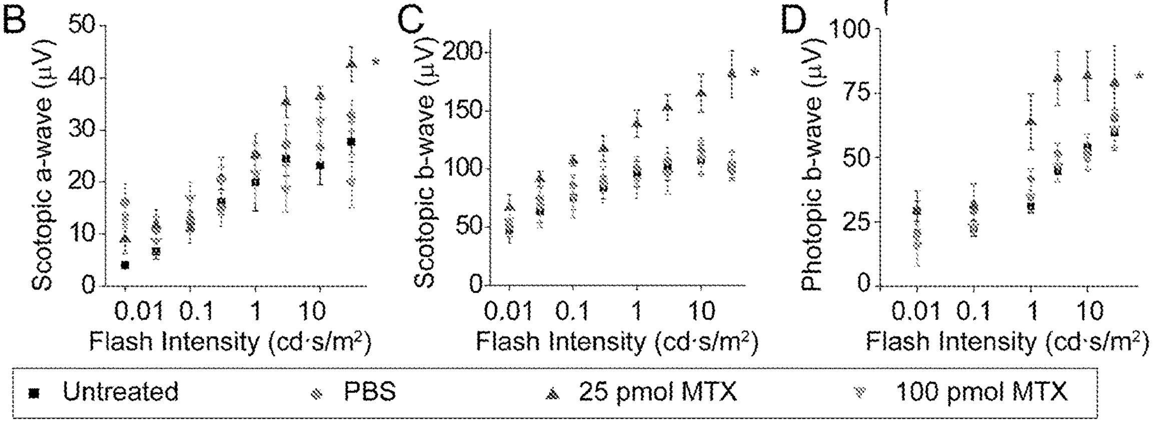
Fig. 6B
Fig. 6C
Fig. 6D
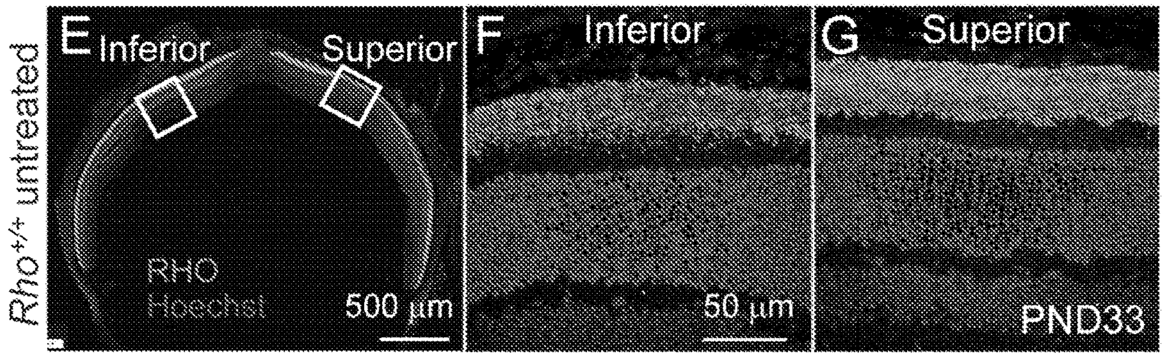
Fig. 6E
Fig. 6F
Fig. 6G
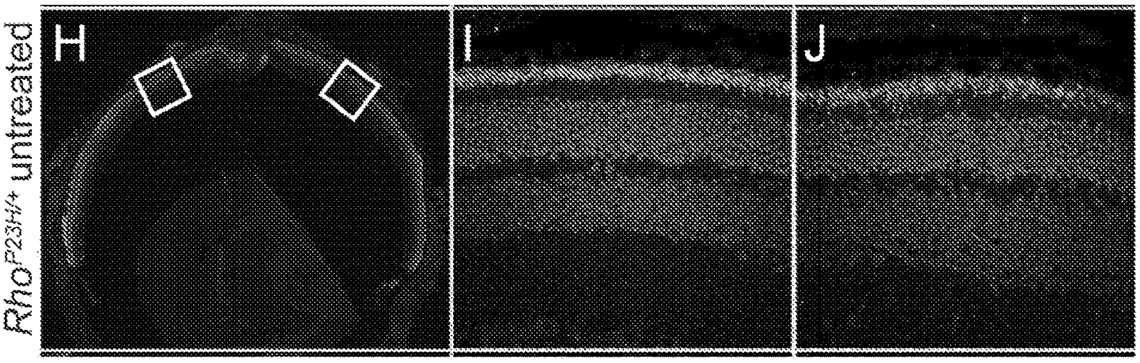
Fig. 6H
Fig. 6I
Fig. 6J

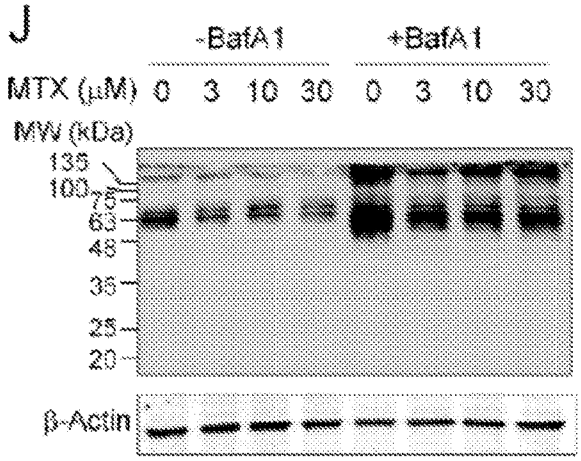
Fig. 12J
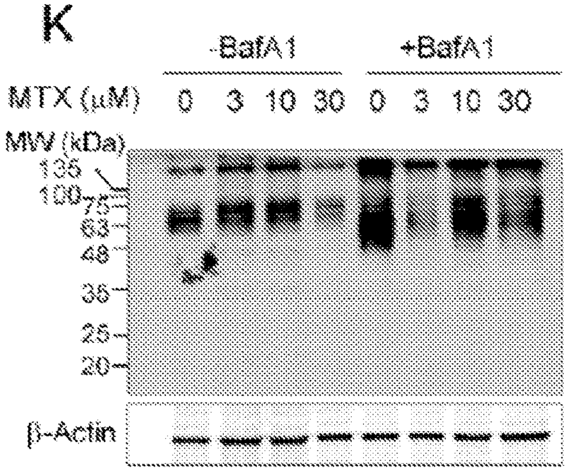
Fig. 12K
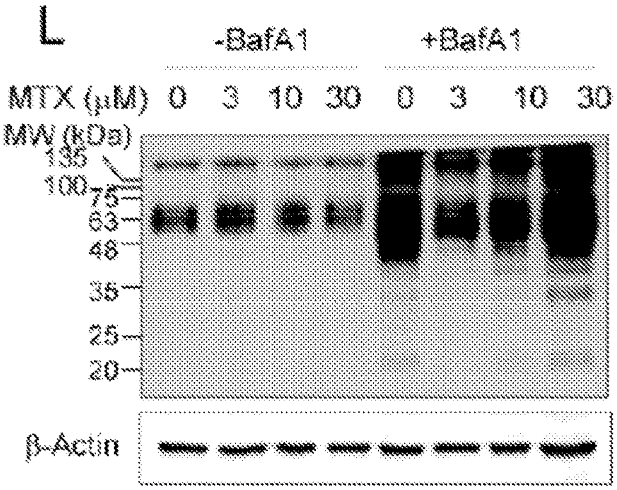
Fig. 12L
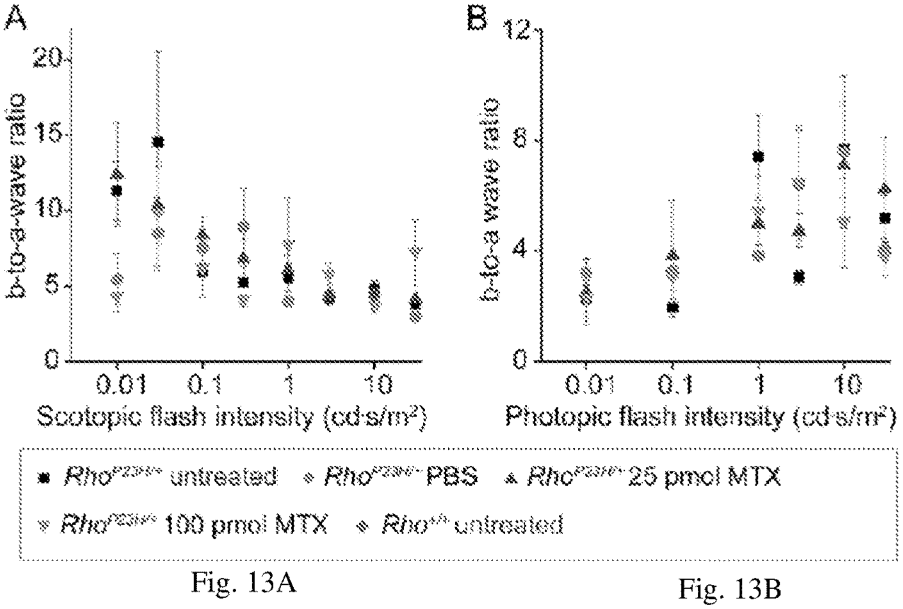
Fig. 13A
Fig. 13B

COMPOSITIONS AND METHODS FOR TREATING MISFOLDED PROTEIN OCULAR DISORDERS

RELATED APPLICATION

This application claims priority from U.S. Provisional Application No. 62/981,819, Filed Feb. 26, 2020, the subject matter of which is incorporated herein by reference in its entirety.

GOVERNMENT FUNDING

This invention was made with government support under EY024992 awarded by the National Institutes of Health. The government has certain rights in the invention.

SEQUENCE LISTING

The instant application contains a Sequence Listing which has been submitted electronically in .TXT format and is hereby incorporated by reference in its entirety. Said TXT copy was created on Aug. 14, 2023, is named CWR029201USPCT.st.25 and is 1,485 bytes in size.

BACKGROUND

Protein misfolding and unfolded protein response are found to contribute to inherited retinal diseases, such as retinitis pigmentosa (RP), a progressive retinal degeneration affecting more than one million people worldwide. The disease progression of RP varies widely but can last for decades. The gradual loss of rod photoreceptor cells causes night blindness followed by reduced visual field and finally tunnel vision. The central vision of many RP patients can last for many years until the secondary loss of cone photoreceptors when legal blindness occurs. More than 160 mutations in the RHO gene have been associated with RP, and about ⅓ of these mutations are believed to cause rhodopsin misfolding leading to a dominant-negative effect that is toxic to the rod photoreceptor cells. The RHO P23H mutation alone accounts for about 10-12% of all autosomal dominant (ad) RP cases in North America, and thus this mutation has been most commonly studied as a model of adRP. Like other protein misfolding diseases, no effective treatment is currently available for RP.

The dim-light receptor rhodopsin is the most abundant protein residing in the outer segments of rod photoreceptor cells and supports high visual sensitivity at night. Rhodopsin homeostasis is essential to maintain the rod outer segments (OS) morphology and rod photoreceptor function. Due to its high abundance and a 10% daily renewal rate of rod OS, rhodopsin biosynthesis is maintained at an extremely high level to keep rod OS length being constant. Thus, even one allele of RHO gene mutation can substantially disturb rhodopsin protein homeostasis, leading to rod cell death in RP. The P23H mutation affects the structural stability of the anti-parallel β-plug scaffold sitting on top of the retinal-binding site of rhodopsin, and this β-plug scaffold is essential for secluding the hydrophobic ligand-binding pocket from the aqueous environment. The mutant rhodopsin protein accumulates in the endoplasmic reticulum (ER) in cultured cells. The ER-associated protein degradation pathway is activated in the $Rho^{P23H/+}$ knock-in mouse retina, and more than 90% of the mutant rhodopsin protein undergoes degradation, supporting the notion that the protein quality control system is working hard to maintain rhodopsin homeostasis. Nonetheless, this robust proteolytic system in the rods of the $Rho^{P23H/+}$ mouse retina is in the long-term overwhelmed by the constant and high load of rhodopsin degradation.

To prevent the misfolded rhodopsin-caused rod death in early- or mid-stage adRP, experimental efforts have been focused on supporting rhodopsin folding or boosting the ER associated protein degradation system. For example, pharmacological or chemical chaperones were reported to improve rhodopsin folding and its cellular transport, including the vitamin A derivatives and analogues, 4-phenylbutyate and curcumin. High-dose vitamin A supplementation has shown some level of visual protection among RP patients. However, due to the lack of genetic information of these patients, it is not clear whether the efficacy of vitamin A is due to an increased retinal supply of 11-cis-retinal as a pharmacological chaperone of rhodopsin.

Reducing the misfolded rhodopsin has been shown as an effective strategy to rescue rod photoreceptors. Long-term retinal protection has been shown in P23H transgenic rats that were treated by gene delivery of a small ribozyme that specifically cut the mutant allele of rhodopsin mRNA. Enhancing misfolded rhodopsin degradation by transgenic overexpression of a regulatory subunit of proteasome has also showed retinal protection in the rhodopsin P23H knock-in mice. These studies suggest clearing the misfolded rhodopsin is sufficient to preserve rod photoreceptors in RHO-associate adRP. However, no effective pharmacological tools are available to clear the misfolded rhodopsin and show retinal protection in vivo.

SUMMARY

Embodiments described herein relate to compounds and methods of treating an inherited ocular disorder associated with or caused by misfolded ocular proteins in a subject in need thereof. It was found that reducing misfolded ocular proteins, such as misfolded opsin proteins, can be an effective strategy to preserve or rescue rod photoreceptors in subjects with inherited ocular disorders associated with or caused by the misfolded ocular protein. Using a small molecule high-throughput screening assay, compounds were identified that selectively reduced misfolded mutant ocular proteins without an effect on corresponding wild type proteins. The compounds were found to promote clearance or accelerate degradation of misfolded ocular proteins, preserve visual function, and prevent photoreceptor death related to the inherited ocular disorder.

Accordingly, in some embodiments methods of promoting clearance of misfolded ocular proteins and/or treating an inherited ocular disorder associated with or caused by a misfolded ocular protein in a subject in need thereof include administering to the subject a therapeutically effective amount of a compound selected from:

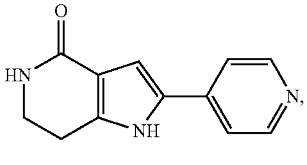,

-continued

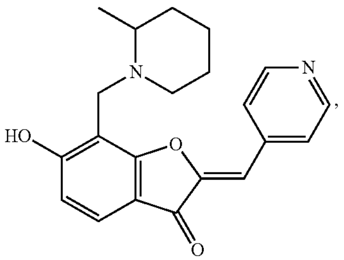

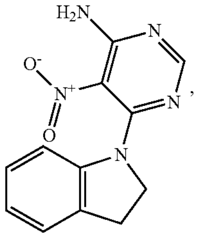

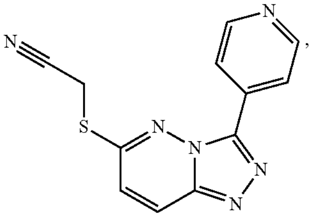

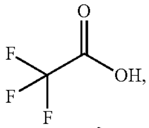

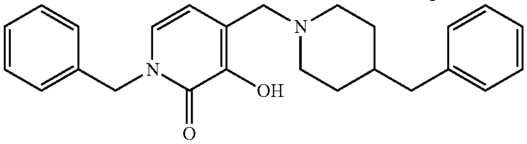

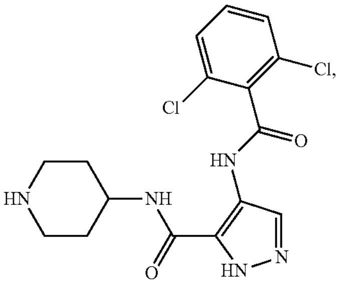

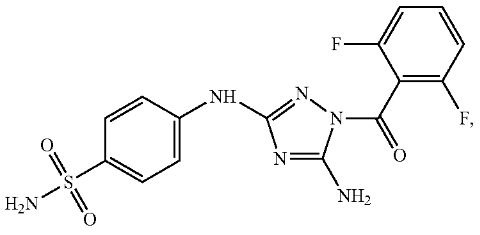

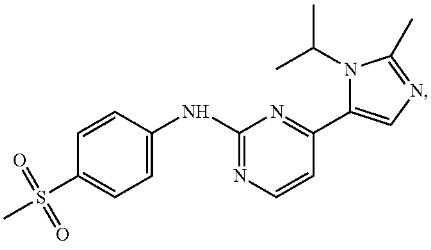

-continued

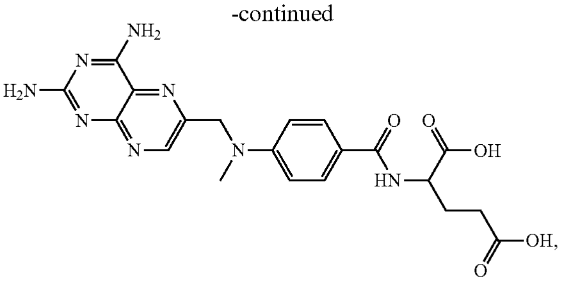

a pharmaceutically acceptable salt, tautomer, or solvate thereof, or combinations thereof.

In other embodiments, the compound can be selected from:

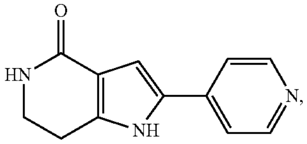

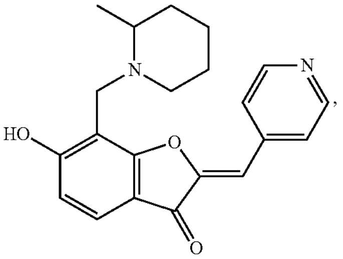

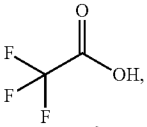

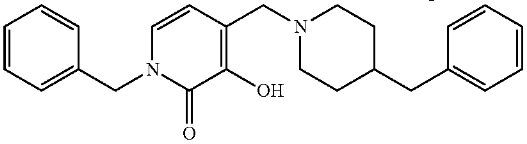

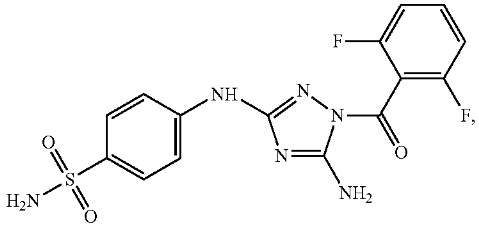

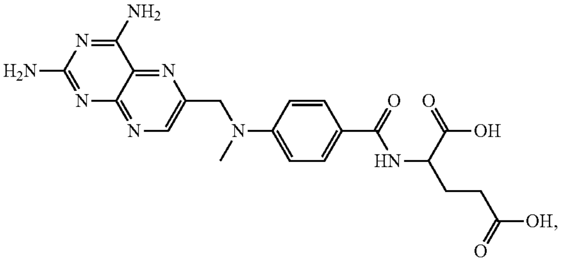

a pharmaceutically acceptable salt, tautomer, or solvate thereof, or combinations thereof.

In some embodiments, the subject is predisposed to or has an inherited ocular disorder associated with or caused by the misfolded ocular protein. For example, the subject can be predisposed to or have a non syndromic retinal disorder associated with or caused by the misfolded ocular protein, such as non syndromic autosomal dominant retinitis pigmentosa associated with or caused by misfolded opsin protein.

In some embodiments, the misfolded ocular protein is a misfolded opsin. The misfolded opsin protein that can include a mutation in its amino acid sequence. For example, the misfolded mutant opsin protein can be misfolded mutant rhodopsin, wherein the mutation is at least one of P23H, C110Y, D190N, T17M, P347S, or P267L.

In some embodiments, the compound can be administered by at least one of topical administration, systemic administration, intravitreal injection, and intraocular delivery. Advantageous, the compound is administered to the subject at an early or mid-stage of the ocular disorder, such as early stage or mid stage of the non syndromic autosomal dominant retinitis pigmentosa, to arrest development or progression retinal degeneration.

In some embodiments, a therapeutically effective amount of the compound administered to the subject is an amount effective to accelerate the degradation of the misfolded ocular protein, improve ocular protein homeostasis, improve or preserve visual function, inhibit photoreceptor cell death, and/or improve or preserve retinal structure.

In some embodiments, the improvement or preservation in visual function includes an improvement or preservation of photopic electroretinogram (ERG) response. In other embodiments, the improvement or preservation in retinal structure is an improvement or preservation of outer nuclear layer (ONL) thickness.

FIGS. 4(A-G) illustrate plots and images showing Methotrexate (MTX/CL-009) mediated P23H rhodopsin degradation via lysosomal activity in vitro. A. Immunoblot of rhodopsin in NIH3T3 ($RHO^{P23H}$/GFP) and NIH3T3 ($RHO^{WT}$/GFP) cells co-treated with (+) or without (−) 10 μM MTX, 100 nM bafilomycin A1 (BafA1) or 5 μM MG-132 for 24 h. β-Actin was the loading control. B. Immunoblots in A were repeated and quantified as a percentage of relative RHO level by ImageJ. The middle lines and error bars are means and SDs. *, $p<0.05$ by an unpaired two-tail Student's t-test. $RHO^{P23H}$, black squares; and $RHO^{WT}$, magenta circles. C. High content images of rhodopsin immunostaining in NIH3T3 ($RHO^{P23H}$/GFP) (top) and NIH3T3 ($RHO^{WT}$/GFP) (bottom) cells treated with DMSO, 10 μM MTX, 10 μM MTX plus 100 nM BafA1, or 10 μM MTX plus 5 μM MG-132 Scale bar, 50 μm. D. Relative immunostaining intensity (INT) of P23H rhodopsin measured from high-content images of NIH3T3 ($RHO^{P23H}$/GFP) cells plotted as a function of MTX concentration alone or in co-treatment with 100 nM BafA1 or 5 μM MG-132. Immunostaining intensity of P23H rhodopsin per cell was normalized by DMSO treated cells as 0% and cells stained with secondary antibody only as −100%, respectively. Data points and error bars are means and SDs. N=3. E-G. Effect of MTX on chymotrypsin-like proteasome activity in the NIH3T3 ($RHO^{P23H}$/GFP) and NIH3T3 ($RHO^{WT}$/GFP) cells. E. The luminescence readouts of proteasome activities as a function of cell number showing the cell number we used in B is within the sensitive range of the assay. F. The luminescence readouts of NIH3T3 (grey), NIH3T3 ($RHO^{WT}$/GFP) (magenta) and NIH3T3 ($RHO^{P23H}$/GFP) (dark grey) cells treated with 0.1% DMSO or 5 μM MG-132 as the 100% and 0% controls, respectively. Means and SDs from 8 biological replicates (shown as diamonds) are shown as middle bars and error bars. The $Z'=1-3\times(SD_{100\%\ control}+SD_{0\%\ control})/(Mean_{100\%\ control}-Mean_{0\%\ control})$ is in the inset demonstrating the assay being robust. G. Normalized chymotrypsin-like proteasome activity of cells in response to 10 doses of MTX. Chymotrypsin-like proteasome activity was normalized by the 100% and 0% controls, respectively. Data points and error bars are the means and SDs of three biological replicates.

Figure 5A:
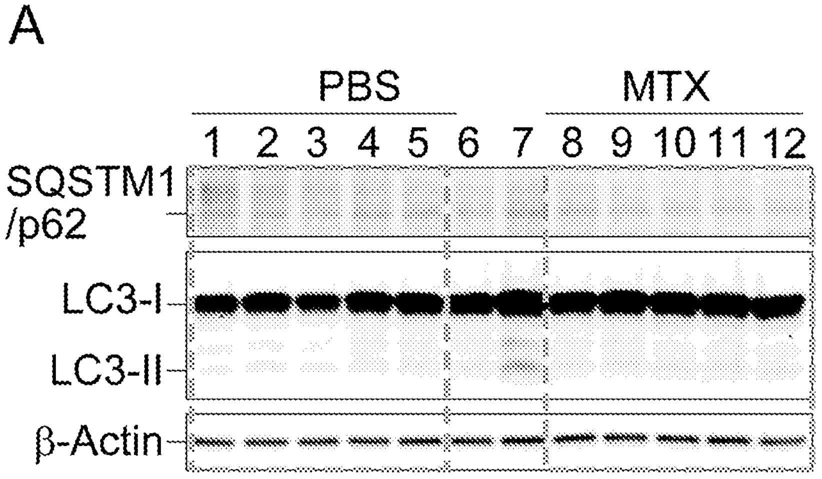

FIGS. 5(A-C) illustrate immunoblots and plots showing MTX increased autophagy flux in the retinae of $Rho^{P23H/+}$ mice. A. Immunoblots of SQSTM1/p62 and LC3 in 30 μg of retina lysates from $Rho^{P23H/+}$ mice at 48 h after an intravitreal injection (IVI) of 25 pmol/eye MTX or phosphate-buffered saline (PBS) at PND 15. β-Actin was the loading control. Dashed boxes are samples selected for intensity analysis in B and C, excluding lanes 6 and 7 in which samples may be mixed up when loaded. B and C. Ratios of band intensities of SQSTM1/p62 to β-actin, and LC3-II to β-actin measured from immunoblotting images in A, respectively. Left, retinae treated with PBS; right, retinae treated with 25 pmol MTX per eye. Middle lines and error bars are means and SDs. N=5. *, $p<0.05$ between MTX treated and PBS groups calculated by an unpaired two-tail Student's t-test.

FIGS. 6(A-R) illustrate plots and images showing one intravitreal injection (IVI) of MTX increased electroretinogram (ERG) response and retinal rhodopsin level in $Rho^{P23H/+}$ mice. Eyes of mice were untreated or intravitreally injected with PBS, 25 or 100 pmol MTX at PND 15, and ERG responses were recorded at PND 32. Mice were euthanized and eyes were enucleated at PND 33 for immunohistochemistry (IHC). Age-matched $Rho^{+/+}$ mice were used as the normal control. A. Scotopic ERG recordings stimulated by a flash of light at 10 $cd\cdot s/m^2$. B and C. Eight-flash scotopic a- and b-wave amplitudes of treated mice plotted as a function of flash intensity (semi-log format), respectively. D. Six-flash photopic b-wave amplitudes plotted as a function of flash intensity (semi-log format). Black squares, red circles, blue triangles, and magenta reverse triangles were from $RHO^{P23H/+}$ mice that were untreated, PBS, 25 and 100 pmol MTX treated, respectively. Data points and error bars are means and SEMs, respectively. N=5. *, $p<0.05$ between 25 pmol MTX and PBS treated groups calculated by a two-way ANOVA. Factor 1, treatment; and factor 2, flash intensity. Scale bar, 50 μm. Q. Spidergram of rhodopsin immunofluorescence E-P. IHC images of untreated $Rho^{+/+}$ retina, and $Rho^{P23H/+}$ mouse retinae that are untreated, PBS-treated, or 25 pmol MTX-treated, from top to bottom, respectively. RHO and nucleus (Hoechst 33342) were stained in red and blue, respectively. E, H, K and N are retinal IHC images at low magnification. Scale bar, 500 μm. F, I, L and O are high magnification retinal images taken at sites marked in boxes shown in E, H, K and N on the retinal inferior side, and G, J, M and P are images on the superior side, respectively intensity in the OS measured by ImageJ from high magnification images taken at 0.6, 1 and 1.4 mm from the optic nerve head (ONH). Green squares, age-matched $Rho^{+/+}$ mouse retinae. R. Spidergram of outer nuclear layer (ONL) nucleus number per 200 μm length of retina cross-section images taken at 0.6, 1, and 1.4 mm distance from ONH. Data points and error bars are means and SEMs, respectively. N=3. *, $p<0.05$ between 25 pmol MTX and PBS groups by an unpaired two-tail Student's t-test.

FIGS. 7(A-O) illustrate plots and images showing multiple IVIs of MTX improved ERG response, rhodopsin level and preserved photoreceptor cell numbers of the $Rho^{P23H/+}$ mouse retinae. Eyes of $Rho^{P23H/+}$ mice were untreated or administered by four weekly IVIs of PBS, 25 pmol MTX and 100 pmol MTX per treatment, starting at PND 15 and ERGs were taken at PND 44. Eyes were enucleated at PND 46 for IHC. A. Scotopic ERG responses stimulated by a flash of light at 10 $cd\cdot s/m^2$. B and C. Eight-flash scotopic a- and b-wave amplitudes of treated mice plotted as a function of flash intensity (semi-log format), respectively. D. Six-flash photopic b-wave amplitudes plotted as a function of flash intensity. Black squares, red circles, blue triangles, and magenta reverse triangles are from $RHO^{P23H/+}$ mice that were untreated, PBS, 25 and 100 pmol MTX treated, respectively. Data points and error bars are means and SEMs, respectively. N=5. *, $p<0.05$ between 25 pmol MTX and PBS treated groups calculated by a two-way ANOVA. Factor 1, treatment; and factor 2, flash intensity. E-M. IHC images of untreated, PBS-treated, and 25 pmol MTX treated $Rho^{P23H/+}$ mouse retinae, from top to bottom, respectively. RHO and nucleus (Hoechst 33342) were stained in red and blue, respectively. E, H, and K are retinal images at lower magnification. Scale bar, 500 μm. F, I, and L are high magnification retinal images taken at sites marked as boxes shown in E, H, and K on the inferior side, and in G, J, and M are images on the superior side, respectively. Scale bar, 50 μm. N. Spidergram of rhodopsin immunofluorescence intensity in the OS measured by ImageJ from high magnification immunofluorescence images taken at 0.6, 1 and 1.4 mm from ONH. O. Spidergram of ONL nucleus number per 200 μm length of retina cross-section images taken at 0.6, 1, and 1.4 mm from ONH. Data points and error bars are means and SEMs, respectively. N=3. *, $p<0.05$ between 25 pmol MTX and PBS groups by an unpaired two-tail Student's t-test.

FIGS. 8(A-E) illustrate Immunoblots confirmed rhodopsin expression in stable cells used for HTS and confirmation assays. A. The immunoblots of rhodopsin showing the Hek293 ($RHO^{P23H}$-Rluc) and Hek293 ($RHO^{WT}$-Rluc) cells expressed the equivalent amount of P23H or WT rhodopsin-Rluc fusion proteins. β-Actin was used as loading control. B-E. Immunoblots of rhodopsin in U2OS stable cell single clones expressing WT, T4R, P23H, P53R, C110Y and P267L mouse rhodopsin each fused with Venus fluorescence protein on the C-terminus. Clones that were selected for the high-content imaging analyses under the treatment of hit compounds (shown in FIG. 3) were marked by red boxes. Difference in molecular masses between WT and mutant RHOs are due to immature glycosylation of RHO mutants that are accumulated in the endoplasmic reticulum.

FIGS. 9(A-H) illustrate Rhodopsin dot blots of NIH3T3 ($Rho^{P23H}$/GFP) (A, C, E and G) and NIH3T3 ($Rho^{WT}$/GFP) cells (B, D, F and H) each treated with different compounds including CL-001 to CL-009 at 10 or 20 μM for 24 h. A-F. Three biological repeats from cells treated with CL-002, CL-003, CL-004, CL-005 and CL-009. G-H. Four biological repeats of dot blots from cells treated with CL001, CL-006, CL-007 and CL-008 are shown in the bottom four scans. Dot blots shown in FIGS. 1D&F were cropped from these original scans. Rhodopsin dot blot intensities in these repeats were measured and plotted in the curves and box chart shown in FIGS. 1E&G.

FIGS. 10(A-F) illustrate immunoblots and plots showing the effect of nine hits on rhodopsin degradation in the NIH3T3 ($RHO^{P23H}$/GFP) cells using the non-radioactive pulse-chase assay. A. Dot blot of RHO at different steps of RHO immunoprecipitation (IP) from NIH3T3 ($RHO^{WT}$/GFP) cells suggesting a high yield of rhodopsin pulldown. Dot blots from 5% of total cell lysate, 5% of flow-through, last wash through, first and second elution, were marked as T, FT, W, E1, and E2, from left to right, respectively. B. Chase of WT and P23H rhodopsin at 0, 4, and 24 h after the pulse with AHA, IP by anti-rhodopsin antibody (RHO) and immunoblotted (IB) by streptavidin (SA). Met, lysates of cells always incubated with Met as the blank control. C. Percentage of nascent rhodopsin decayed as a function of chase time, quantified from B by ImageJ. Grey squares, P23H rhodopsin; magenta circles, WT rhodopsin. D. NIH3T3 ($RHO^{P23H}$/GFP) cells were treated with 10 μM of CL-001 to CL-009, or DMSO at 0 h of chase time, respectively. Nascent P23H rhodopsin from cell lysates IP with RHO and IB with SA at 24 h of chase time. E. Total P23H rhodopsin from the same batch of cell lysate IP with RHO and IB with RHO confirming the activity of each hit compound indeed reduced the total P23H rhodopsin protein level. Dot blot intensities in D were quantified and shown in FIG. 3C. F. Dot intensities quantified from dot blot scans in E and normalized by the DMSO control. Squares and error bars are the means and SDs of six biological replicates, and boxes showed the 75, 50 and 25% of data values.

FIGS. 11(A-E) illustrates plots and an immunoblot showing rhodopsin immunofluorescence intensities measured from high-content immunostaining images of U2OS cells stably expressing the WT or six mutants of rhodopsin that cause autosomal dominant retinitis pigmentosa, under treatment with CL-001 (A), CL-002 (B), CL-005 (C), CL-007 (D), and CL-009 (E). Normalized rhodopsin intensities were plotted as a function of seven doses of each compound in semi-log format. Dose-response curves were fitted by the Origin Software using the modified Hill function. Data points and error bars were means and SD from three biological replicates. The range of $EC_{50}$s of each compound towards different rhodopsin mutants were shown at the bottom of each graph. Data from cells expressing WT, T4R, P23H, P53R, C110Y, D190N, and P267L rhodopsin are marked as black squares, red circles, green triangles, blue reverse triangles, cyan diamonds, magenta left-pointed triangles and olive right-pointed triangles, respectively.

Figure 4A:
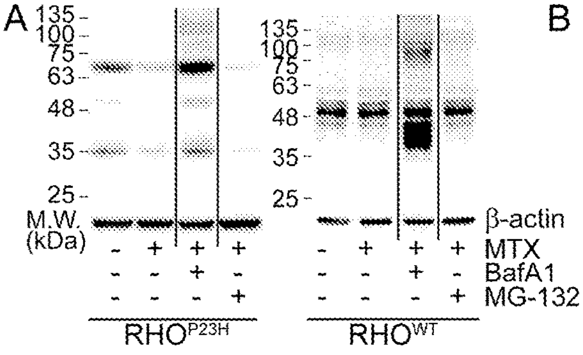
Figure 4B:
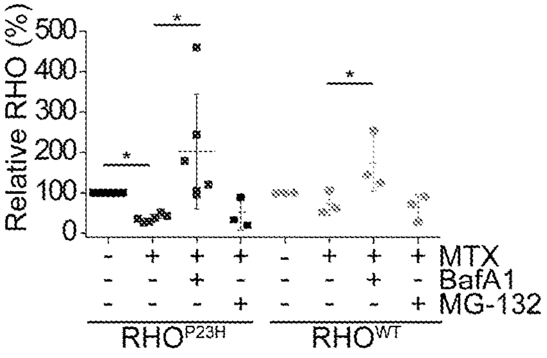

FIGS. 12(A-L) illustrate immunoblots showing the effect of inhibiting proteasomal or lysosomal activities on MTX's effect of rhodopsin degradation. Left (A, B, C) and right (G, H and I) are immunoblots of rhodopsin from lysates of NIH3T3 ($RHO^{P23H}$/GFP) and NIH3T3 ($RHO^{WT}$/GFP) cells treated with DMSO, 10 μM methotrexate (MTX), 35.5 μM cycloheximide (CHX), 35.5 μM CHX and 10 μM MTX, 100 nM Bafilomycin A1 (BafA1), 100 nm BafA1 and 10 μM MTX, 5 μM MG-132, 5 μM MG-132 and 10 μM MTX, 100 nM BafA1 and 5 μM MG-132, respectively. D, E and F are from NIH3T3 ($RHO^{P23H}$/GFP) cells treated with 0, 3, 10, 30 μM of MTX, with or without co-treatment of 100 nM BafA1. J, K and L are from NIH3T3 ($RHO^{P23H}$/GFP) cells treated with 0, 3, 10, 30 μM of MTX, with or without co-treatment of 100 nM BafA1. FIG. 4A was cropped from the immunoblot scans of A and B here, and quantification shown in FIG. 4B was calculated from the three biological repeats shown here in A-L.

FIGS. 13(A-F) illustrate plots showing MTX treatment improved retinal function and rhodopsin homeostasis in $Rho^{P23H/+}$ knock-in mice. A single IVI of MTX did not affect the b-to-a-wave ratio in vivo. $Rho^{P23H/+}$ knock in mice were intravitreally injected with PBS, 25 or 100 pmol of MTX at PND 15, and ERGs were recorded at PND32 and shown in FIGS. 6A-D. A and B are scotopic and photopic b-to a-wave ratios plotted as a function of flash intensity in a semi-log format, respectively. Data and error bars are means and SEMs, respectively. N=5. $P1>0.05$ by a two-way ANOVA suggests neither 25 nor 100 pmol MTX treatment affected the scotopic or photopic b-to-a wave ratio, compared to the PBS control. C-F. Effect of MTX on the rhodopsin level in $Rho^{P23H/+}$ mice. C&D are quantifications of retinal IHC fluorescence intensities from mice treated with single IVI, and E&F are from mice treated with four weekly IVIs. C&E, Spidergrams of the total rhodopsin immunofluorescence intensity (INTST) in the retinae, measured by ImageJ from high magnification immunofluorescence images taken at 0.6, 1 and 1.4 mm from the optic nerve head (ONH). D&F, Spidergrams of rhodopsin immunofluorescence intensity in the ONL from high magnification images taken at 0.6, 1 and 1.4 mm from the ONH. Data points and error bars are means and SEMs, respectively. N=3; *, $p<0.05$ between 25 pmol MTX and PBS groups by an unpaired two-tail Student's t-test.

Figure 14:
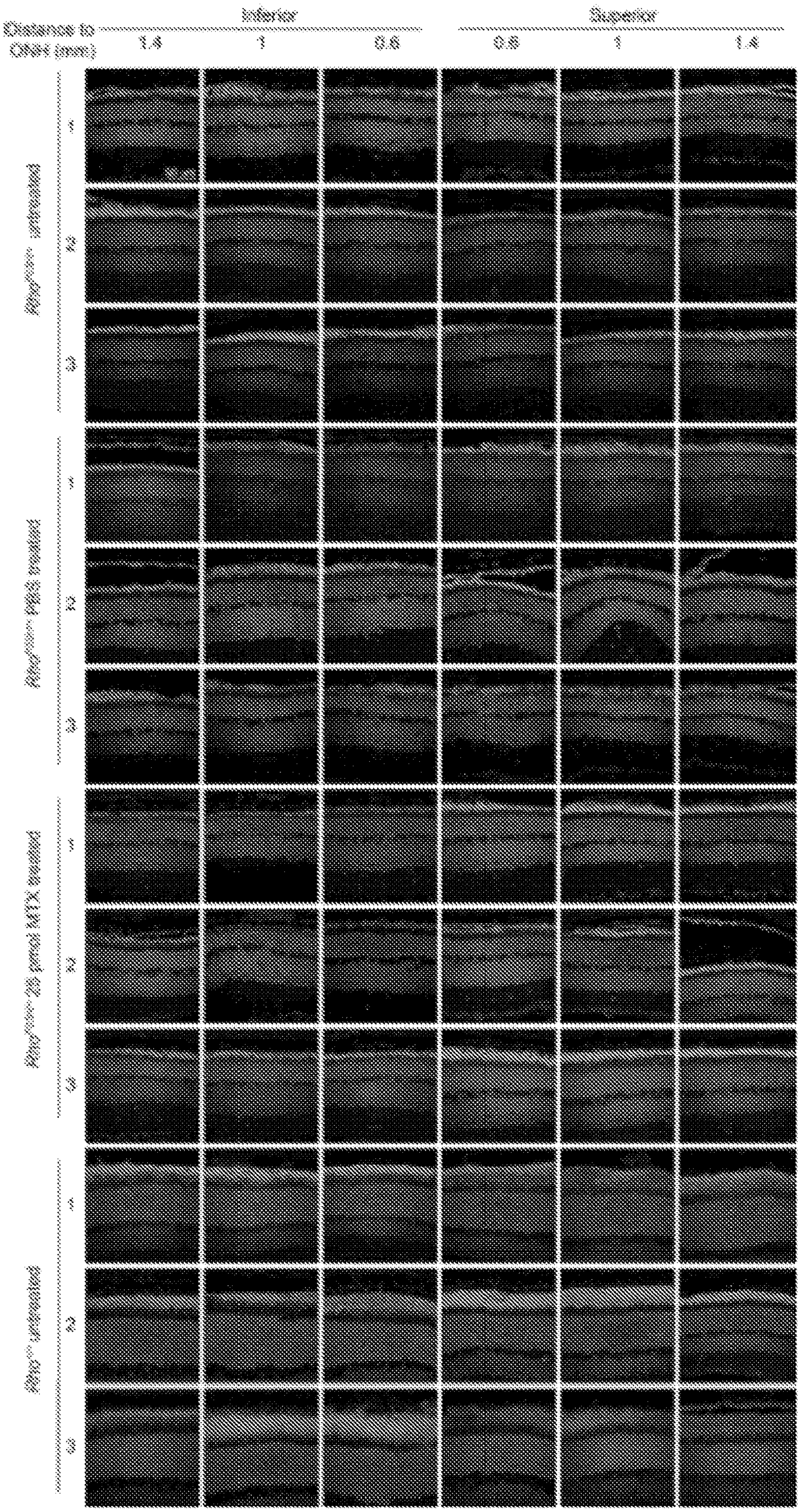

FIG. 14 illustrates immunohistochemistry (IHC) images of $Rho^{+/+}$ and $Rho^{P23H/+}$ mouse retinae treated with one intravitreal injection (IVI). Eyes of $Rho^{P23H/+}$ mice were untreated, or treated with PBS, 25 pmol MTX via an IVI at PND 15, and enucleated at PND 33. Untreated $Rho^{+/+}$ eyes were used as the normal control. Genotype and treatments were labeled vertically on the left. N=3. RHO and nucleus (Hoechst 33342) were stained in red and blue, respectively. Images were taken at 0.6, 1 and 1.4 mm from the optic nerve head (ONH) on the retinal inferior side and the superior side, respectively. Scale bar, 50 μm.

Figure 15:
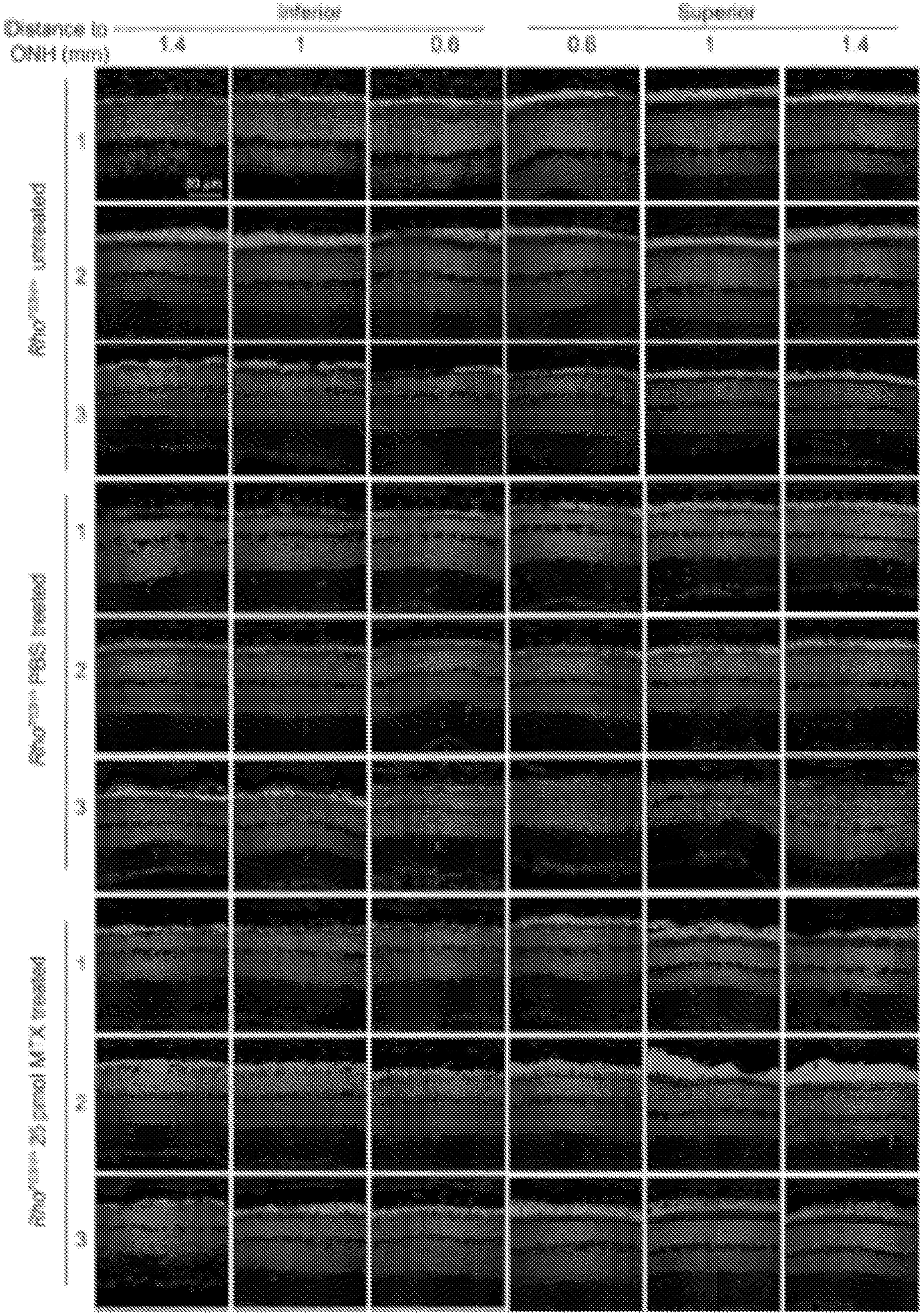

FIG. 15 illustrates IHC images of $Rho^{P23H/+}$ mouse retinae treated with four weekly IVIs. Eyes of $Rho^{P23H/+}$ mice were untreated or treated by four weekly IVIs of PBS or 25 pmol MTX each time, starting at PND 15. Eyes were enucleated at PND 46 for IHC. Genotype and treatment conditions were labeled vertically on the left. N=3. RHO and nucleus (Hoechst 33342) were stained in red and blue, respectively. Images were taken at 0.6, 1 and 1.4 mm from the optic nerve head (ONH) on the retinal inferior side and the superior side, respectively. Scale bar, 50 μm.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

By "reduces" or "increases" is meant a negative or positive alteration, respectively, of at least 10%, 25%, 50%, 75%, or 100%

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

The term "wild-type" or "wild-type conformation" refers to the 3 dimensional conformation or shape of a protein that is free of mutations present in its amino acid sequence that affect the conformation or shape of the protein, such that protein function is altered relative to wild-type protein function. For opsin, a wild-type conformation is a conformation that is free from mutations that cause mis-folding, such as the mutation designated P23H (P23H opsin) (see, for example, GenBank Accession Nos. NM000539 and NP000530) (meaning that a proline is replaced by a histidine at residue 23 starting from the N-terminus). Opsin in a "wild-type conformation" is capable of opsin biological function, including but not limited to, retinoid binding, visual cycle function, and insertion into a photoreceptor membrane.

By "mis-folded opsin protein" is meant a protein whose tertiary structure differs from the conformation of a wild-type protein, such that the misfolded protein lacks one or more biological activities associated with the wild-type protein.

"P23H rhodopsin" means any nucleic acid or protein of P23H rhodopsin.

All percentages and ratios used herein, unless otherwise indicated, are by weight.

Embodiments described herein relate to compounds and methods of treating an inherited ocular disorder associated with or caused by misfolded ocular proteins in a subject in need thereof. It was found that reducing misfolded ocular proteins, such as misfolded opsin proteins, can be an effective strategy to preserve or rescue rod photoreceptors in subjects with inherited ocular disorders associated with or caused by the misfolded ocular protein. Using a small molecule high-throughput screening assay, compounds were identified that selectively reduced misfolded mutant ocular proteins without an effect on corresponding wild type proteins. The compounds were found to promote clearance or accelerate degradation of misfolded ocular proteins, preserve visual function, and prevent photoreceptor death related to the inherited ocular disorder.

In some embodiments, a method of treating an inherited ocular disorder associated with or caused by a misfolded ocular protein in a subject in need thereof includes administering to the subject a therapeutically effective amount of a compound that promotes clearance of misfolded ocular proteins in a subject in need thereof. In some embodiments, a compound can be selected that promoted degradation of a misfolded mutant ocular protein (e.g., misfolded mutant opsin or rhodopsin) but not the corresponding wild type ocular protein in cells. Compounds identified using a high throughput screening assay described herein that that promoted degradation of a misfolded mutant ocular protein (e.g., misfolded mutant opsin or rhodopsin) but not the corresponding wild type ocular protein in cells are selected from:

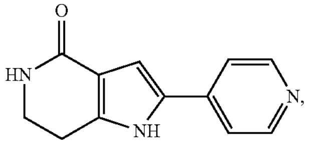

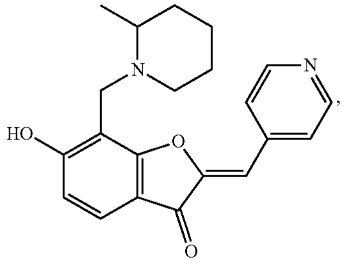

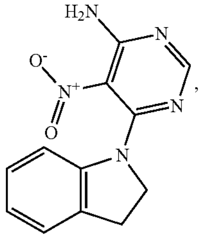

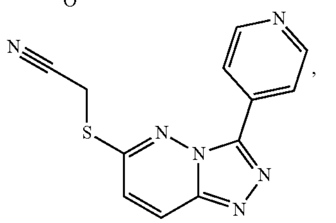

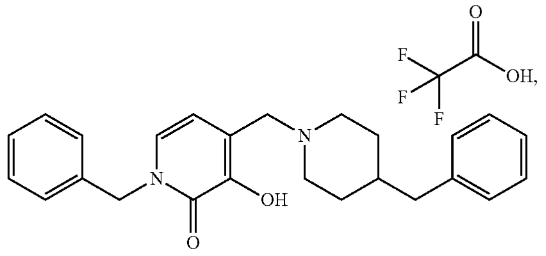

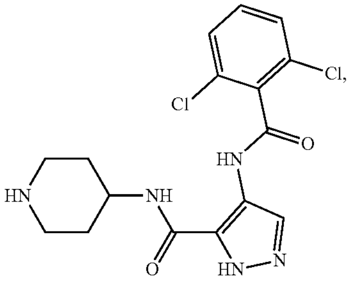

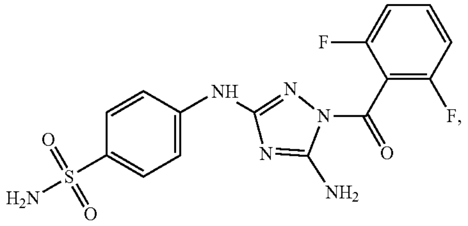

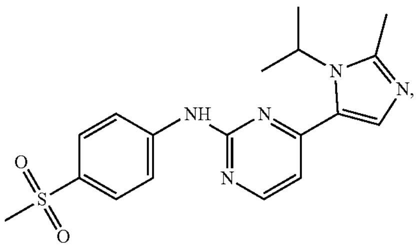

-continued

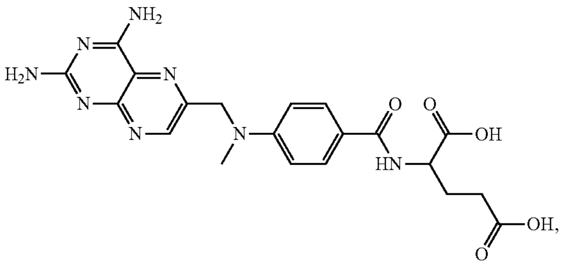

a pharmaceutically acceptable salt, tautomer, or solvate thereof, or combinations thereof.

In some embodiments, the inherited ocular disorder is a non syndromic retinal disorder associated with or by the misfolded ocular protein. For example, the non syndromic retinal disorder can be non syndromic autosomal dominant retinitis pigmentosa (adRP) associated with or caused by the misfolded ocular protein.

In other embodiment, the compound can be selected from:

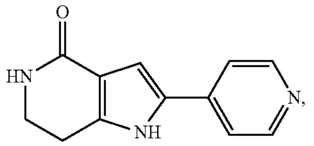

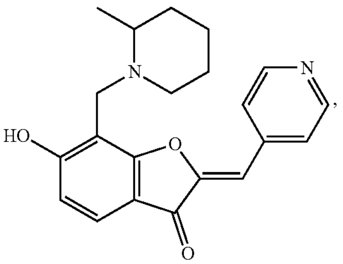

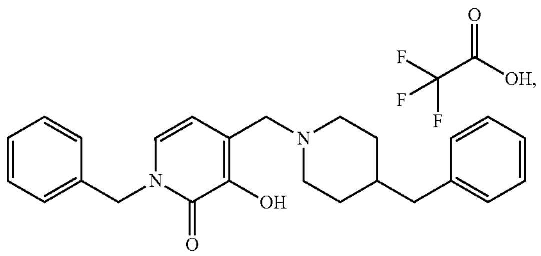

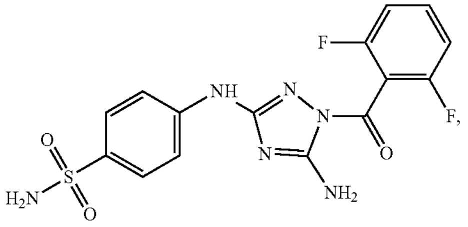

-continued

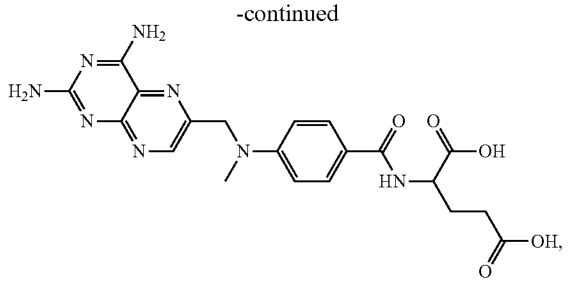

a pharmaceutically acceptable salt, tautomer, or solvate thereof, or combinations thereof.

Advantageously, the compound can be:

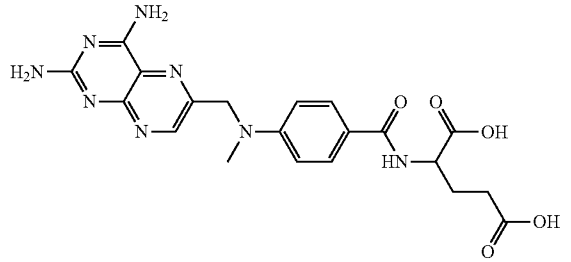 [SMILES: CN(Cc1cnc2nc(N)nc(N)c2n1)c1ccc(C(=O)NC(CCC(=O)O)C(=O)O)cc1]

or a pharmaceutically acceptable salt, tautomer, or solvate thereof. A compound having this formula is also referred to as Methotrexate. Methotrexate is a non-naturally occurring chemical also known as N-[4-[[(2,4-diamino-6-pteridinyl)methyl]methylamino]benzoyl]-L-glutamic acid.

In certain embodiments, the compounds described herein can be used in a method of treating, preventing, ameliorating, or slowing progression of retinitis pigmentosa (RP) or autosomal dominant retinitis pigmentosa (AdRP) in a subject. The method can include administering to the subject a compound described herein, thereby treating, preventing, ameliorating, or slowing progression of retinitis pigmentosa (RP) or autosomal dominant retinitis pigmentosa (AdRP) in the subject.

In other embodiments, the compounds described herein can be used in a method of improving or preserving visual function, visual field, photoreceptor cell function, ERG response, or visual acuity in a subject having a P23H rhodopsin mutant allele or having retinitis pigmentosa (RP), such as autosomal dominant retinitis pigmentosa (AdRP). The method can include administering a compound described herein to the subject. In certain embodiments, a method of inhibiting, preventing, or delaying progression of photoreceptor cell loss and/or deterioration of the retina outer nuclear layer (ONL) in a subject having a P23H rhodopsin mutant allele or having retinitis pigmentosa (RP), such as autosomal dominant retinitis pigmentosa (AdRP), comprises administering a compound described herein to the subject.

In some embodiments, the misfolded ocular protein is a misfolded opsin. The methods may be carried out in vitro or in vivo and the opsin protein may be in a medium, such as a buffer, or may be contained within a cell. Such cell is commonly a mammalian cell, such as a human cell, and may also be a recombinant cell or part of a cell line having selected biochemical or physiological properties. In one embodiment, the cell is an ocular cell, such as a retinal cell. The cell can be a vertebrate or mammalian (e.g., a human) photoreceptor cell (e.g., a rod cell, a cone cell). In one embodiment, the rod cell is present in a mammalian eye, such as a human eye.

In specific embodiments, the misfolded opsin protein can include a mutation in its amino acid sequence. For example, the misfolded mutant opsin protein can be misfolded mutant rhodopsin, wherein the mutation is at least one of P23H, C110Y, D190N, T17M, P347S, or P267L.

Other embodiments described herein relate to a, a method of ameliorating loss of photoreceptor function in a mammalian eye by administering a therapeutically effective amount of a compound described herein to a mammal afflicted with a mutant opsin protein that has reduced affinity for 11-cis-retinal, whereby the compound promotes clearance of the mutant opsin protein, thereby ameliorating loss of photoreceptor function in said mammalian eye. In one embodiment, the contacting occurs by administering compound described herein to a mammal afflicted with the reduced photoreceptor function.

In some embodiments, such loss of photoreceptor function may be a partial loss or a complete loss, and where a partial loss it may be to any degree between 1% loss and 99% loss. In addition, such loss may be due to the presence of a mutation that causes mis-folding of the opsin, such as where the mutation is the P23H mutation.

In another embodiment, the opsin binding agent can be administered to ameliorate an opthalmic condition related to the mislocalization of a misfolded opsin protein. In one embodiment, administration of compound described herein to a subject having a mislocalized opsin protein promotes clearance of the mislocalized opsin protein. Accordingly, the methods and compounds described herein are useful to prevent or treat an ophthalmic condition related to opsin mislocalization associate with a misfolded opsin protein.

Optionally, the compounds described herein can be administered together with another therapeutic agent. For example, the compounds described herein can be used in combination with a synthetic retinoid (e.g., as disclosed in U.S. Patent Publication No. 2004-0242704), and optionally with another active compound (e.g., as discussed herein). In still another embodiment, the compounds described herein can be administered in combination any other agent that can promote clearance of mutant P23H opsin protein.

The compounds used in methods described herein can be administered to the subject using standard delivery methods including, for example, topical and systemic delivery methods, such as ophthalmic, parenteral, subcutaneous, intravenous, intraarticular, intrathecal, intramuscular, intraperitoneal, and intradermal injections, or by intravitreal injection, intraocular injection or periocular injection. The particular approach and dosage used for a particular subject depends on several factors including, for example, the general health, weight, and age of the subject. Based on factors such as these, a medical practitioner can select an appropriate approach to treatment.

"Treating" or "treatment" as used herein, refers to the reduction in severity and/or frequency of symptoms, elimination of symptoms and/or underlying cause, prevention of the occurrence of symptoms and/or their underlying cause, and improvement or remediation of disease. Such treatment need not necessarily completely ameliorate the disease. For example, treatment of a subject with retinal degeneration by administration of the compounds described herein can encompass inhibiting or causing regression of the disease. Further, such treatment can be used in conjunction with other traditional treatments for retinal degeneration known to those of skill in the art.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In some embodiments, the compounds can be administered after induction of retinal degeneration has occurred.

The treatment methods can include administering to the subject a therapeutically effective amount of a compound described herein. For example, pharmaceutical compositions for use in the methods described herein can have a therapeutically effective amount of the compound or salts thereof in a dosage in the range of 0.01 to 1,000 mg/kg of body weight of the subject, and more preferably in the range of from about 10 to 100 mg/kg of body weight of the patient.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers can be composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

Pharmaceutical compositions can optionally further contain one or more additional proteins as desired, including plasma proteins, proteases, and other biological material, so long as it does not cause adverse effects upon administration to a subject. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) or transgenic animals that contain a gene that expresses a human plasma protein which has been introduced according to standard transgenic techniques.

Pharmaceutical compositions can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions can also contain one or more osmotic modulating agents, i.e., a compound that modulates the osmotic properties (e.g., tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) maybe present in any concentration sufficient to modulate the osmotic properties of the formulation.

Compositions comprising the compounds described herein can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Other delivery systems can include time-release, delayed release or sustained release delivery systems. Such systems can avoid repeated administrations of compositions, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates polycaprolactones, polyesteramides, polyorthoesters, polyhydroxybutyric acids, such as poly-D-(−)-3-hydroxybutyric acid (European Patent No. 133,988), copolymers of L-glutamic acid and gamma-ethyl-L-glutamate (Sidman, K R. et at, Biopolymers 22:547-556), poly (2-hydroxyethyl methacrylate) or ethylene vinyl acetate (Langer, ft et at, J. Biomed. Mater. Res. 15:267-277; Langer, B. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono-, di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fined implants; and the like. Specific examples include, but are not limited to: (a) erosional systems in which the agent is contained in a form within a matrix, such as those described in 13.5. U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Compositions including the compounds described herein are particularly suitable for treating ocular diseases or conditions, such as retinitis pigmentosa.

In one approach, the compositions can be administered through an ocular device suitable for direct implantation into the vitreous of the eye. The compositions may be provided in sustained release compositions, such as those described in, for example, U.S. Pat. Nos. 5,672,659 and 5,595,760. Such devices are found to provide sustained controlled release of various compositions to treat the eye without risk of detrimental local and systemic side effects. An object of the ocular method of delivery is to maximize the amount of drug contained in an intraocular device or implant while minimizing its size in order to prolong the duration of the implant. See, e.g., U.S. Pat. Nos. 5,378,475; 6,375,972, and 6,756,058 and U.S. Publications 20050096290 and 200501269448. Such implants may be biodegradable and/or biocompatible implants, or may be non-biodegradable implants.

Biodegradable ocular implants are described, for example, in U.S. Patent Publication No. 20050048099. The implants may be permeable or impermeable to the active agent, and may be inserted into a chamber of the eye, such as the anterior or posterior chambers or may be implanted in the sclera, transchoroidal space, or an avascularized region exterior to the vitreous. Alternatively, a contact lens that acts as a depot for compositions of the invention may also be used for drug delivery.

In some embodiments, the implant may be positioned over an avascular region, such as on the sclera, so as to allow for transcleral diffusion of the drug to the desired site of treatment, e.g., the intraocular space and macula of the eye. Furthermore, the site of transcleral diffusion is preferably in proximity to the macula. Examples of implants for delivery of a composition of the invention include, but are not limited to, the devices described in U.S. Pat. Nos. 3,416,530; 3,828,777; 4,014,335; 4,300,557; 4,327,725; 4,853,224; 4,946,450; 4,997,652; 5,147,647; 164,188; 5,178,635; 5,300,114; 5,322,691; 5,403,901; 5,443,505; 5,466,466; 5,476,511; 5,516,522; 5,632,984; 5,679,666; 5,710,165; 5,725,493; 5,743,274; 5,766,242; 5,766,619; 5,770,592; 5,773,019; 5,824,072; 5,824,073; 5,830,173; 5,836,935; 5,869,079, 5,902,598; 5,904,144; 5,916,584; 6,001,386; 6,074,661; 6,110,485; 6,126,687; 6,146,366; 6,251,090; and 6,299,895, and in WO 01/30323 and WO 01/28474, all of which are incorporated herein by reference.

Other approaches for ocular delivery include the use of liposomes to target a compound described herein to retinal pigment epithelial cells and/or Bruch's membrane. For example, the compound maybe complexed with liposomes in the manner described above, and this compound/liposome complex injected into patients with an ocular disorder, such as retinitis pigmentosa, using intravenous injection to direct the compound to the desired ocular tissue or cell. Directly injecting the liposome complex into the proximity of the retinal pigment epithelial cells or Bruch's membrane can also provide for targeting of the complex with some forms of ocular disorders, such as retinitis pigmentosa. In a specific embodiment, the compound is administered via intra-ocular sustained delivery (such as VITRASERT or ENVISION. In a specific embodiment, the compound is delivered by posterior subtenons injection. In another specific embodiment, microemulsion particles containing the compositions of the invention are delivered to ocular tissue to take up lipid from Bruchs membrane, retinal pigment epithelial cells, or both.

Compositions including the compounds described herein may also be delivered topically. For topical delivery, the compositions are provided in any pharmaceutically acceptable excipient that is approved for ocular delivery. Preferably, the composition is delivered in drop form to the surface of the eye. For some applications, the delivery of the composition relies on the diffusion of the compounds through the cornea to the interior of the eye.

In one example, a compound described herein can be provided in an ophthalmic preparation that can be administered to the subject's eye. The ophthalmic preparation can contain the compound in a pharmaceutically acceptable solution, suspension or ointment. Some variations in concentration will necessarily occur, depending on the particular compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

In some embodiments, a composition used in the methods described herein can include methotrexate. A composition including methotrexate can be formulated for repeated injection.

In some embodiments, the methotrexate is formulated for sustained release. A number of sustained release formulations of methotrexate are known in the art, including but not limited to biodegradable implants such as lipid-encapsulated formulations, e.g., Depo/Methotrexate, as described in Bonetti et al., Cancer Chemother Pharmacol 33:303-306 (1994) and Chatelut et al., J Pharm Sci. 1994 March; 83 (3): 429-32; multivesicular liposome (MVL) formulations of methotrexate (MTX), e.g., as described in WO2011143484; nano- or micropartricules, e.g., alpha-lactalbumin microparticles, e.g., as described in Vijayaragavan et al., Int J Pharm Res 3 (1): 39-44 (2011) or nanoparticles of conjugated methotrexate-human serum albumin as described in Taheri et al., J Nanomaterials 2011 (dx.doi.org/10.1155/2011/768201); polyion complex (PIC) micelles; bioadhesive polymers such as hydroxypropyl methylcellulose (HPMC), carboxymethylcellulose (CMC) and polyacrylic acid (PAA) derivatives, as well as hyaluronic acid (HA), e.g., Lacrisert (Aton Pharma), which is a soluble hydroxy propyl cellulose ocular insert.

Alternatively, or in addition, sustained release can be achieved using a sustained-release device such as intravitreal implants, e.g., as described in Palakurthi et al., Current Eye Research, 35 (12): 1105-1115 (2010) or similar to the Retisert (Bausch & Lomb), Ozurdex (Allergan); or non-biodegradable implants, e.g., similar to Iluvien (Alimera) or Vitrasert (Bausch & Lomb) implants; the I-vation platform (SurModics Inc.). See also Lee et al., Pharm Res. 27 (10): 2043-53 (2010); Haghjou et al., J Ophthalmic Vis Res. 6 (4): 317-329 (2011); Kim et al., Invest. Ophthalmol. Vis. Sci. 45 (8): 2722-2731 (2004); and Velez and Whitcup, Br J Ophthalmol 83:1225-1229 (1999).

The compositions including the compounds described herein, as described above, can be administered in therapeutically effective or effective amounts. The term "therapeutically effective amount" refers to an amount (dose) effective in treating a subject, having, for example, retinal degeneration related disease or disorder (e.g., retinitis pigmentosa). The therapeutically effective amount will depend upon the mode or administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject suffering from retinitis pigmentosa, an effective amount is sufficient to promote clearance of the misfolded opsin protein in a cell. With respect to a subject having a disease or disorder related to a misfolded protein, an effective amount is an amount sufficient to stabilize, slow, or reduce the symptom associated with a pathology such as retinitis pigmentosa.

In some embodiments, a therapeutically effective amount of the compound administered to the subject is an amount effective to accelerate the degradation of the misfolded ocular protein, improve ocular protein homeostasis, improve or preserve visual function, inhibit photoreceptor cell death, and/or improve or preserve retinal structure.

In some embodiments, the improvement or preservation in visual function include an improvement or preservation of photopic electroretinogram (ERG) response. In other embodiments, the improvement or preservation in retinal structure is an improvement or preservation of outer nuclear layer (ONL) thickness.

Generally, doses of the compounds of the present invention would be from about 0.01 mg/kg per day to about 1000 mg/kg (e.g., 0.01, 0.05, 0.1, 0.25, 0.5, 1.0, 5, 10, 15, 20, 25) per day. It is expected that doses ranging from about 50 to about 2000 mg/kg (e.g., 50,100,200, 250, 500, 750, 1000, 1250, 1500, 1750, 2000) will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition including the compounds described herein.

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the compound is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount of the compound may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of 10 μg/kg/day, 50 μg/kg/day, 100 μg/kg/day, 250 μg/kg/day, 500 μg/kg/day, 1000 μg/kg/day or more. In various embodiments, the amount of the 15-PGDH inhibitor or pharmaceutical salt thereof is sufficient to provide a dosage to a patient of between 0.01 μg/kg and 10 μg/kg; 0.1 μg/kg and 5 μg/kg; 0.1 μg/kg and 1000 μg/kg; 0.1 μg/kg and 900 μg/kg; 0.1 μg/kg and 900 μg/kg; 0.1 μg/kg and 800 μg/kg; 0.1 μg/kg and 700 μg/kg; 0.1 μg/kg and 600 μg/kg; 0.1 μg/kg and 500 μg/kg; or 0.1 μg/kg and 400 μg/kg.

In one aspect, a pharmaceutical composition comprising an effective amount of the compound is administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder being treated or how the subject has responded to prior treatments.

In some embodiments, the compounds described herein can be administered to the subject at early stage or mid stage of the non syndromic autosomal dominant retinitis pigmentosa. The retinitis pigmentosa disease course can be conveniently divided into three stages, i.e., the early stage, mid stage, and end stage.

In the early stage, night blindness is the main symptom. It may be present from the first years of life or may appear during the second decade, or even later. At this stage, there may be peripheral visual field defects in dim light. However, these defects do not exist or are minimal in day light, thus patients have normal life habits and the disease may appear stable. Diagnosis is difficult to establish at this stage, particularly when there is no familial history (about half of the cases). Visual acuity is normal or subnormal. Fundus examination may seem normal, as bone spicule-shaped pigment deposits are not present or rare. Moreover, the attenuation of retinal arterioles is modest and the optic disc is normal. The electroretinogram (ERG) is the key test. In most cases, it shows a decreased amplitude of the b-wave that predominates in scotopic conditions. However, ERG may appear normal when the retina is only partially affected, though the decrease in maximum ERG amplitude.

In the mid stage, the clinical picture is complete. Night blindness is obvious, with difficulties to drive during the night, and to walk at evening and in dark staircases. Patients become aware of the loss in the peripheral visual field in day light conditions through stereotypic situations: while driving, they do not see pedestrians or side-coming cars, they miss hands in handshaking and frequently step into various objects. Consequently, patients adapt themselves by avoiding night driving and circulation in unfamiliar places. Dyschromatopsia to pale colors (particularly blue and yellows hues) is often present. In addition, patients become photophobic, especially in presence of diffuse light (white cloudy weather). This leads to reading difficulties, with a narrow window between insufficient and too bright light. Difficulties with reading are due also to decreased visual acuity, partly because of macular involvement (macular edema or mild foveomacular atrophy) and subcortical posterior cataract. Fundus examination reveals the presence of bone spicule-shaped pigment deposits in the mid periphery, along with atrophy of the retina. Narrowing of the retinal vessels is evident and the optic disc is moderately pale. In contrast, the extreme periphery and the macular region appear relatively spared, although mild macular involvement is frequent. The ERG is usually unrecordable in scotopic conditions (rods) and the cone responses (30-Hz flickers, bright light) are markedly hypovolted.

In the end stage, patients can no longer move autonomously, as a result of peripheral vision loss (classical tunnel vision), with few degrees of remaining visual field around the fixation point. Reading is difficult and magnifying glasses are necessary. Photophobia is intense. Fundus examination reveals widespread pigment deposits reaching the macular area. Vessels are thin and the optic disc has a waxy pallor. Fluorescein angiography detects chorioretinal atrophy in the periphery and also in the foveomacular area. The ERG is unrecordable.

In one embodiment, a subject is diagnosed as having symptoms of retinitis pigmentosa (such as impaired vision, night blindness, light sensitivity, tunnel vision, and loss of peripheral vision to total loss of vision), and then a disclosed compound is administered. In another embodiment, a subject may be identified as being at risk for developing retinitis pigmentosa (risk factors may include family history or testing positive for a rhodopsin mutation), and then a disclosed compound is administered. In yet another embodiment, a subject may be diagnosed as having retinitis pigmentosa and then a disclosed compound is administered. In another embodiment, a subject is diagnosed as having symptoms of other forms of retinal degeneration whose etiology involves a rhodopsin mutation (e.g., a P23H rod opsin mutation) in photoreceptor cells of a subject, and then the compound is administered. In another embodiment, a subject may be identified as being at risk for developing other forms of retinal degeneration whose etiology is a rhodopsin mutation) in photoreceptor cells, and then the disclosed compound is administered. In some embodiments, a compound is administered prophylactically. In some embodiments, a subject has been diagnosed as having the disease before retinal damage is apparent. In some embodiments, a human subject may know that he or she is in need of the retinal generation treatment or prevention.

In some embodiments, a subject may be monitored for the extent of retinal degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

Another strategy for treating a subject suffering from a retinal degeneration is to administer a therapeutically effective amount of a compound described herein along with a therapeutically effective amount of an additional compound that acts as a chaperone of rhodopsin and/or an anti-retinal degeneration agent or therapy. Examples of anti-retinal degeneration agents or therapies include but are not limited to supplements, such as vitamin A, DHA, and lutien, as well as optic prosthetic devices, gene therapy mechanisms and retinal sheet transplantations.

Those of skill in the art will recognize that the best treatment regimens for using any of the compounds of the present invention to treat retinitis pigmentosa can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained front the initial clinical trials and the needs of a particular patient.

Example

In this example, we targeted rhodopsin homeostasis in the rod cells expressing a mutant rhodopsin by small molecules for a preventive treatment of RHO-associated adRP because this is the first cellular event being disrupted that causes rod stress and death. Here we have identified an approved drug methotrexate (MTX) by high-throughput screening (HTS) with a cell-based assay that selectively accelerated P23H rhodopsin degradation via lysosomal activity. Importantly, MTX improved rhodopsin homeostasis and increased visual function by a single intravitreal injection (IVI) in the $Rho^{P23H/+}$ knock-in mice. Further, multiple weekly IVIs of MTX led to higher photoreceptor cell numbers on the superior retinae of the $Rho^{P23H/+}$ knock-in mice compared to vehicle control. The activity of MTX in inducing misfolded rhodopsin clearance implicates its potential in treating inherited retinal degenerations caused by protein misfolding.

Materials and Methods

Stable Cell Lines

Two Hek293 stable cell lines, Hek293 ($RHO^{WT}$-Rluc) and Hek293 ($RHO^{P23H}$-Rluc) cells were generated which stably express the WT and P23H mutant mouse rhodopsin each fused with a *Renilla* luciferase (Rluc) for the luciferase reporter assay as previously described. Briefly, the Hek 293 cells (ATCC, Manassas, VA, USA) were transfected with the pcDNA3.1 Zeo containing the cDNA of mouse WT or P23H rhodopsin fused with a Rluc 8 (a gift from Dr. Navine Lambert at Augusta University, Augusta, GA USA) and transfected cells were incubated in Dulbecco's modified Eagle's medium (DMEM, Genesee Scientific, El Cajon, CA USA) with 10% fetal bovine serum (FBS, Gibco Laboratories, Gaithersburg, MD USA) for 48 h before addition of 400 μg/mL of Zeocin (InvivoGen, San Diego, CA USA) for positive clone selection. Colonies of cells survived from 1 week of Zeocin selection were collected, and expression of WT and P23H rhodopsin were confirmed by a luciferase assay and immunoblotting of rhodopsin with positive bands of monomers at about 70 kD (FIG. 8). The difference of molecular masses between WT and P23H rhodopsin proteins was due to differences in glycosylation, which was also seen in the NIH3T3 cells expressing the WT and P23H rhodopsin proteins.

Two NIH3T3 stable cell lines, NIH3T3 ($RHO^{WT}$/GFP) and NIH3T3 ($RHO^{P23H}$/GFP) were shared by Dr. Krzysztof Palczewski's lab who generated them by incorporating the pMiLRO 23 and pMiLRO DNA constructs to the NIH3T3 cells, respectively, via viral transduction (24, 33). GFP was co-expressed with rhodopsin for positive-clone selection. The expression of the WT and P23H rhodopsin protein was confirmed by immunoblots and immunostaining.

Seven U2OS stable cell lines were generated which separately express the WT and six mutant mouse rhodopsin (T4R, P23H, P53R, C110Y, D190N, P267L) fused with Venus fluorescence protein. Briefly, the U2OS cells (ATCC, Manassas, VA, USA) were transfected with the pcDNA3.1 Zeo containing the cDNA of mouse WT or T4R, P23H, P53R, C110Y, D190N, P267L rhodopsin fused with Venus and transfected cells were incubated in DMEM with 10% FBS for 48 h before addition of 400 μg/mL of Zeocin for positive clone selection. Colonies of cells survived from 1 week of Zeocin selection were collected, and expression of WT and six mutant rhodopsins were confirmed by fluorescence of Venus and immunoblotting of rhodopsin.

Cell Culture and Media

Cells were cultured in the complete medium containing DMEM with 10% FBS and 5 μg/mL plasmocin (InvivoGen, San Diego, CA USA) at 37° C. with 5% $CO_2$ and >95% humidity, and subcultured as instructed in the ATCC Animal Cell Culture Guide (www.atcc.org).

Chemicals and Reagents

ViviRen was purchased from Promega (Madison, WI, USA), dissolved in dimethyl sulfoxide (DMSO) as 60 mM stock aliquots and stored at −80° C. in amber tubes. The UC 10 k Diversity Set was provided by the University of Cincinnati Drug Discovery Center (UCDDC, Cincinnati, OH USA) at 10 mM per compound in 384-well format, the Spectrum Collection (MicroSource, Gaylordsville, CT USA) and the Life Chemicals 50K Diversity Set (Life Chemicals USA, Woodbridge, CT USA) were provided by Dr. Krzysztof Palczewski at 10 mM per compound in 384-well format, and the U.S. Food and Drug Administration (FDA) approved drugs, Library of Pharmacologically Active Compounds (LOPAC, Millipore Sigma, St. Louis, MO USA) and Mechanism Interrogation Plat E (MIPE) collections were provided by NCATS in 7 or 11 dose series for each compound in 1536-well format. All the compounds in these compound libraries were dissolved in DMSO and stored at −80° C., and sealed with adhesive foil films. Hit compounds were cherry-picked from the compound stock in powder or ordered from chemical vendors for triplicate, dose-response tests, as well as confirmation and counter screens. CL-001 (Pubchem CID: 11715767), CL-006 (CID: 11338033), CL-007 (CID: 5330790), and CL-008 (CID: 16747683) were purchased from Selleckchem (Houston, TX USA); CL-002 (CID: 6224422), CL-003 (CID: 4438424), and CL-004 (CID: 6624030) were ordered from Life Chemicals, CL-005 (CID: 10091681) was provided by UCDDC, and CL-009/MTX (CID: 126941) were purchased from Cayman Chemical (Ann Arbor, MI USA). DMSO and L-methionine were from MilliporeSigma (St. Louis, MO USA). The anti-rhodopsin antibodies 1D4 and B630 were shared by Dr. Krzysztof Palczewski's lab. Anti-microtubule-associated proteins light chain 3 (LC3) antibody was purchased from Cell Signaling Technology (4108S, Danvers, MA USA). The anti-sequestosome 1 (SQSTM1/p62) antibody was purchased from Novus Biologicals (NBP1-42821, Centennial, CO USA). Cy3-conjugated goat anti-mouse IgG (A10521), horseradish peroxidase (HRP)-conjugated goat anti-mouse IgG (32230), HRP-conjugated goat anti-rabbit IgG (32260), HRP-Streptavidin (SA) (434323), L-azidohomoalanine (AHA, C10102), biotin (BTN)-sDIBO (C20023), and Dynabeads™ Protein G (10004D), BCA protein assay (23225), paraformaldehyde (28908), Hoechst 33342 (H3570), and SuperSignal™ West Pico PLUS Chemiluminescent Substrate (34580) were obtained from ThermoFisher (Waltham, MA USA).

HTS and Counter Screening Procedures

The HTS was performed at three facilities, including University of Cincinnati (UC), Case Western Reserve University, and National Center for Advancing Translational Sciences (NCATS), testing a total of six compound collections. These compound collections include: 1) the UC 10K Diversity Set (10,011 compounds), 2) the Life Chemicals 50K Collection (50,560), 3) the Spectrum Collection (2,400 compounds), 4) the LOPAC collection (1,280 compounds), 5) the FDA collection (2,816 compounds), and 6) the NCATS MIPE collection (1,912 compounds). The procedure of the HTS assay and confirmation assays are slightly different (Table 4) to adapt to equipment at different facilities, nonetheless the quality control parameters (signal to noise ratio and Z' factors) demonstrate these assays were robust (Table 1). For the compound collections 1), 2) and 3), we firstly tested each compound using the P23H rhodopsin luciferase reporter assay at a single dose for once (9.93 to 16.13 μM) in 384-well format, and we identified 2072 compounds with activity scores lower than the cutoff at mean-2SD. Activity scores were normalized using DMSO treated cells as 0% control and the 1 mM Evans Blue treated cells as −100% control. From these hit compounds, we excluded those reported with luciferase inhibitor activities and cherry-picked the rest for hit confirmation. Each hit was tested at 10 μM in the Hek293 ($RHO^{P23H}$-Rluc) cells again by the luciferase reporter assay in triplicates, and the confirmed hits with activity scores lower than-50% were then counter screened for their effects on Rluc activity by the recombinant Rluc activity assay, and on WT rhodopsin level by the luciferase reporter assay in the Hek293 ($RHO^{WT}$-Rluc) cells at 10 μM in triplicates, respectively. We identified 52 compounds that do not significantly affect the Rluc activity or the WT rhodopsin-Rluc reporter activity (activity scores higher than-50%). Next, we tested the dose responses of these confirmed hits in both the Hek293 ($RHO^{P23H}$-Rluc) and the Hek293 ($RHO^{WT}$-Rluc) cells and identified compounds that selectively favored the clearance of P23H than WT rhodopsin in a dose-dependent manner (Table 4). For the compound collections 4)-6), we tested each compound directly at 7 or 11 doses using the luciferase reporter assay in the Hek293 ($RHO^{P23H}$-Rluc) cells in 1536-well format, and identified 128 compounds with efficacy smaller than-50% and $EC_{50}$<20 μM. We then cherry-picked these 128 compounds and tested them by the luciferase reporter assay in both Hek293 ($RHO^{P23H}$-Rluc) and Hek293 ($RHO^{WT}$-Rluc) cells in 7 or 11 doses in triplicates and selected 34 compounds that showed higher efficacy towards the clearance of P23H than WT rhodopsin.

TABLE 1

The quality control parameters of the HTS of each compound collection using the luciferase reporter assay

| Number | 1 | 2 | 3 | 4 | 5 | 6 |
|---|---|---|---|---|---|---|
| Compound Library | 10K UC Collection | Spectrum Collection | Life Chemicals 50K collection | FDA Collection | LOPAC | MIPE |
| Location | University of Cincinnati | Case Western Reserve University | Case Western Reserve University | NCATS | NCATS | NCATS |
| Number of compounds | 10,011 | 2,400 | 50560 | 2816 | 1280 | 1912 |
| Tested concentration (μM) | 9.93 | 12.99 | 16.13 | 7 doses | 7 doses | 11 doses |
| Z' range | 0.53-0.71 | 0.54-0.84 | 0.44-0.87 | 0.37-0.61 | 0.52-0.71 | 0.46-0.66 |
| Z' mean ± SD | 0.62 ± 0.05 | 0.71 ± 0.10 | 0.67 ± 0.10 | 0.50 ± 0.07 | 0.63 ± 0.07 | 0.59 ± 0.05 |
| S/B range | 13.07-18.56 | 8.27-51.33 | 70.1-280.5 | 137.24-158.20 | 94.63-184.52 | 145.97-192.00 |
| S/B mean ± SD | 16.00 ± 1.73 | 19.81 ± 19.36 | 140.9 ± 26.3 | 148.21 ± 7.94 | 124.77 ± 28.97 | 159.67 ± 13.66 |
| 0% | DMSO 0.1% | DMSO 0.1% | DMSO 0.1% | | DMSO 0.1% | |
| −100% | Evans Blue 200 μM | Evans Blue 1 mM | Evans Blue 1 mM | | Evans Blue 1 mM | |
| Cutoff (Mean − 2SD) (%) | −50 | −32.25 | −49.76 | | $EC_{50}$ < 20 μM | |
| Number of hits | 82 | 89 | 1901 | | 34 | |
| hit rate (%) | 0.82 | 3.71 | 3.76 | | 0.57 | |

Rluc Reporter Assay

The Rluc reporter assay has been described before. HTS was undertaken in 384-well format for the UC 10K Diversity Set, Spectrum Collection and the Life Chemicals 50K diversity set, and in 1536-well format for the FDA, LOPAC, and MIPE collections. Using the 384-well format as an example, Hek ($RHO^{P23H}$-Rluc) cells were seeded in 384-well white-wall clear-bottom plates (assay plates) at $3\times10^5$/mL for 40 μL/well by an 8-channel Multiflo liquid dispenser (Bioteck, Winooski, VT USA). The assay plates were centrifuged at 300×g for 30 s and cultured at 37° C. with 5% $CO_2$ overnight. On the next day, compounds were transferred by a 50 nL 384-pin tool from 384-well compound plates to 384-well assay plates that contained cultured cells, operated by a JANUS MDT automatic workstation (PerkinElmer, Waltham, MA USA). Compound plates contained 50 μL/well of compound solutions dissolved in DMSO in columns 3-22. Controls were loaded in a control plate in columns 1, 2, 23, and 24, containing 50 μL of DMEM, DMSO, DMSO, and Evans Blue (606 mM in DMSO), respectively. Controls were transferred using the 50 nL pin tool from the compound plate to the assay plate. Before reuse, the pin tool was washed thoroughly by sequentially dipping into wash wells containing 100 mL of DMSO, flushing water, and 100 mL of ethanol and air-dried for 30 s. Treated assay plates were centrifuged at 300×g for 30 s and incubated at 37° C. with 5% $CO_2$ for 24 h. On the third day, 5 μL/well 2% n-Dodecyl-β-D-maltopyranoside (DDM) was added to the assay plates followed by 5 s of shake. The assay plates were incubated at room temperature for 5 min and added with 5 μL/well of 50 μM ViviREN solution diluted in phosphate buffered saline (PBS), followed by 5 s of shake. The assay plates were incubated in dim light at room temperature for 1 h. The luminescence of each well was read by an Enspire plate reader (PerkinElmer) with 0.1 s of integration time. For the 1536-well format of the HTS assay, the procedures are same as the 384-well assay, except for the following differences: cells were seeded at 3000 cells/well in 5 μL/well of a white-wall clear-bottom 1536-well plate; compounds were transferred using a 23 nL1536-pin tool; and 0.5 μL/well of DDM and 1 μL/well of 30 μM ViviREN solution were sequentially added to the assay plates. For the counter screening assay, the assay was repeated as the HTS assay using the Hek293 ($Rho^{WT}$-Rluc) cells. Activity score (%)=($RLU_{compound}$−$RLU_{DMSO}$)/($RLU_{DMSO}$−$RLU_{Evans\ Blue}$)×100. RLU, relative luminescence unit.

Recombinant Rluc Activity Assay

Recombinant Rluc (RayBiotech, Peachtree Corners, GA USA) was dissolved in PBS and diluted to 0.3 μg/mL. Each compound was diluted to 10×final concentration in PBS as the compound working solution. In 384-well plates, 16 μL/well of diluted Rluc was mixed with 4 μL/well of compound working solution. Using a MolecularDevices SpectraMax XL microplate reader, luminescence in each well was read 2.5 s after an injection of 20 μL/well of 5 μM of coelenterazine h substrate (Nanolight Technologies, Pinetop, AZ USA). Each compound was tested at a final concentration of 10 μM and repeated three times. Luciferase activity was normalized by the DMSO and 1 mM Evans Blue as 0% and −100% controls, respectively.

Dot Blot

NIH3T3 ($RHO^{P23H}$/GFP) or NIH3T3 ($RHO^{WT}$/GFP) cells were seeded at $2.5\times10^4$ cells/well in 100 μL/well complete medium in a 96-well plate and cultured at 37° C. with 5% $CO_2$ for 4 h. Cells then were treated with 100 μL/well complete medium containing 2×the final concentration of tested compounds. After 24 h of further incubation at 37° C. with 5% $CO_2$, the medium was aspirated, and the cells were washed once with PBS. The cell lysis buffer containing radioimmunoprecipitation assay (RIPA) buffer and complete protease inhibitor cocktail (Roche Diagnostics, Basel, Switzerland) were added to the cells at 200 μL/well followed by sonication for 6 s. Because the cellular protein level of $RHO^{WT}$ was higher than $RHO^{P23H}$, 5% of one well NIH3T3 ($RHO^{WT}$/GFP) cells samples and 90% of one well NIH3T3 ($RHO^{P23H}$/GFP) cells samples were loaded to a nitrocellulose membrane and air-dried. Opsin protein was immunostained with 0.1 μg/mL HRP-conjugated 1D4 anti-rhodopsin antibody. Densitometry of the bands was measured by the ImageJ software and normalized to DMSO-treating control.

Western Blot

Cells were seeded in 6-well plates at a density of $5\times10^5$ cells/well and cultured at 37° C. with 5% $CO_2$ for 17 h. The medium was replaced with a fresh medium containing a corresponding concentration of compounds. After treatment for 24 h, cells collected and lysed in 150 μL PBS containing 0.1% SDS and complete protease inhibitor cocktail with 12 s of sonication on ice. Retina samples were lysed in 300 μL per retina of PBS containing 0.1% SDS and complete protease inhibitor cocktail under 24 s of sonication on ice. Protein concentrations were determined by measurements of $OD_{280\ nm}$ using a Nanodrop spectrometer. To immunoblot rhodopsin, one hundred μg of total protein for NIH3T3 ($RHO^{P23H}$/GFP) cells, or twenty μg of total protein for NIH3T3 ($RHO^{WT}$/GFP) cells was loaded per well onto an SDS-PAGE gel. To detect other proteins, fifty μg of total protein was loaded per well. After separation by electrophoresis in 10% and 16% SDS-PAGE gels, proteins were transferred to a nitrocellulose membrane using a wet membrane electrotransfer cassette followed by blocking with 5% bovine serum albumin in PBS containing 0.05% Tween 20 for 1 h. The membranes were incubated with primary antibodies at 4° C. overnight following with appropriate secondary antibodies for 1 h at room temperature. Blots were visualized using SuperSignal™ West Pico PLUS chemiluminescent substrate, and scanned by a BioRad gel imager.

High Content Imaging

To assess the effect of active compounds on the clearance of P23H rhodopsin in mammalian cells, an image-based assay was performed using NIH3T3 ($RHO^{WT}$/GFP) and NIH3T3 ($RHO^{P23H}$/GFP) cells, as described previously. Briefly, cells were seeded at 5000 cells per well in 384-well plates and incubated at 37° C. in 5% $CO_2$ for 4 hours until cells were attached to the bottom of the plate. Attached cells were treated with compounds for 24 hours. The assay medium was aspirated, and cells were fixed with 4% paraformaldehyde at 20 μL per well for 20 min at room temperature. Cell membranes were permeabilized with PBS containing 0.1% Triton X-100 (PBST) and then incubated with 50 g/mL 1D4 anti-rhodopsin antibody at 15 μL/well for 1 hour at room temperature. After three washes with 50 μl/well of PBST, cells were incubated with 15 μL/well Cy3-conjugated goat anti-mouse IgG antibody for 1 hour at room temperature. After three washes with 50 μl/well of PBST, cells were incubated in 50 μl/well of PBS containing 2 μg/mL Hoechst 33342 to stain the nuclei. Finally, the immunostained cells were imaged by an ImageExpress High Content Imaging System (MolecularDevices). Immunofluorescence of rhodopsin was measured by MetaXpress software using the mean of total fluorescence of Cy3 channel per cell per well taken from five fields containing 600-1000 intact cells per well. After normalizing the fluorescence intensities of rhodopsin to the DMSO treated cells as 0% and cells immunostained with secondary antibody only as −100%, dose-response curves for each compound were plotted and fitted by a modified Hill function using the Origin software. The high-content imaging experiments for hit validation were performed at the CWRU drug discovery facility, and the high-content imaging analyses for the MTX co-treatment with BafA1 and MG-132 were undertaken at the University of Pittsburgh Drug Discovery Institute. Thus, small differences were seen for CL-009/MTX's activity due to experimental variation.

qPCR

NIH3T3 ($RHO^{WT}$/GFP) and NIH3T3 ($RHO^{P23H}$/GFP) cells were seeded in the 24-well plates at a density of $2.5\times10^5$ cells/well and cultured at 37° C. with 5% $CO_2$ for overnight. Cells were then incubated with the culture medium containing compounds for 24 h. After aspirating the medium, cells were collected and lysed in 300 μL/well of TRIzol (ThermoFisher, 15596026, Waltham, MA USA) for 5 min. Samples were vigorously mixed with 60 μL chloroform for 30 s, then centrifuged at 12,000×g for 15 min at 4° C. The upper aqueous phase containing RNA was taken out and mixed with 150 μL isopropanol by vigorous shaking. After sedation for 10 min, samples were centrifuged at 12,000×g for 10 min at 4° C. The pellets were washed with 300 μL 75% ethanol and centrifuged at 7,500×g at 4° C. for 5 min. The RNA pellets were air-dried for 15 min and dissolved in 30 μL nuclease-free water (FisherScientific, BP2484-100, Houston, TX USA). The yield and purity of RNA were assessed by a NanoDrop spectrometer. The cDNAs was generated from 1 μg RNA using a High-Capacity RNA-to-cDNA Kit (ThermoFisher, 4387406, Waltham, MA USA). qPCR amplifications were performed using the PowerUp SYBR Green Master Mix (ThermoFisher, A25741, Waltham, MA USA) with the cDNA templates and primers, and the reaction was controlled by a QuantStudio 3 thermocycler (ThermoFisher, Waltham, MA USA). Primer sequences are as follows: RHO, forward 5'-CCC TTC TCC AAC GTC ACA GG-3' (SEQ ID NO: 1), reverse 5'-TGA GGA AGT TGA TGG GGA AGC-3' (SEQ ID NO: 2); β-actin, forward 5'-ACC TTC TAC AAT GAG CTG CG-3' (SEQ ID NO: 3), reverse 5'-CTG GAT GGC TAC GTA CAT GG-3' (SEQ ID NO: 4).

Pulse-Chase Assay

To quantify rhodopsin degradation, a non-radioactive pulse-chase assay was used with a 'click' reaction. Briefly, NIH3T3 ($Rho^{P23H}$/GFP) or NIH3T3 ($Rho^{WT}$/GFP) cells were cultured in a 24-well plate at $3\times10^5$ cells/well in the complete medium with 10% FBS. The medium was aspirated after overnight culture, and cells were gently washed once with 1 mL/well of PBS. Cell were incubated in the L-methionine-free DMEM (Gibco, 21013-024, Gaithersburg, MD USA) for 1 h to exhaust the intracellular methionine. Then the cells were pulsed with L-AHA at final concentration 50 μM for 4 h. Meanwhile, the cells treated with 50 μM L-methionine were used as negative control. After labeling, cells were replaced with the complete DMEM medium with 2 mM L-methionine in the presence or absence of active compounds for a varying time of chase. Then cells were lysed with PBS containing 0.1% SDS, 1% DDM and the complete protease inhibitor cocktail. The total protein concentrations were measured by a BCA assay. Cell lysate containing 200 μg total protein was mixed with 5 μM BTN-sDIBO to make a 'click' reaction for 1 h at 37° C. Samples were incubated with Dynabeads™ Protein G binding with 1D4 anti-rhodopsin antibody for 15 min at room temperature followed by three washes with PBS containing 0.02% Tween 20. Proteins were eluted with 50 mM Glycine at pH 2.8 for 10 min at room temperature and then loaded onto nitrocellulose membranes. After air-dried, the membranes were blocked with 5% milk and immunoblotted with 0.25 μg/mL HRP-conjugated SA.

Proteasome Activity Assay

NIH3T3 ($RHO^{P23H}$/GFP), NIH3T3 ($RHO^{WT}$/GFP) and NIH3T3 cells were seeded in a white-wall clear-bottom 384-well plate at 2500 cells/well in 20 μL of complete mediu. After 3 h of incubation, five μL/well of complete medium containing MTX was added to cells to treat cells with MTX at final concentrations from 0.0195 to 10 μM for 24 h. The cells treated with a complete medium containing 0.1% DMSO were used as the 100% control, and those treated with 5 μM MG-132 for 8 h were used as the 0% control. For endpoint proteasome activity measurement, each well was added with 25 μL of Proteasome-Glo™ Reagent containing the Suc-LLVY-Glo™ substrate (Promega, G8660, Madison, WI USA). The 384-well plate was shaken for 2 min to mix the solutions followed by a 24-min incubation at room temperature. Luminescence of each well was detected by a SpectraMax 13× microplate reader (Molecular Devices). The chymotrypsin-like proteasome activity was normalized by the 100% and 0% controls, respectively.

Animals

The C57BL/6J ($Rho^{+/+}$) mice and $Rho^{P23H/P23H}$ mice were purchased from Jackson Laboratory (Stock No 017628) generated by Dr. Krzysztof Palczewski's lab. The $Rho^{P23H/P23H}$ mice were crossed with wild-type C57BL/6J mice to produce P23H heterozygotes mice. Genotyping for all strains was conducted as guided using forward and reverse primers: 1) GGT AGC ACT GTT GGG CAT CT (SEQ ID NO: 5); and 2) GAC CCC ACA GAG ACA AGC TC (SEQ ID NO: 6), respectively. The PCR products at 573 and 399 bp indicated the P23H knock-in mutant and WT allele of the RHO gene, respectively. Mice were bred and housed under standard 12-h light/12-h dark conditions in the University of Pittsburgh animal facility. All animal experiments were approved by the University of Pittsburgh Institutional Animal Care and Use Committee (IACUC) following the guide for the Animal Welfare Act and Regulations.

Intravitreal Injection (IVI)

To determine the effect of compounds on retina in vivo, we administered compounds directly into the vitreous space. Briefly, mice were treated with 1% tropicamide eye drops (Akorn, Lake Forest, IL USA) to dilate the pupils and then they were anesthetized with an intraperitoneal injection of ketamine (Henry Schein, Dublin, OH USA) at 80 mg/kg body weight (bw) and xylazine (Bimeda, Le Sueur, MN USA) at 7 mg/kg bw. One drop of 0.5% tetracaine hydrochloride (TCI, Tokyo, Japan) was applied to mouse eyes as topical anesthetics before injection. Eyes were kept lubricated during the injections by a 0.3% hypromellose eye gel (Alcon, Fort Worth, TX USA). A heating pad was used for maintaining body temperature. Mice were positioned to expose the sclera of the eyes. A 30-gauge needle (Medline, Northfield, IL USA) was used to puncture a hole through sclera behind limbus at a 45° angle. A 33-gauge blunt-end needle (Hamilton, Reno, NV USA) was used to be inserted into the hole and a total of 0.5 μL of sterile PBS or MTX in PBS was slowly injected into the posterior chamber and the needle was kept in place for about 30 seconds before a slow removal of the needle. A small amount of Triantibiotic ointment (Medline, Northfield, IL USA) was applied on the injection site to prevent infection. A single IVI with 25 or 100 pmol of MTX was administered to one eye of each $Rho^{P23H/+}$ mice at postnatal day (PND) 15, and PBS was injected to the other eye as vehicle control. We also performed four weekly IVIs of MTX or PBS to the second group of $Rho^{P23H/+}$ mouse eyes at PND 15, 22, 29 and 36.

Electroretinogram (ERG)

ERG was performed using the Celeris system (Diagnosys, Lowell, MA, USA), as described previously. Before each test, mice were kept in the dark overnight. Pupils were dilated with 1% tropicamide (Akorn, Lake Forest, IL, USA). Mice were anesthetized with an intraperitoneal injection of ketamine at 80 mg/kg bw and xylazine at 7 mg/kg bw. Eyes were lubricated by a 0.3% hypromellose eye gel (Alcon, Fort Worth, TX, USA). A heating pad was used to maintain body temperature at 37° C. Scotopic ERG responses of dark-adapted eyes to ten flashes from 0.01 $cd\cdot s/m^2$ to 30 $cd\cdot s/m^2$ were recorded and averaged from three sweeps per flash intensity with inter-sweep intervals of 10 to 30 s. After exposed to 10 $cd/m^2$ illumination for 5 min, the photopic ERG responses were recorded from the light-adapted eyes in respond to flashes from 0.01 $cd\cdot s/m^2$ to 30 $cd\cdot s/m^2$ in addition to a 10 $cd/m^2$ background light. P-values were calculated by a two-way ANOVA to determine the statistical significance between the response amplitudes in the MTX-treated and vehicle (PBS) group. Factor 1, treatment condition; and factor 2, flash intensity.

Tissue Collection and Immunohistochemistry (IHC)

Mice were euthanized and the superior side of each eye was labeled by a burn mark generated by a Cautery pen. Eyes were enucleated by a pair of curved-tip forceps and fixed in the freshly prepared 4% paraformaldehyde for 2 h. Fixed eyes were dehydrated sequentially in 5, 10, 20 and 40% sucrose solutions in PBS each for 30 min at room temperature. Finally, eyes were incubated in a mixture of 40% sucrose in PBS and O.C.T. compound (FisherScientific, Houston, TX USA) at 1:1 volume ratio for overnight at 4° C. before they are embedded in the same mixed solution in an orientation-specific manner and frozen in liquid nitrogen-bathed isobutene. Twelve-micron retinal cross-sections were made by a microtome at −16° C. and those containing the optic nerve head were applied onto a SuperFrost glass slide (FisherScientific, Houston, TX USA). These slides were then used for IHC. After rehydration and permeabilization in PBST for 15 min, retinal sections were incubated in 5% goat serum for 30 min, and then they were incubated with PBS containing the mouse 1D4 anti-rhodopsin antibody (20 μg/mL) for 2 hours at room temperature in a humidified chamber. The retinal sections were washed with PBST for four times and incubated with Cy3 conjugated goat anti-mouse antibody (5 μg/mL) for 1 hour at room temperature. Hoechst 33342 (1:10000 dilution) was applied for 5 min to stain the nuclei. Sections were mounted with the Prolong-Gold mounting solution (ThermoFisher, Waltham, MA USA). Immunofluorescence images were then taken by a fluorescence microscope for low-magnification images and a confocal microscope for high-magnification images. A total of six high magnification images were taken using a 60×objective with oil per retinal cryosections at proximately 0.6, 1.0 and 1.4 mm to the optic nerve head (ONH). Immunofluorescence intensity of rhodopsin in OS, and outer nuclear layers (ONL) were measured using ImageJ by selecting corresponding layers using a magic wand and measuring the fluorescent intensity within the selected area. Nucleus number in ONL was calculated by counting the Hoechst33343 positive objects in the ONL in each high magnification image that spans 200 μm along the retina.

Statistical Analyses

The HTS and high-content imaging assays were performed with each assay plate containing 16 repeats of 0% and −100% controls and Z' was calculated plate by plate to make sure Z'>0.5 for HTS and Z'>0 for high-content imaging assay indicating results in each plate were robust and activity scores calculated properly by the controls. Z'=1-3×($SD_{0\%\ control}$+$SD_{-100\%\ control}$)/($Mean_{0\%\ control}$−$Mean_{-100\%\ control}$).

The ERG recordings were analyzed by a two-way analysis of variance (ANOVA), because the ERG responses can be affected by two factors, compound treatment (factor 1) and flash intensity (factor 2). $p_1$ and $p_2$ determined whether compound treatment and flash intensity significantly affect the ERG response, respectively; whereas $p_{1-2}$ determined whether the two factors interact with each other. The other assays were analyzed by the unpaired two-tailed Student's t-test. The criteria for significance was: not significant, P>005; *, P<0.05;  P<0.01; *, P<0.001; ****, P<0.0001. Sample size was chosen based on power analyses using the functions:

$$n = \left(\sigma_A^Z + \sigma_B^Z\right)\left(\frac{z_{1-\alpha/1} + z_{1-\beta}}{\mu_A - \mu_B}\right)^2; \tag{1}$$

and $$1 - \beta = \Phi\left(\frac{|\mu_A - \mu_B|\sqrt{n}}{\sqrt{\sigma_A^Z + \sigma_B^Z}} - z_{1-\frac{\alpha}{\tau}}\right); \tag{2}$$

where σ is SD, Φ the standard normal distribution function, α is Type I error or P-value set at 0.05, τ is the number of comparisons to be made, β is the Type II error, and 1-β is the power set at 0.90 (39). Both males and females were included randomly in each sample group of the animal studies.

Results

HTS Identified 46 Compounds that Selectively Reduced P23H Rhodopsin

Figure 1A:
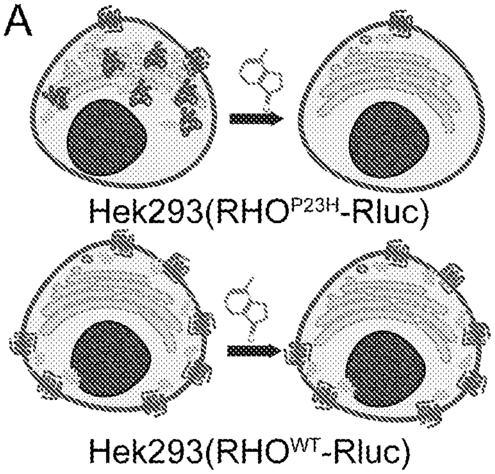
FIGS. 1(A-H) illustrate schematic images, plots, and charts showing high-throughput screening (HTS) for small molecules that selectively reduce the misfolded P23H rhodopsin. A. Illustration of the cell-based luciferase reporter assay for HTS and counter screen. The mouse P23H or wild type (WT) rhodopsin was fused with *Renilla* luciferase (Rluc) and constitutively expressed in Hek293 cells, marked as the Hek293 (RHO$^{P23H}$-Rluc), or Hek293 (RHO$^{WT}$-Rluc), respectively. For the HTS, Hek293 (RHO$^{P23H}$-Rluc) cells were incubated with each compound for 24 h before assayed for luciferase activity, and hits that showed activity scores lower than Mean-2SD were selected. For the counter screen, we tested the hits by repeating the luciferase reporter assay in the Hek293 (RHO$^{WT}$-Rluc) cells, and selected those that showed preferred clearance activity in the Hek293 (RHO$^{P23H}$-Rluc) versus the Hek293 (RHO$^{WT}$-Rluc) cells. B. A pie chart showing the compound libraries screened. The number of compounds in each library is shown in the bracket. UC, University of Cincinnati Diversity Set; LOPAC, Library of Pharmacologically Active Compounds; FDA, U.S. Food and Drug Administration approved drugs; MIPE, NCATS Mechanism Interrogation Plat E. C. An exemplary dose-response plot of a hit compound, CL-009 in the Hek293 (RHO$^{P23H}$-Rluc) and Hek293 (RHO$^{WT}$-Rluc) cells, as black squares and magenta circles, respectively. The luminescence was normalized by the mean luminescence of cells treated with 0.1% DMSO and 1 mM Evans Blue as the 0 and −100% controls, respectively. Data points and error bars are the means and SDs. N=3. Dose-response curves were fitted by the Origin Software using the Hills function. D. Rhodopsin dot blots of untreated NIH3T3 (Rho$^{WT}$/GFP) and NIH3T3 (Rho$^{P23H}$/GFP) cells cell lysates loaded at 25, 50, 75 and 100%. E. Rhodopsin dot blot intensities in D were measured by ImageJ and plotted in as a function of loaded cell lysate amount. N=3. F. Rhodopsin dot blots of NIH3T3 (Rho$^{P23H}$/GFP) and NIH3T3 (Rho$^{WT}$/GFP) cells (bottom) each treated with 0.1% DMSO or CL-001 to CL-009 at 10 μM for 24 h. Cells were loaded at the same amount as the 100% loading control in D. G. Rhodopsin dot blot intensities in F were plotted in as a box chart, respectively. The middle lines and upper/bottom lines of boxes in G are the means and SDs. N=3. P23H and WT rhodopsin levels in each repeat are shown as black squares and magenta circles, respectively. H. The chemical structures of CL-001 to CL-009. $EC_{50}$s shown in brackets were obtained from high-content image analyses quantifying the immunostaining of P23H rhodopsin in response to 8-10 doses of each hit compound.
Figure 1B:
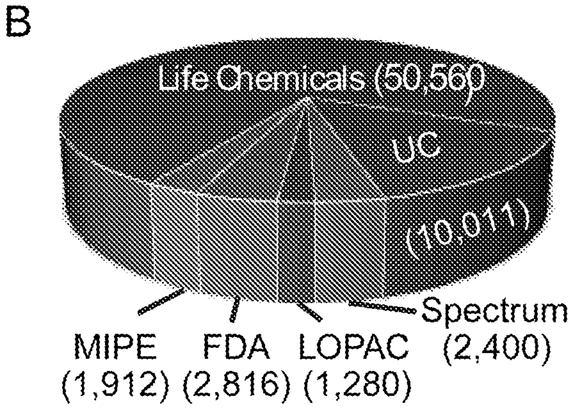
Figure 1C:
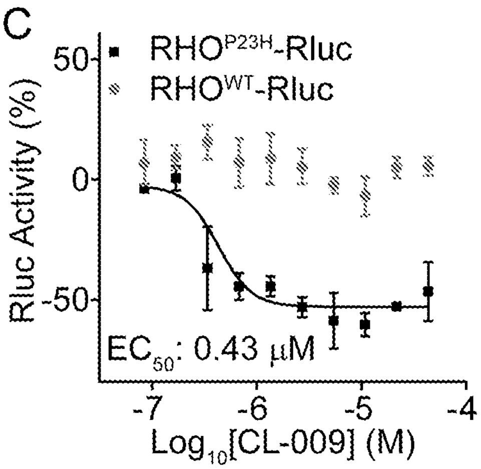
Figure 1D:
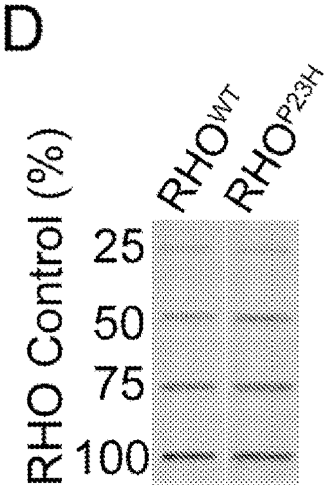
Figure 1E:
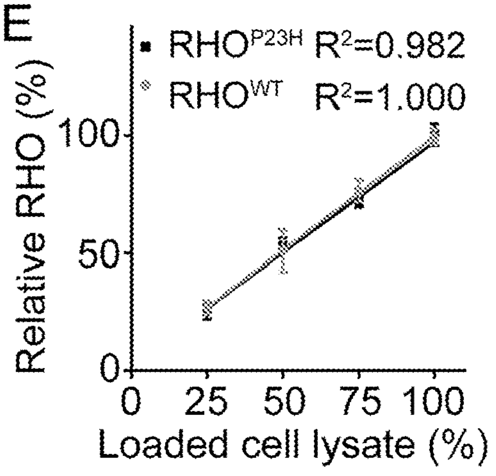
Figure 1F:
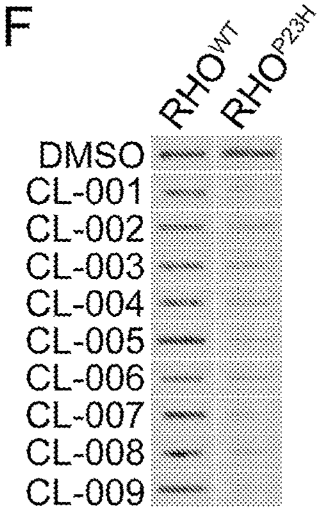
Figure 1G:
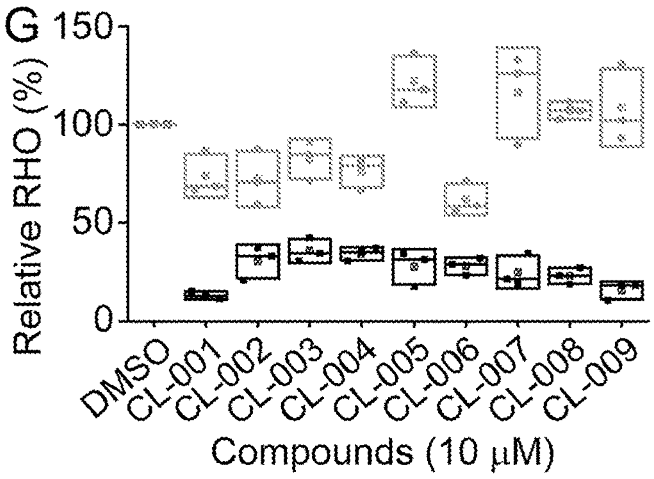

To identify small molecules that clear the misfolded P23H rhodopsin mutant protein, we developed a cell-based HTS assay using a Hek293 cell line stably expressing the bright Rluc as a reporter fused to P23H rhodopsin (Hek293 ($RHO^{P23H}$-Rluc), FIG. 1A and FIG. 8). Because a photoreceptor cell line is not available in culture, we selected one of the most commonly used Hek293 cells for HTS. Using this luciferase reporter assay to quantify P23H rhodopsin in response to 24 h of compound treatment, we conducted an HTS of 68,979 small molecules in a total of 6 compound collections (FIG. 1B, Table 4). We identified 2072 compounds with activity scores lower than the cutoff at mean-2SD (Table 1) tested at one dose (9.96 to 16.13 μM) from three compound collections, and 128 hits with $EC_{50<20}$ μM tested at 7-11 doses from the other three compound collections. In the hit selection process, we excluded those compounds that inhibited the recombinant Rluc activity, and we performed a counter screen to select only those not reducing luminescence on the wild type (WT) rhodopsin-expressing Hek293 ($RHO^{WT}$-Rluc) cells at 10 μM compound concentrations, suggesting these selected compounds selectively favored the clearance of the mutant rhodopsin. Then we tested the dose response effects of these compounds in the Hek293 ($RHO^{P23H}$-Rluc) and Hek293 ($RHO^{WT}$-Rluc) cells by the luciferase reporter assay, to measure the potency and efficacy of these compounds that selectively reduced the P23H rhodopsin (FIG. 1C). Together, 46 compounds with the mutant rhodopsin selectivity were confirmed from this HTS of 68,979 compounds.

Hit Validation Confirmed 9 Hits

Figure 1H:
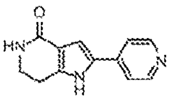
Figure 1H:
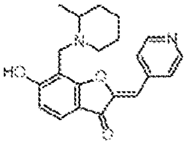
Figure 1H:
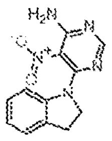
Figure 1H:
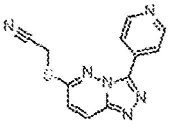
Figure 1H:
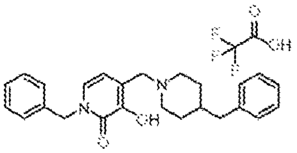
Figure 1H:
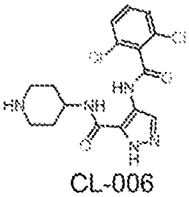
Figure 1H:
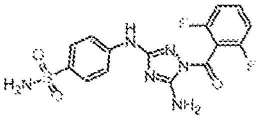
Figure 1H:
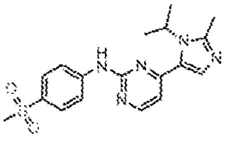
Figure 1H:
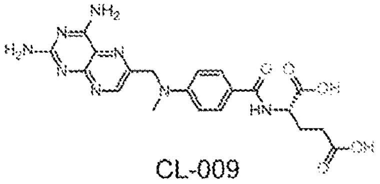
Figure 2A:
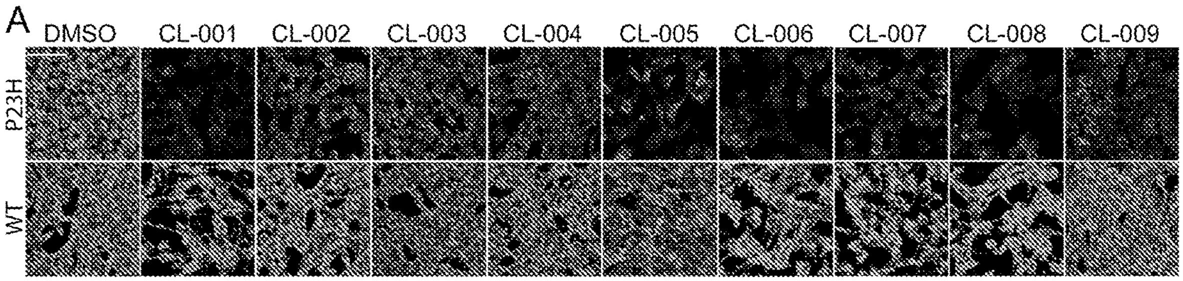
FIGS. 2(A-J) illustrate images and plots showing the high-content imaging assays validated nine hits that selectively reduced the P23H rhodopsin in vitro. For hit confirmation, we used the NIH3T3 cells that stably co-expressed GFP and P23H or WT rhodopsin, marked as NIH3T3 (RHO$^{P23H}$/GFP) or NIH3T3 (RHO$^{WT}$/GFP), respectively. A. High-content images of cells treated with 0.1% DMSO or CL-001 to CL-009 at 10 UM for 24 h. Immunostaining of rhodopsin showed that CL-001 to CL-009 selectively reduced the P23H but not the WT rhodopsin level. Scale bar, 50 μm. B-J. Dose-response curves of nine hit compounds by image-based analysis. Relative immunostaining intensity of rhodopsin measured from high-content images of NIH3T3 (RHO$^{P23H}$/GFP) and NIH3T3 (RHO$^{WT}$/GFP) cells each treated with DMSO or CL-001 to CL-009 at 8-10 doses for 24 h. The immunostaining intensity of rhodopsin per cell was normalized by DMSO treated cells as 0% and cells stained with secondary antibody only as −100%, respectively. Data and error bars are means and SDs. N=3. Dose-response curves were fitted by a modified Hill function. Chemical structure and $EC_{50}$ of each hit compound in the NIH3T3 (Rho$^{P23H}$/GFP) are shown in the inset of each graph.
Figure 2B:
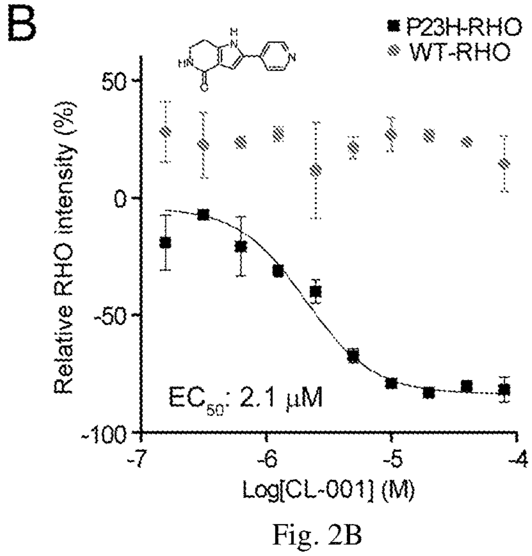
Figure 2C:
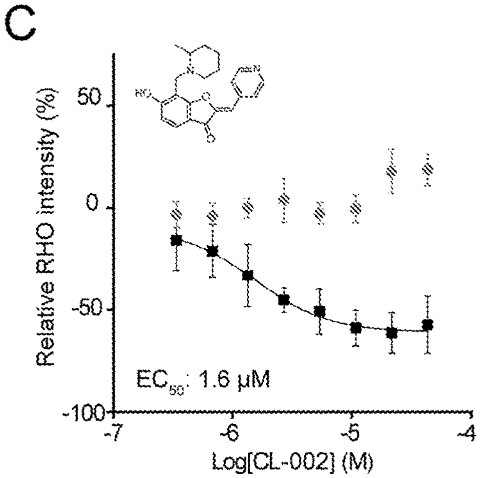
Figure 2D:
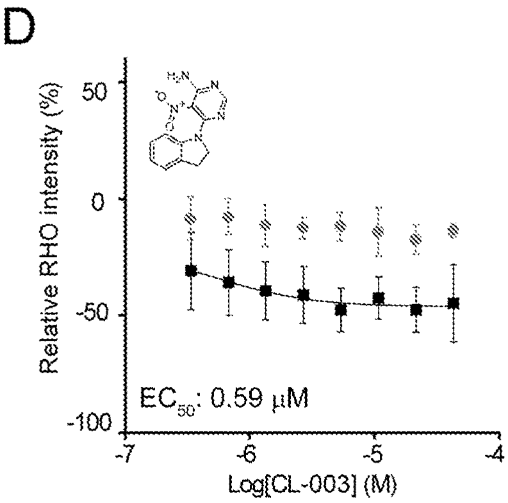
Figure 2E:
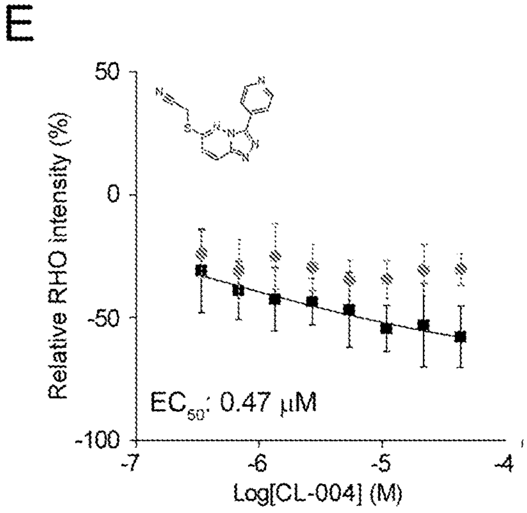
Figure 2F:
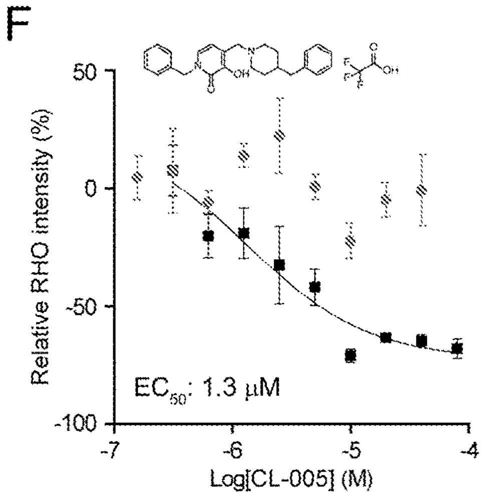
Figure 2G:
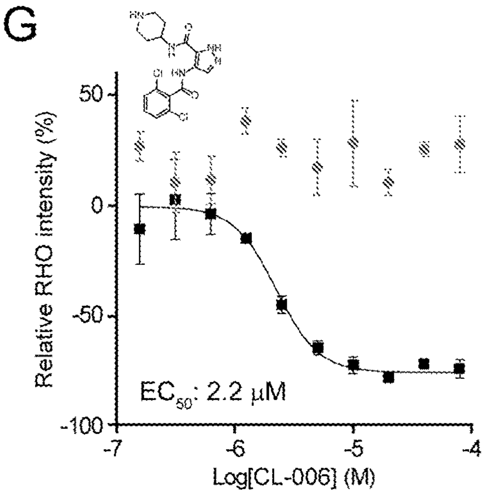
Figure 2H:
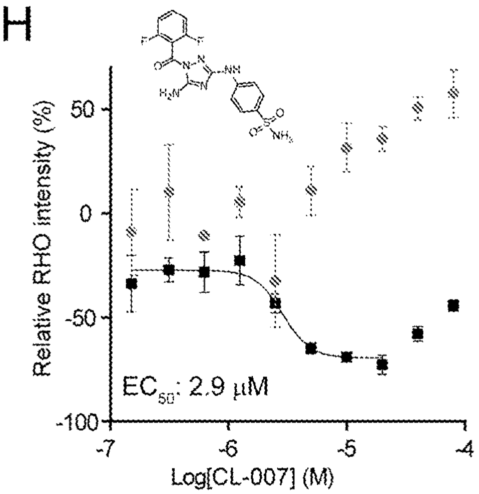
Figure 2I:
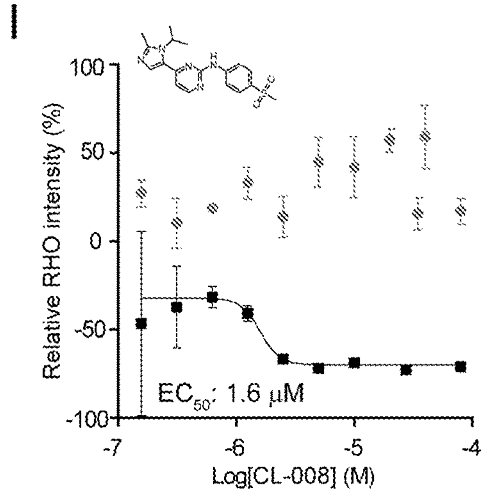
Figure 2J:
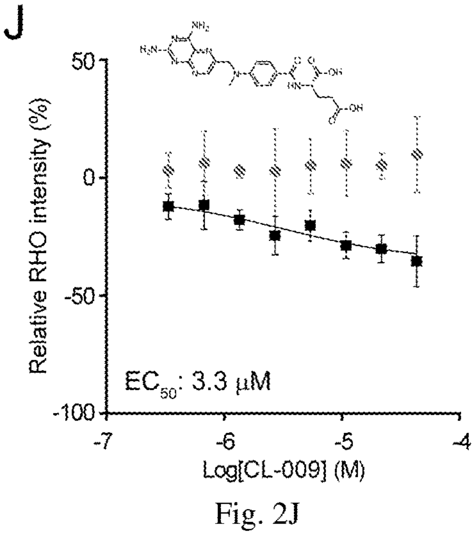

To eliminate the false positives related to cell lines or Rluc fusion and confirm the selective activity of 46 hits on clearance of P23H over WT rhodopsin, we tested these compounds in two NIH3T3 cell lines stably expressing the P23H rhodopsin (NIH3T3 ($RHO^{P23H}$/GFP)) and WT rhodopsin (NIH3T3 ($RHO^{WT}$/GFP)), respectively. We used a different cell line from the Hek293 that was used for HTS is to select compounds with activities that are not cell type specific. We also determined the rhodopsin levels using the dot blots of cell lysates from NIH3T3 ($RHO^{P23H}$/GFP) and NIH3T3 ($RHO^{WT}$/GFP) cells treated with 10 μM of each compound that showed a selective decrease of P23H compared to WT rhodopsin (FIGS. 1D-G and FIG. 9). We used high-content imaging analysis of rhodopsin immunofluorescence to quantify P23H and WT rhodopsin in these cells after 24 h treatment with these compounds (FIGS. 1H and 2). As a result, we validated 9 compounds that selectively cleared the misfolded P23H rhodopsin in mammalian cells (FIG. 1H and Table 2).

TABLE 2

Pharmacological activities of confirmed compounds that selectively clear P23H rhodopsin

| Hit name | PubChem CID | Libraries | Rluc assay Hek293 ($RHO^{P23H}$ – Rluc) EC$_{50}$ (μM) | Efficacy (%) | Rluc assay Hek293 ($RHO^{WT}$ – Rluc) EC$_{50}$ (μM) | Efficacy (%) | Image-based assay NIH3T3 ($RHO^{P23H}$/GFP) EC$_{50}$ (μM) | Efficacy (%) | Image-based assay NIH3T3 ($RHO^{WT}$/GFP) EC$_{50}$ (μM) | Efficacy (%) |
|---|---|---|---|---|---|---|---|---|---|---|
| CL-001 | 11715767 | MIPE | 1.1 | −69.4 | 1.0 | −44.3 | 2.1 | −83.6 | NA | NA |
| CL-002 | 6224422 | Life Chemicals | 2.0 | −86.1 | 3.4 | −62.0 | 1.6 | −61.0 | NA | NA |
| CL-003 | 4438424 | Life Chemicals | 0.89 | −65.3 | 1.5 | −37.7 | 0.60 | −46.1 | NA | NA |
| CL-004 | 6624030 | Life Chemicals | 1.6 | −68.6 | 0.92 | −45.5 | 0.47 | −70.7 | NA | NA |
| CL-005 | 10091681 | UC | 6.6 | −78.2 | 4.2 | −57.9 | 1.3 | −72.7 | NA | NA |
| CL-006 | 11338033 | MIPE | 1.7 | −66.2 | 1.52 | −42.9 | 2.2 | −76.4 | NA | NA |
| CL-007 | 5330790 | MIPE | 13 | −72.5 | 11 | −51.7 | 2.9 | −72.7 | NA | NA |
| CL-008 | 16747683 | MIPE | 0.93 | −89.5 | 0.59 | −52.7 | 1.6 | −70.1 | NA | NA |
| CL-009 | 126941 | Spectrum | 0.43 | −53.0 | NA | NA | 3.3 | −36.0 | NA | NA |

Chemoinformatics of the 9 Mutant Rhodopsin Selective Hits

Among the nine hits, only two compounds (CL-002 and CL-004) have no previously known pharmacological activities. Four of them (CL-001, CL-006, CL-007, and CL-008) were pan-cyclin-dependent kinase inhibitors (FIG. 1H). CL-003 has been documented with activities in numerous assays targeting different proteins including nucleotide binding oligomerization domain containing 1 (NOD1), NOD2, huntingtin, tumor necrosis factor α, glycogen synthase kinase 3 and so forth, and may be a pan-assay interference compound that non-selectively interacts with many targets. CL-005 is an inhibitor of the prolyl hydroxylase, as well as a stabilizer of heat shock-induced factor 1α, suggesting its activity in inducing hypoxia responses. CL-009, MTX, is an approved drug for the treatment of cancer and rheumatoid arthritis. However, the molecular mechanisms of action by which these compounds mediate P23H rhodopsin clearance require further investigation.

Figure 3A:
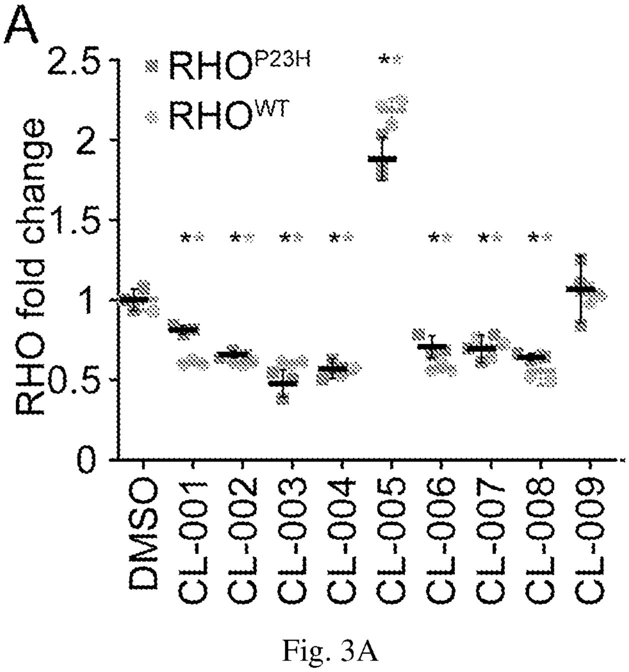
FIGS. 3(A-D) illustrate plots, schematics, and images showing the effect of active compounds on rhodopsin transcription, degradation, and clearance of other adRP causing mutants. A. Fold change of RHO transcripts in the NIH3T3 (RHO$^{P23H}$/GFP) and NIH3T3 (RHO$^{WT}$/GFP) cells treated with 10 μM of each hit compound compared to DMSO control. Q-PCR result of RHO transcript was firstly normalized by β-actin and then by the DMSO control. Middle lines and error bars are means and SDs of three biological replicates shown as data points. RHO$^{P23H}$ and RHO$^{WT}$. B. Illustration of the non-radioactive pulse-chase assay. Briefly, cells were starved in a Met-free medium for 1 h before pulsed in the azidohomoalanine (AHA) enriched medium that lacks Met for 4 h, so the nascent protein synthesized was labeled with AHA. Cells were then chased for 0-24 h in the medium containing 2 mM of Met, so the protein synthesized during the chase period was not labeled with AHA anymore. Next, via a "Click" reaction, the AHA incorporated proteins in the cell lysate were linked with biotin (BTN). Total rhodopsin was immunoprecipitated (IP) by the 1 D4 anti-rhodopsin antibody, and the BTN labeled rhodopsin was finally dot blotted (IB) with HRP-Streptavidin (SA). C. Percentage of nascent P23H rhodopsin from NIH3T3 (RHO$^{P23H}$/GFP) cell lysates IP with 1D4 anti-rhodopsin antibody (RHO) and IB with SA at 24 h of chase time. Cells were treated with 10 μM of CL-001 to CL-009, or DMSO at 0 h of chase time, respectively. The IB intensity of each dot was normalized by the DMSO control in the same membrane (FIG. 10). Three lines in each box represent the 75, 50 and 25% values of data in each group, and mean of each group was shown as filled diamonds, error bars were SDs. N=3. *, $p<0.05$; , $p<0.01$; and *, $p<0.001$ by an unpaired two-tail Student's t-test. D. Immunostaining images of rhodopsin in U2OS cells stably expressing the WT or six mutants of mouse rhodopsin (T4R, P23H, P53R, C110Y, D190N, P267L) that cause autosomal dominant retinitis pigmentosa, under treatment with 10 UM of CL-001, CL-002, CL-005 (11 μM), CL-007, and CL-009. Scale bar, 100 μm.

Effect of Nine Confirmed Compounds on Rhodopsin Transcription and Biodegradation We performed qPCR and a non-radioactive pulse-chase assay in NIH3T3 ($RHO^{P23H}$/GFP) and NIH3T3 ($RHO^{WT}$/GFP) cells treated with or without each hit compound for 24 h to determine whether the effect of selective clearance of P23H rhodopsin is due to either reduced biosynthesis or increased degradation of rhodopsin. The qPCR showed that both WT and P23H rhodopsin transcripts were reduced non-selectively by CL-001, CL-002, CL-003, CL-004, CL-006, CL-007 and CL-008, in comparison to DMSO control (FIG. 3A). Surprisingly, CL-005 increased rhodopsin transcripts in both NIH3T3 ($RHO^{P23H}$/GFP), and NIH3T3 ($RHO^{WT}$/GFP) cells up to 2-fold compared to DMSO control, whereas CL-009/MTX did not affect the transcription of both the WT and P23H rhodopsin.

Figure 3B:
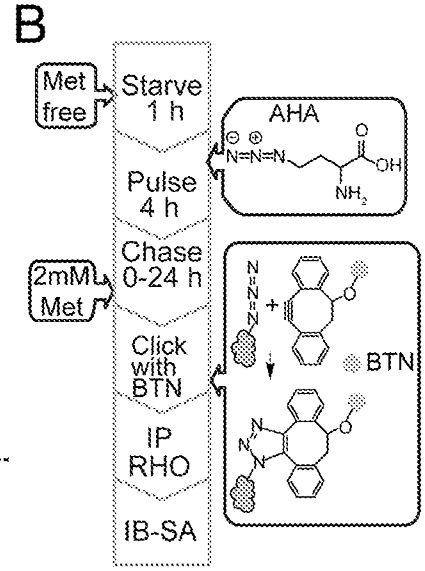
Figure 3C:
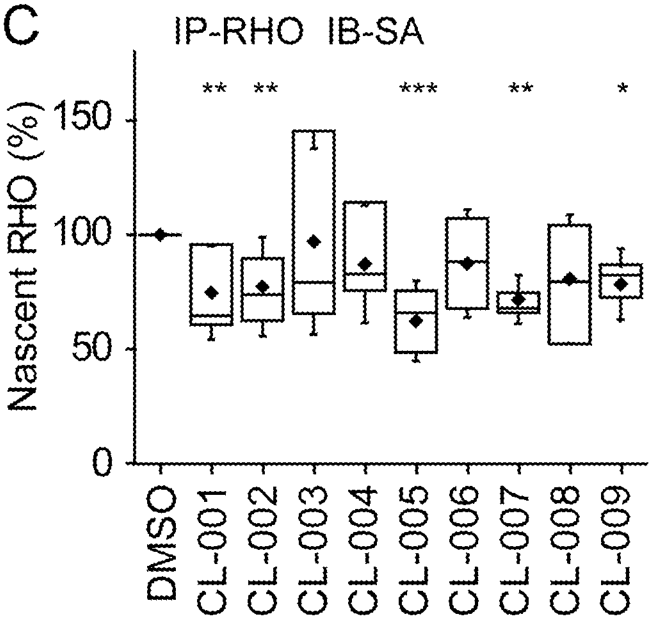
Figure 10A:
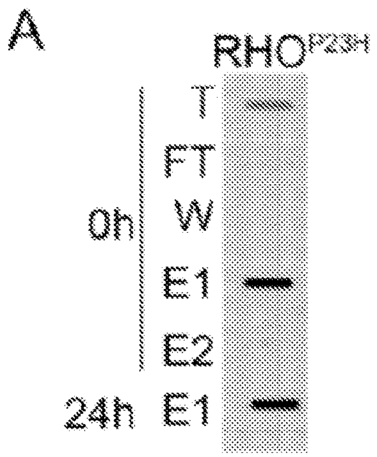
Figure 10B:
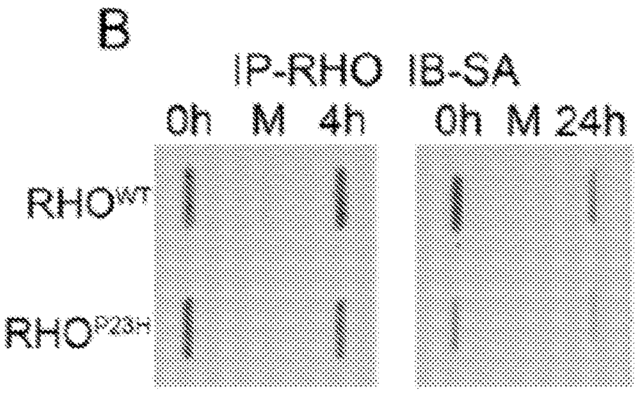
Figure 10C:
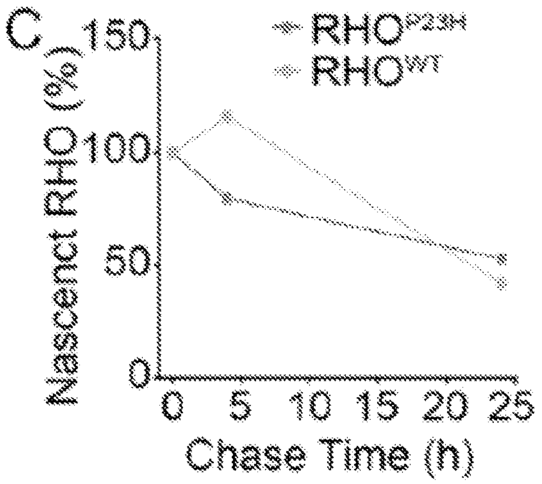
Figure 10D:
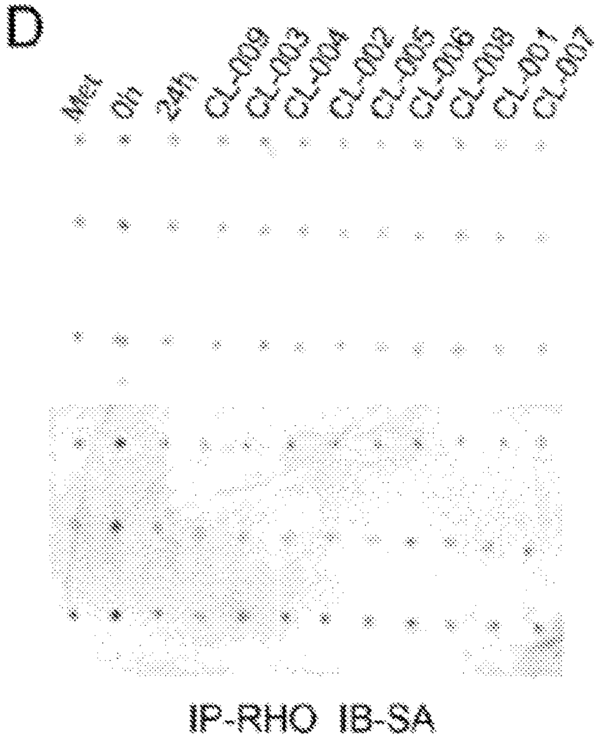
Figure 10E:
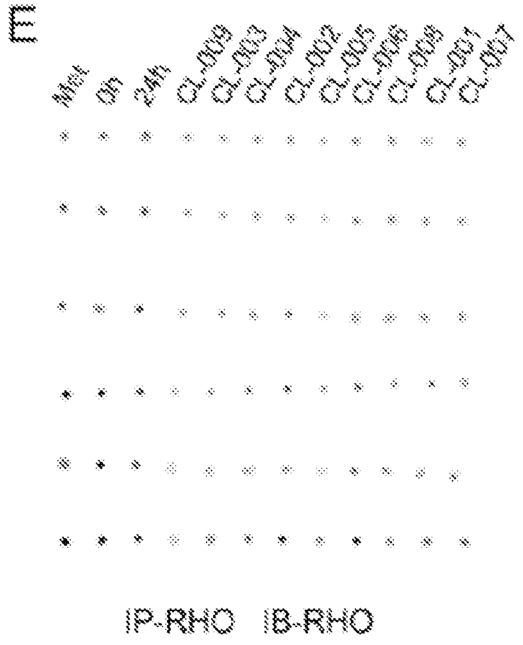
Figure 10F:
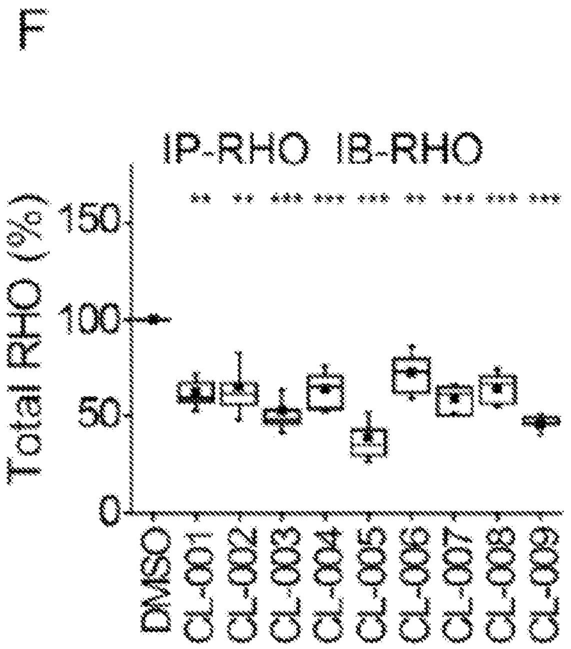
Figure 11A:
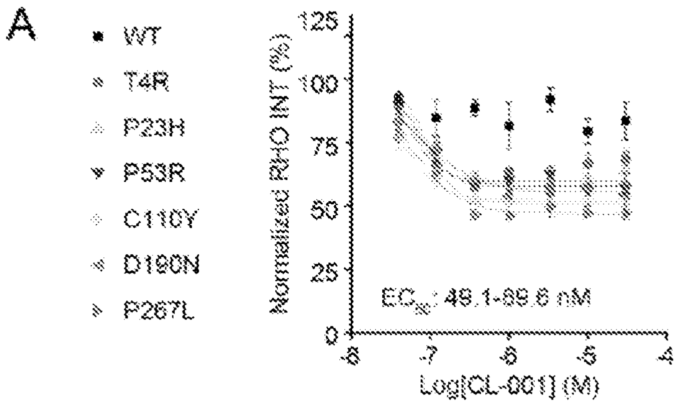
Figure 11B:
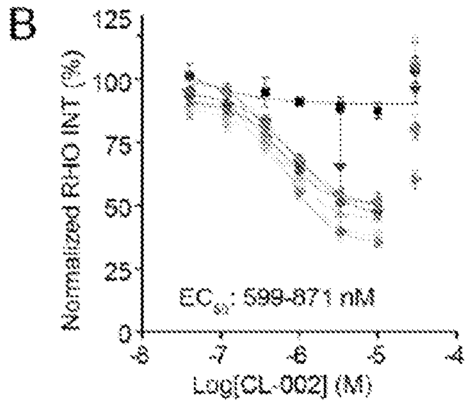
Figure 11C:
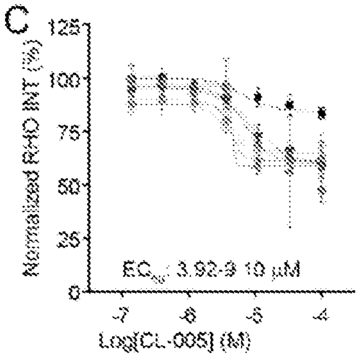
Figure 11D:
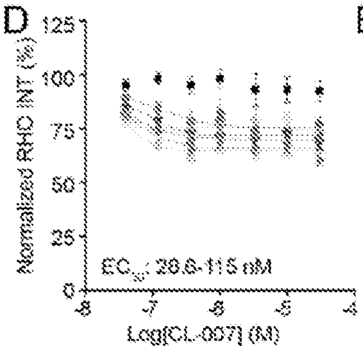
Figure 11E:
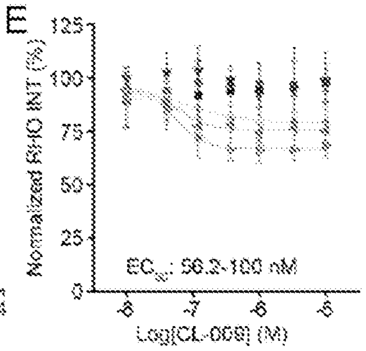
Figure 12A:
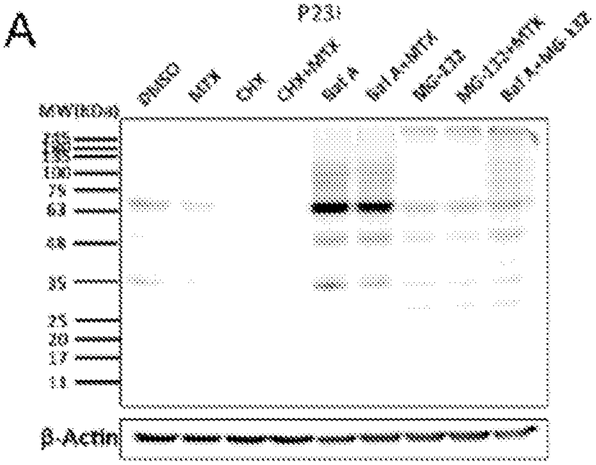
Figure 12B:
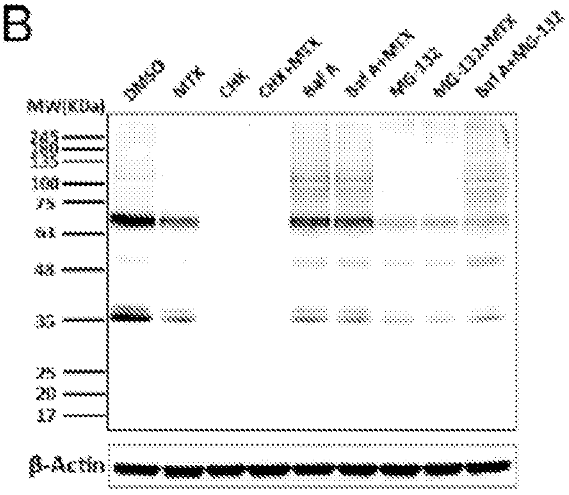
Figure 12C:
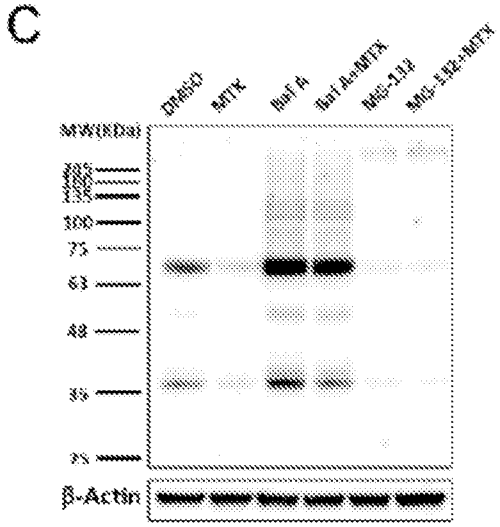
Figure 12D:
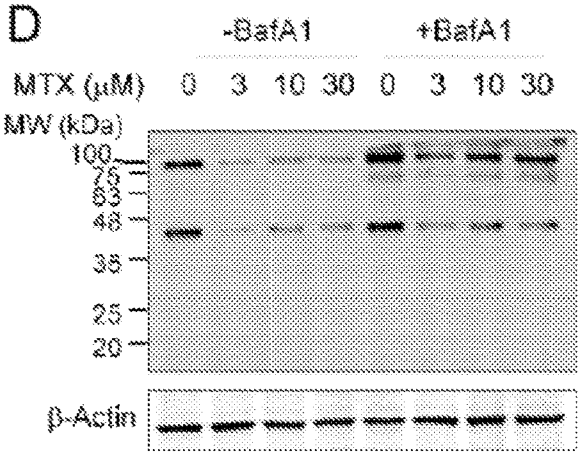
Figure 12E:
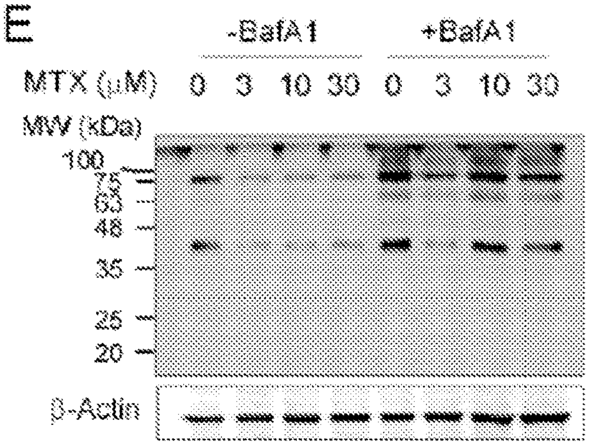
Figure 12F:
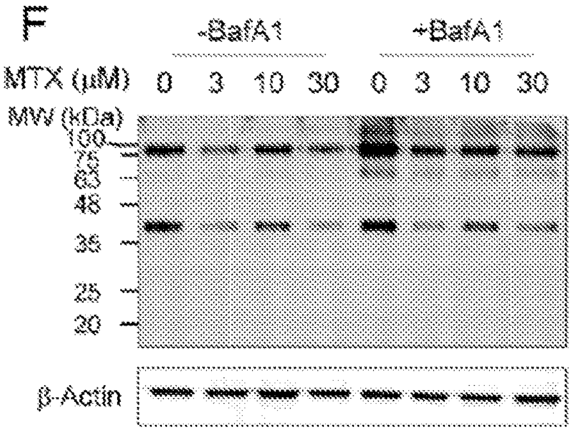
Figure 12G:
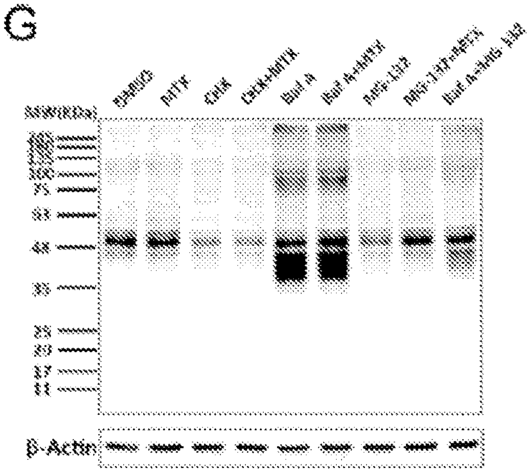
Figure 12H:
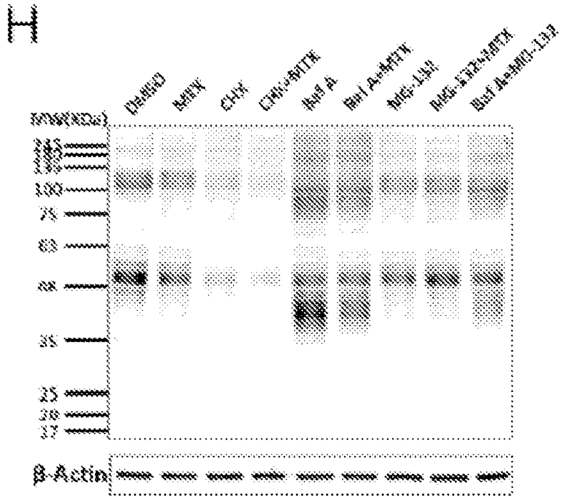
Figure 12I:
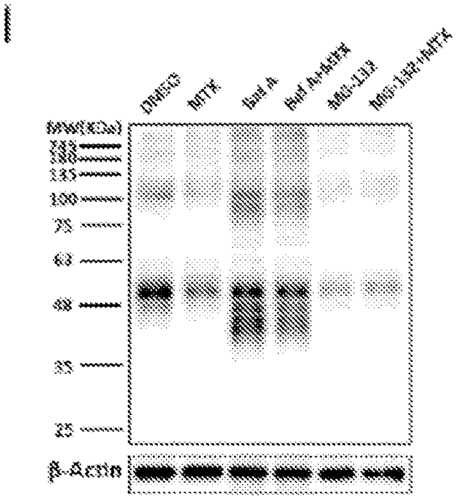
Figure 13C:
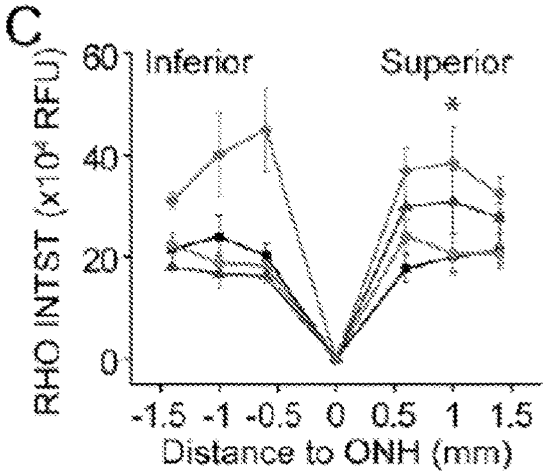
Figure 13D:
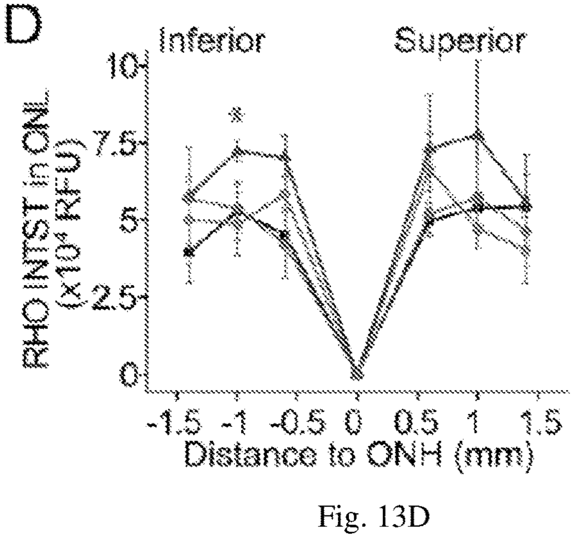
Figure 13E:
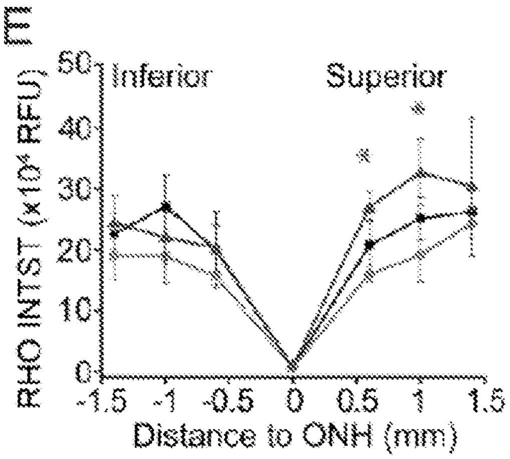
Figure 13F:
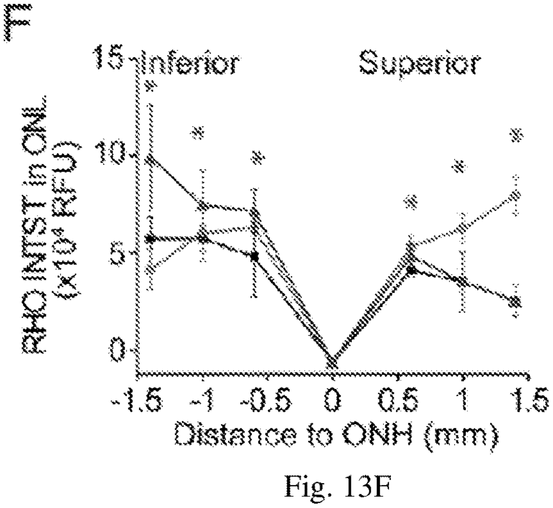

In the non-radioactive pulse-chase assay, we transiently labeled nascent proteins for 4 h by replacing methionine (Met) with AHA, an analogue of Met with an azide group in the side chain, in the culture medium of NIH3T3 ($RHO^{WT}$/GFP) and NIH3T3 ($RHO^{P23H}$/GFP) cells, followed by addition of Met back to the medium and chased for 24 h. The remaining AHA labeled rhodopsin was measured by attaching BTN to AHA incorporated proteins via a "Click" reaction, immunoprecipitating the cell lysate with 1D4 anti-rhodopsin antibody and dot blotted with SA (FIG. 3B). We found that the BTN-AHA labeled P23H rhodopsin was significantly reduced at 24 h of chase by treatment with 10 μM of CL-001, CL-002, CL-005, CL-007 and CL-009 (MTX), in comparison to DMSO control (FIG. 3C and FIG. 10). The total P23H rhodopsin pull-down level was decreased by all nine hits tested, confirming their previously validated activity (FIG. 10F). This result suggests only these five compounds (CL-001, CL-002, CL-005, CL-007 and CL-009/MTX) accelerated the degradation of the misfolded rhodopsin. Together, the results of rhodopsin dot blot, qPCR and pulse-chase assay showed that (Table 3) the hit compounds reduced the P23H rhodopsin by: 1) reducing rhodopsin transcription only (CL-003, CL-004, CL-006, and CL-008); 2) increasing its degradation only (CL-005 and CL-009); 3) or both decreasing transcription and increasing degradation of P23H rhodopsin (CL-001, CL-002, and CL-007). Because the transcription of rhodopsin in the stable cells is driven by the cytomegalovirus (CMV) promotor but not the rhodopsin promotor, thus the group 1) compounds were not included for further investigation in this study because they may not affect the P23H rhodopsin level in vivo. Only 5 compounds (CL-001, CL-002, CL-005, CL-007, and CL-009) remained for further study.

TABLE 3

Effect of nine confirmed compounds on transcription and degradation of rhodopsin

| Compounds name | Rho protein level (Dot blot) | Rho mRNA level (qPCR) | Rate of $Rho^{P23H}$ degradation (Pulse-chase) |
|---|---|---|---|
| CL-001 | Down | Down | Up |
| CL-002 | Down | Down | Up |
| CL-003 | Down | Down | No Change |
| CL-004 | Down | Down | No Change |
| CL-005 | Down | Up | Up |
| CL-006 | Down | Down | No Change |
| CL-007 | Down | Down | Up |
| CL-008 | Down | Down | No Change |
| CL-009 | Down | No Change | Up |

TABLE 4

The workflow of HTS and confirmation assays performed to each compound library

| Compound library | Assay | Cell line/enzyme | Tested Conc. (μM) | Number of compounds tested | Number of hits |
|---|---|---|---|---|---|
| 10K UC Collection, University of Cincinnati | Luciferase reporter assay, single dose | Hek293(RHO$^{P23H}$-Rluc) | 9.93 | 10,011 | 82 |
| | Luciferase reporter assay, single dose, triplicate | Hek293(RHO$^{P23H}$-Rluc) | 10 | 76 | 42 |
| | Rluc activity assay, single dose, triplicate | Recombinant Rluc | 10 | 76 | 37 |
| | Dot blot of rhodopsin, single dose, four replicates | NIH3T3(RHO$^{P23H}$/GFP) and NIH3T3(RHO$^{WT}$/GFP) | 10 | 37 | 4 |
| | Luciferase reporter assay, dose-response, triplicate | Hek293(RHO$^{P23H}$-Rluc) and Hek293(RHO$^{WT}$ Rluc) | 10 doses | 4 | 1 |
| | Image-based analysis, dose-response, triplicate | NIH3T3(RHO$^{P23H}$/GFP) and NIH3T3(RHO$^{WT}$/GFP) | 10 doses | 5 | 1 |
| | Western Blot of rhodopsin, single dose, triplicate | NIH3T3(RHO$^{P23H}$/GFP) and NIH3T3(RHO$^{WT}$/GFP) | 10 | 1 | 1 |
| Spectrum Collection, Case Western Reserve University | Luciferase reporter assay, single dose | Hek293(RHO$^{P23H}$-Rluc) | 12.99 | 2400 | 89 |
| | Luciferase reporter assay, single dose, triplicate | Hek293(RHO$^{P23H}$-Rluc) | 12.99 | 89 | 86 |
| | Cytotoxicity assay, single dose, triplicate | Hek293(RHO$^{P23H}$-Rluc) | | 86 | 19 |
| | Rluc activity assay, single dose, triplicate | Purified Rluc | 10 | 19 | 9 |
| | Luciferase reporter assay, dose-response, triplicate | Hek293(RHO$^{P23H}$-Rluc) and Hek293(RHO$^{WT}$-Rluc) | 10 doses | 19 | 3 |
| | Image-based analysis, dose-response, triplicate | NIH3T3(RHO$^{P23H}$/GFP) and NIH3T3(RHO$^{WT}$/GFP) | 10 doses | 5 | 2 |
| | Dot blot of rhodopsin, single dose, four replicates | NIH3T3(RHO$^{P23H}$/GFP) and NIH3T3(RHO$^{WT}$/GFP) | 10 | 2 | 2 |
| | Western Blot of rhodopsin, single dose, triplicate | NIH3T3(RHO$^{P23H}$/GFP) and NIH3T3(RHO$^{WT}$/GFP) | 10 | 2 | 1 |
| Life Chemicals 50K, collection, Case Western Reserve University | Luciferase reporter assay, single dose | Hek293(RHO$^{P23H}$-Rluc) | 16.13 | 50,560 | 1,901 |
| | Luciferase reporter assay, single dose, triplicate | Hek293(RHO$^{P23H}$-Rluc) and Hek293(RHO$^{WT}$-Rluc) | 16.13 | 842 | 38 |
| | Luciferase reporter assay, dose-response, triplicate | Hek293(RHO$^{P23H}$-Rluc) and Hek293(RHO$^{WT}$-Rluc) | 10 doses | 38 | 12 |
| | Image-based analysis, dose-response, triplicate | NIH3T3(RHO$^{P23H}$/GFP) and NIH3T3(RHO$^{WT}$/GFP) | 10 doses | 38 | 12 |
| | Dot blot of rhodopsin, single dose, four replicates | NIH3T3(RHO$^{P23H}$/GFP) and NIH3T3(RHO$^{WT}$/GFP) | 10 | 12 | 3 |
| | Western Blot of rhodopsin, single dose, triplicate | NIH3T3(RHO$^{P23H}$/GFP) and NIH3T3(RHO$^{WT}$/GFP) | 10 | 3 | 3 |
| FDA, LOPAC, and MIPE, NCATS | Luciferase reporter assay, dose-response, triplicate | Hek293(RHO$^{P23H}$-Rluc) and Hek293(RHO$^{WT}$-Rluc) | 7 or 11 doses | 6,008 | 34 |
| | Dot blot of rhodopsin, single dose, four replicates | NIH3T3(RHO$^{P23H}$/GFP) and NIH3T3(RHO$^{WT}$/GFP) | 10 | 34 | 4 |
| | Image-based analysis, dose-response, triplicate | NIH3T3(RHO$^{P23H}$/GFP) and NIH3T3(RHO$^{WT}$/GFP) | 10 doses | 4 | 4 |
| | Western Blot of rhodopsin, single dose, triplicate | NIH3T3(RHO$^{P23H}$/GFP) and NIH3T3(RHO$^{WT}$/GFP) | 10 | 4 | 4 |
| Final number of hits | | | | | 9 |

Figure 3D:
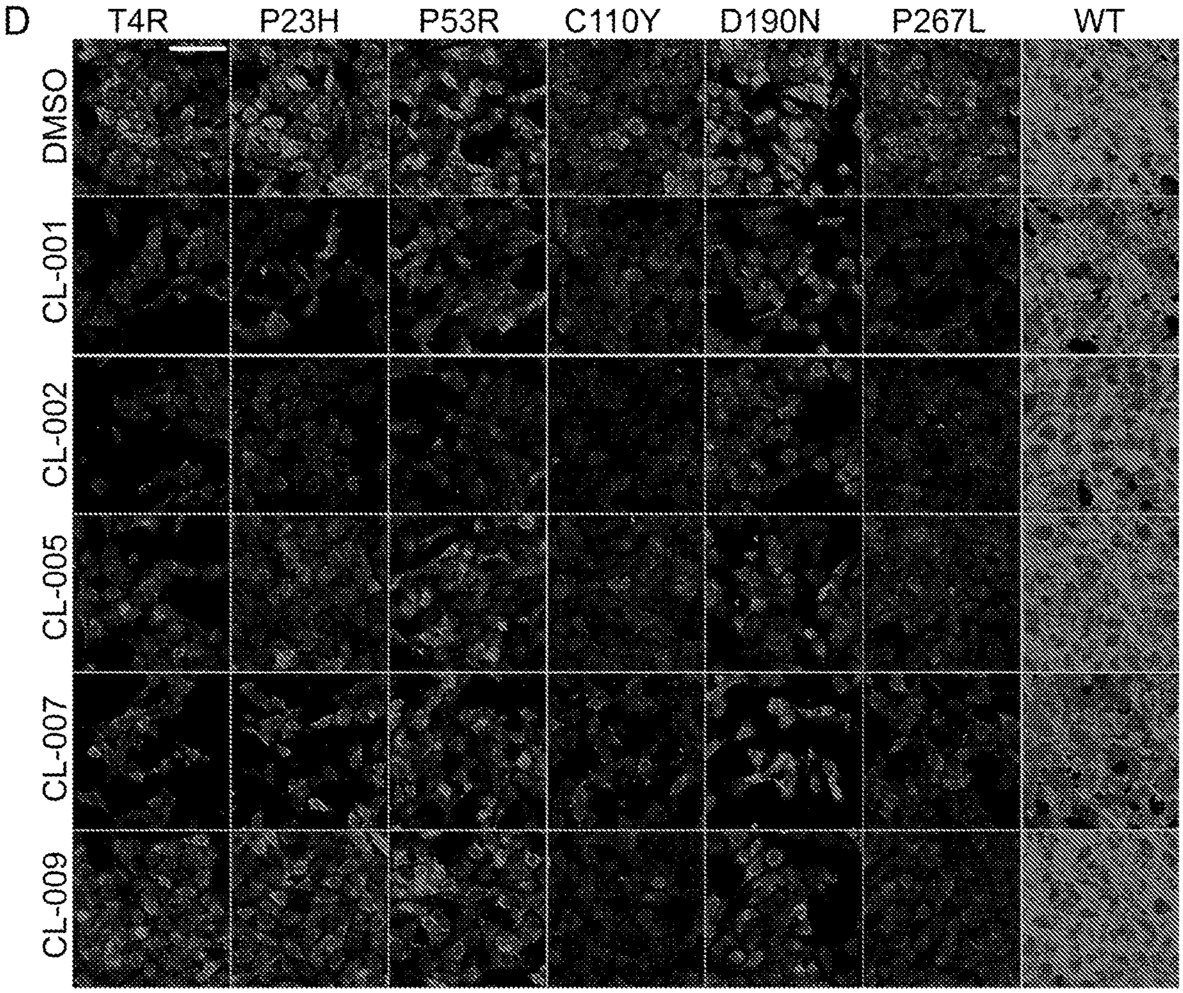

The Activity of Five Compounds on the Clearance of Other Misfolded Rhodopsin Mutants To determine whether these five confirmed compounds affect the clearance of other RP-causing rhodopsin mutants in vitro, we measured the protein levels of six adRP-causing rhodopsin mutants stably expressed in the U2OS cells (T4R, P23H, P53R, C110Y, D190N and P237L, FIG. 8) when they were treated with these compounds. These Class II mutants were previously reported to cause rhodopsin misfolding (www.hgmd.cf.ac.uk). The U2OS cells used here were previously used to quantify the effect of small molecule chaperones on rescuing rhodopsin transport. Using immunofluorescence and high-content imaging to quantify rhodopsin levels, we found that none of the five compounds affected the cellular localization of rhodopsin mutants, but the immunofluorescence intensities of these rhodopsin mutants were reduced by CL-001, CL-002, CL-005, and CL-007 (FIG. 3D and FIG. 11). CL-009 (MTX) treatment only showed dose-dependent reductions in cells expressing the P23H, C110Y, D190N and P267L mutants, but not the T4R and P53R mutants. The slightly different pharmacological activity of these compounds on P23H rhodopsin clearance in NIH3T3 (FIG. 2A) and U2OS cells (FIG. 3D) is due to the difference of cell type and expression level of P23H rhodopsin in the two stable cell lines. We then focused on CL-009 (MTX) for its mechanism of action and in-vivo efficacy studies because it is the only compound that accelerates mutant rhodopsin degradation without an effect on its transcription.

MTX Mediated P23H Rhodopsin Clearance Via the Lysosome but not Proteasome Pathway Rhodopsin is degraded via both the proteasome and the lysosome pathways. To determine which proteolytic pathway is involved in MTX mediated P23H rhodopsin clearance, we treated the NIH3T3 (RHO$^{P23H}$/GFP) and NIH3T3 (RHO$^{WT}$/GFP) cells with MTX plus either Bafilomycin A1 (BafA1), an ATPase inhibitor preventing lysosome acidification and activity, or MG-132, a proteasome inhibitor, and quantified the P23H or WT rhodopsin levels in these cells by immunoblots. We found only BafA1 but not MG-132 treatment abolished MTX induced P23H rhodopsin clearance, suggesting the lysosome rather than the proteasome pathway was involved in the MTX mediated P23H rhodopsin clearance (FIGS. 4A&B and FIG. 12)). BafA1 and MTX co-treatment also led to an accumulation of WT rhodopsin, whereas MG-132 plus MTX did not (FIGS. 4A&B), suggesting both WT and P23H rhodopsin are degraded mainly via the lysosome pathway in these NIH3T3 stable cells.

Figure 4C:
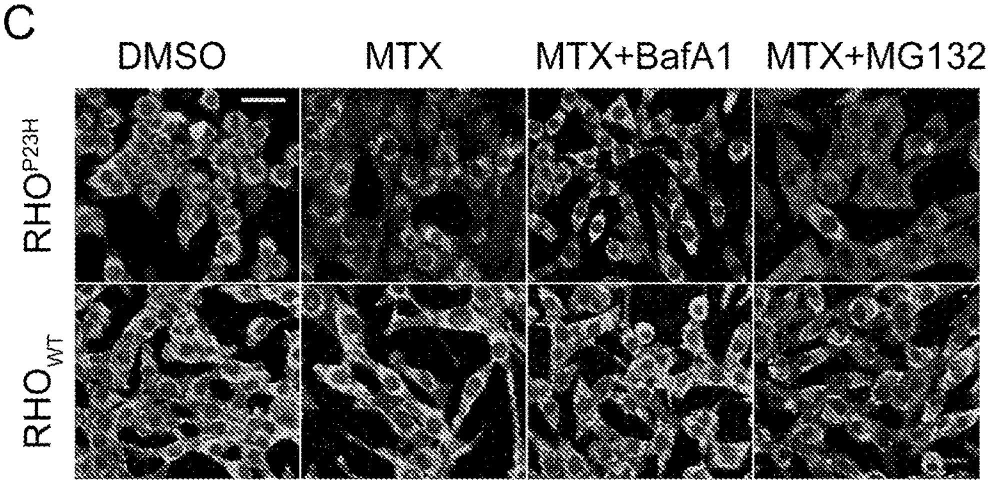
Figure 4D:
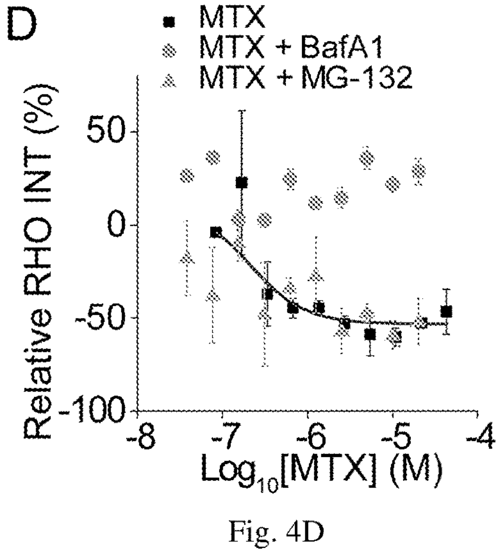
Figure 4E:
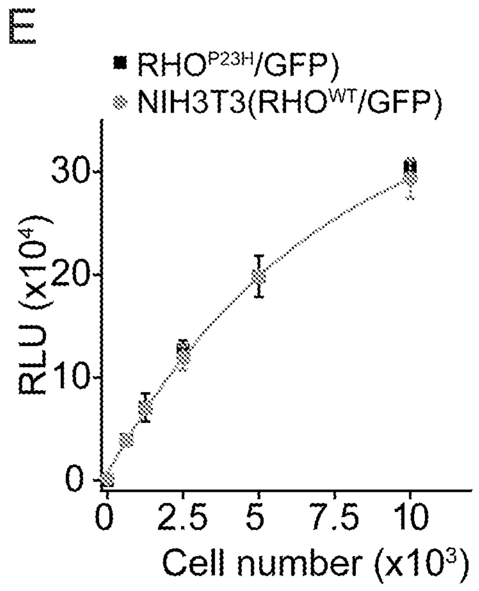
Figure 4F:
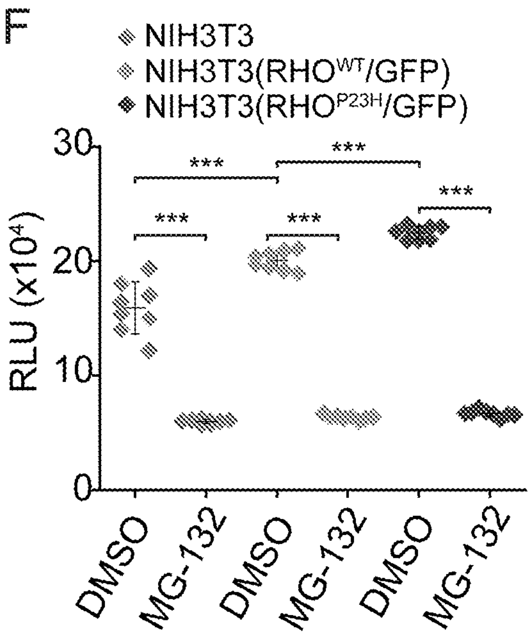
Figure 4G:
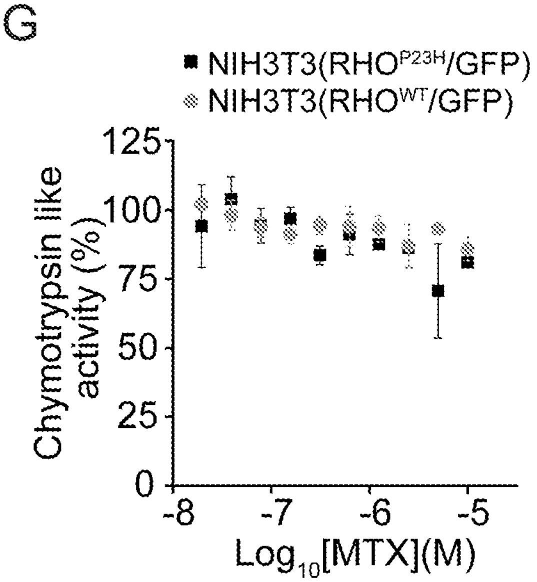

We repeated these treatments and quantified rhodopsin levels by immunofluorescence and high-content imaging (FIGS. 4C&D). We found that the mean intensity of P23H rhodopsin immunostaining per cell was reduced in an MTX dose-dependent manner, which was not affected by the addition of MG-132 but was entirely abolished by co-treatment with BafA1. This result confirmed the above immunoblots data that MTX selectively improved the degradation of P23H rhodopsin via the lysosome pathway.

We further found that MTX treatment did not affect chymotrypsin-like proteasome activity in the NIH3T3 ($RHO^{P23H}$/GFP) and NIH3T3 ($RHO^{WT}$/GFP) cells (FIG. 4E-G), confirming the conclusion that MTX did not affect the proteasome pathway.

MTX Increased Autophagy Flux In Vivo

Figure 5B:
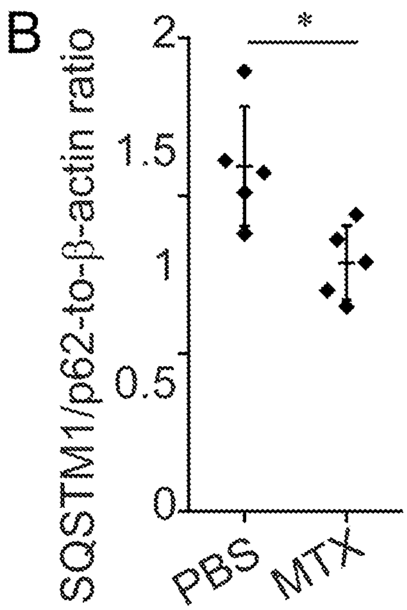
Figure 5C:
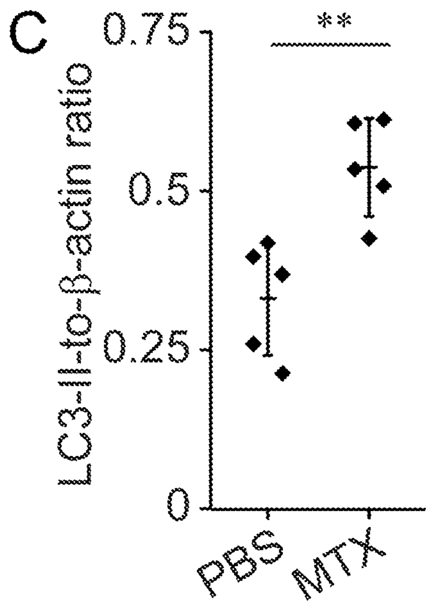
Figures 6K, 6L, 6M:
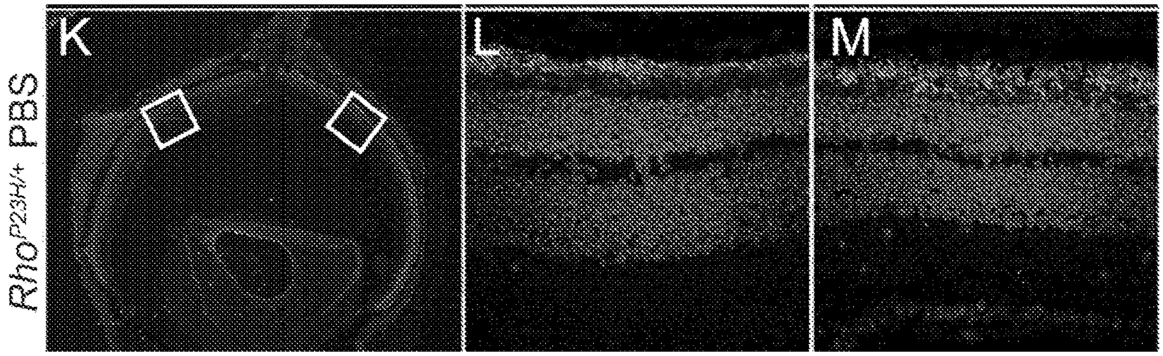
Figures 6N, 6O, 6P:
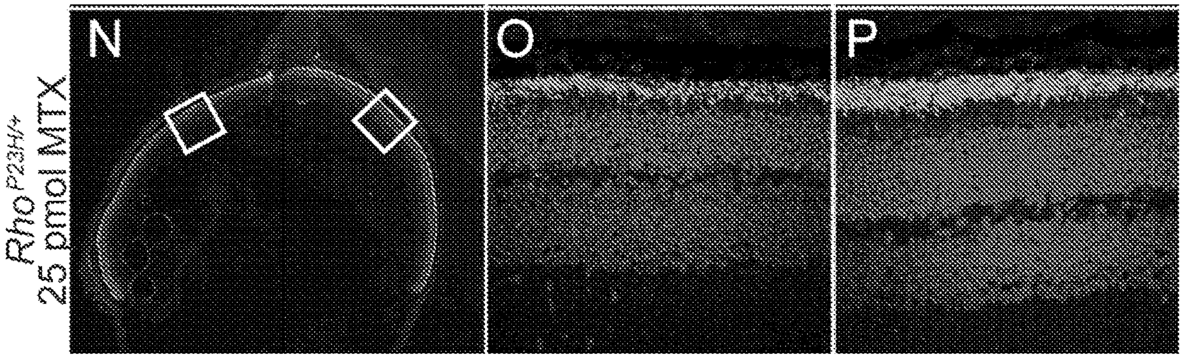
Figure 6Q:
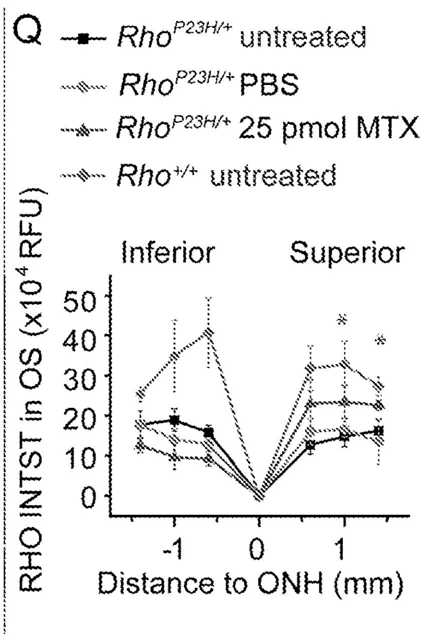
Figure 6R:
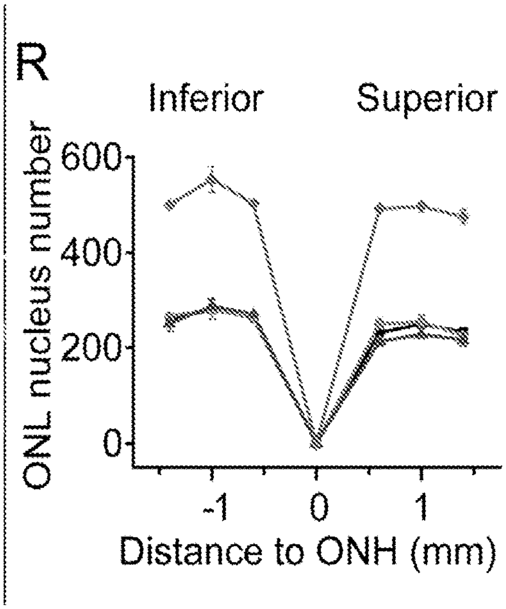
Figure 7A:
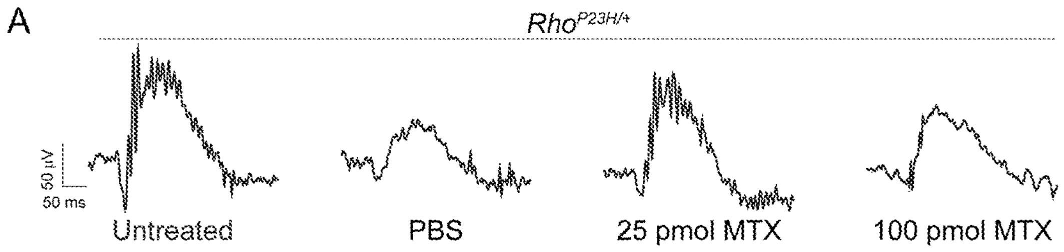
Figures 7B, 7C, 7D:
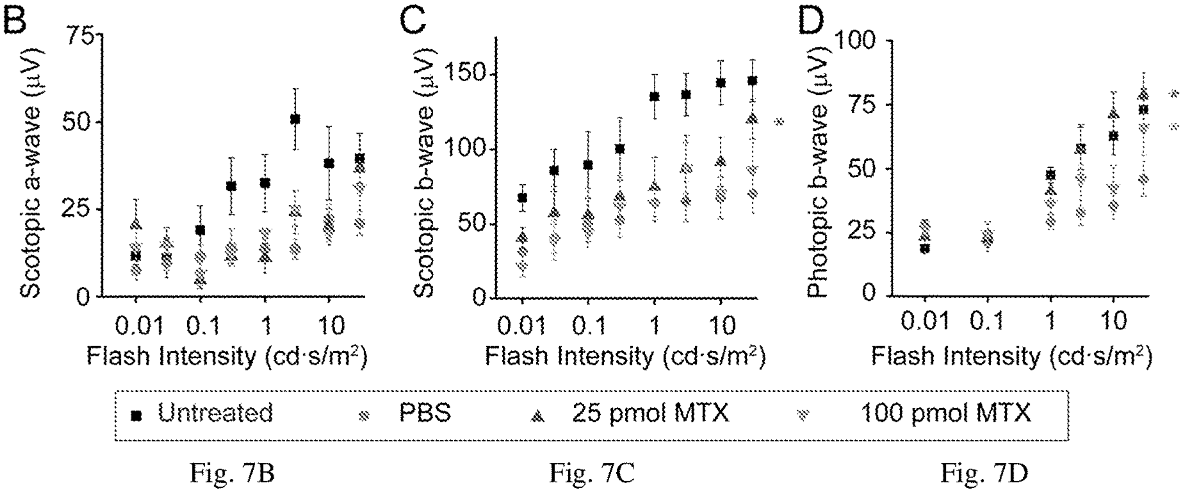
Figures 7E, 7F, 7G:
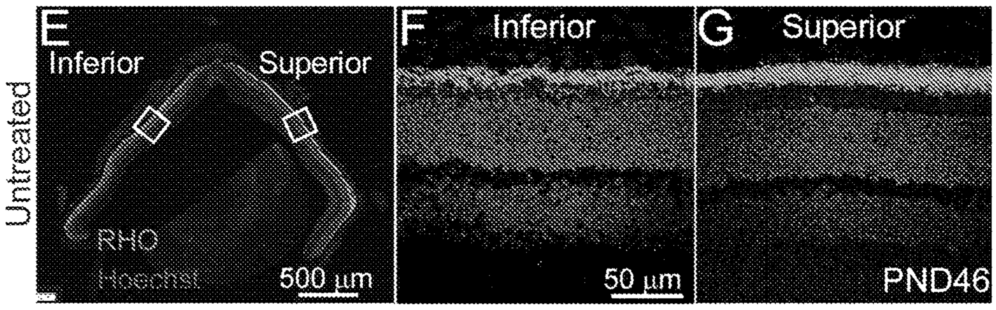
Figures 7H, 7I, 7J:
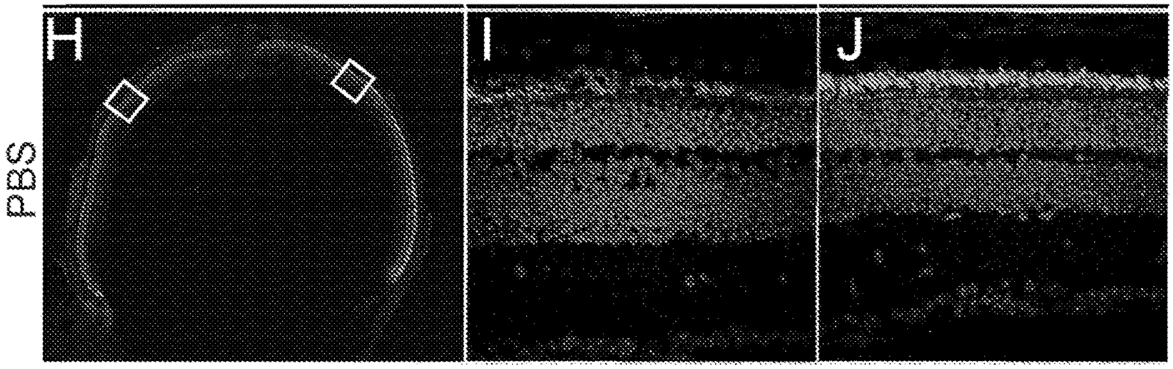
Figures 7K, 7L, 7M:
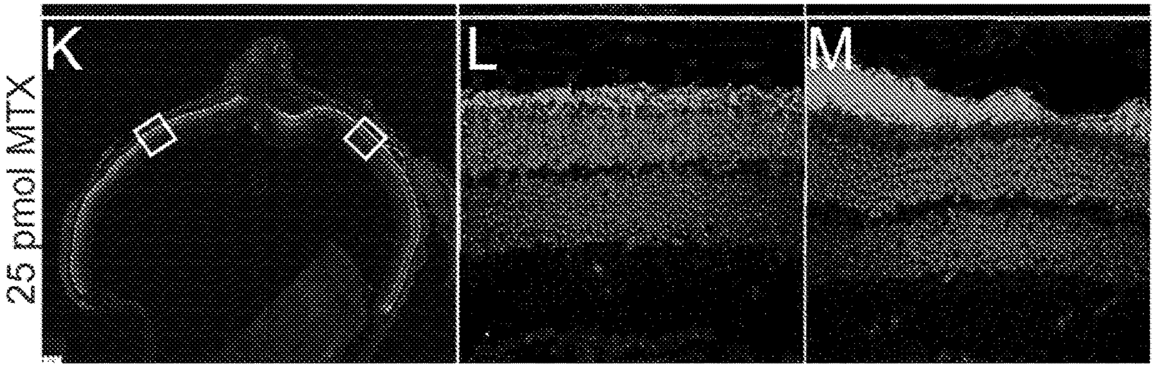
Figure 7N:
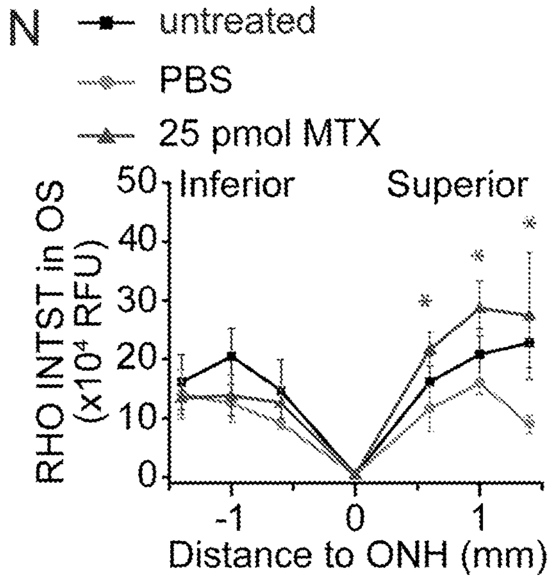
Figure 7O:
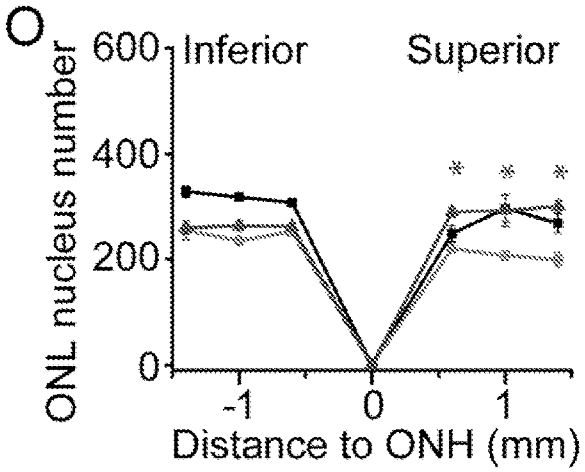
Figure 8A:
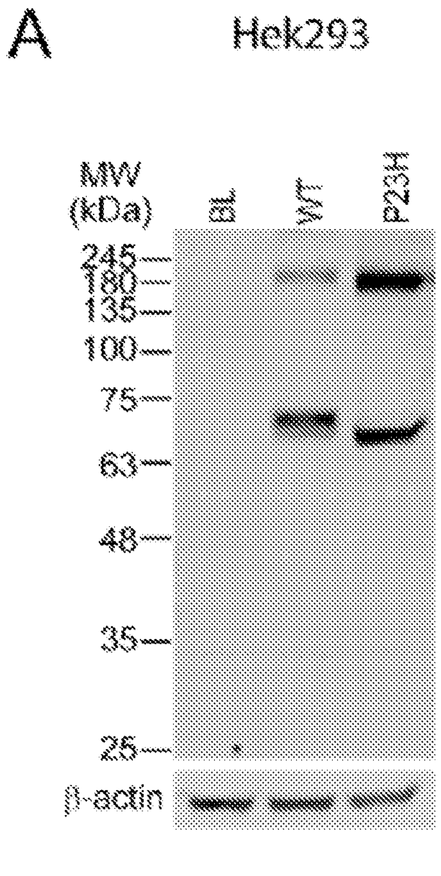
Figure 8B:
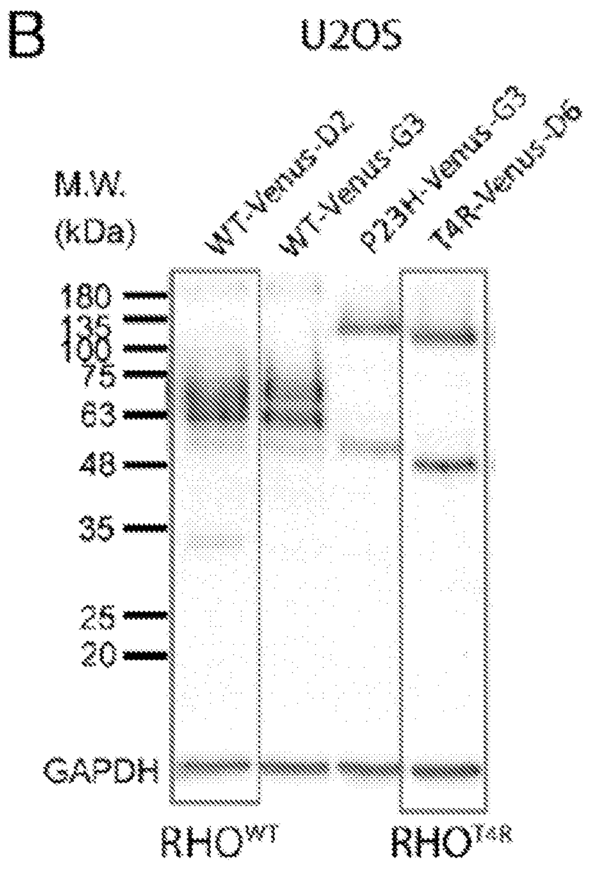
Figure 8C:
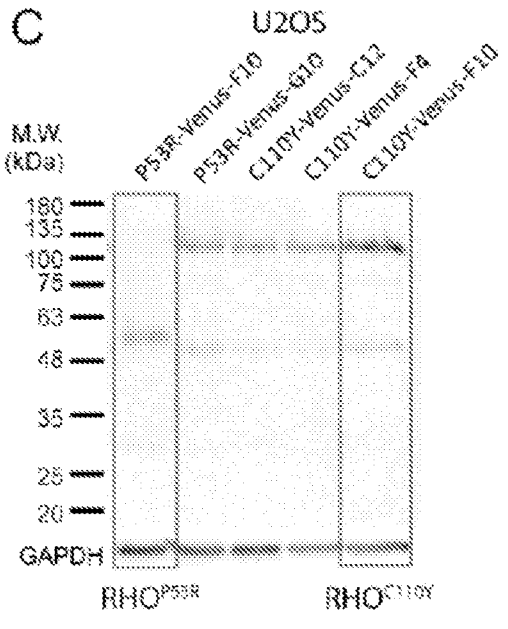
Figure 8D:
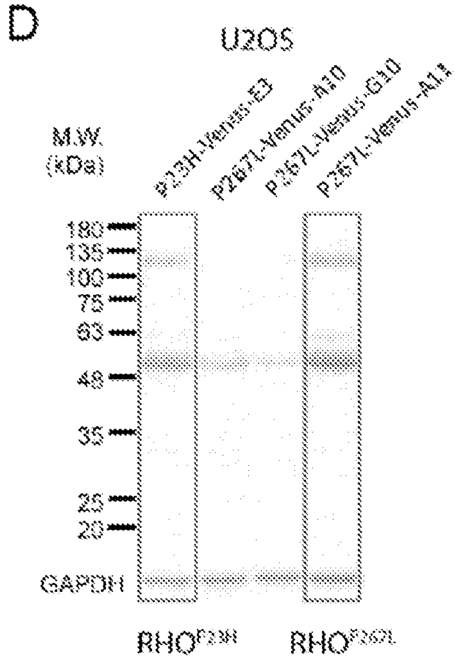
Figure 8E:
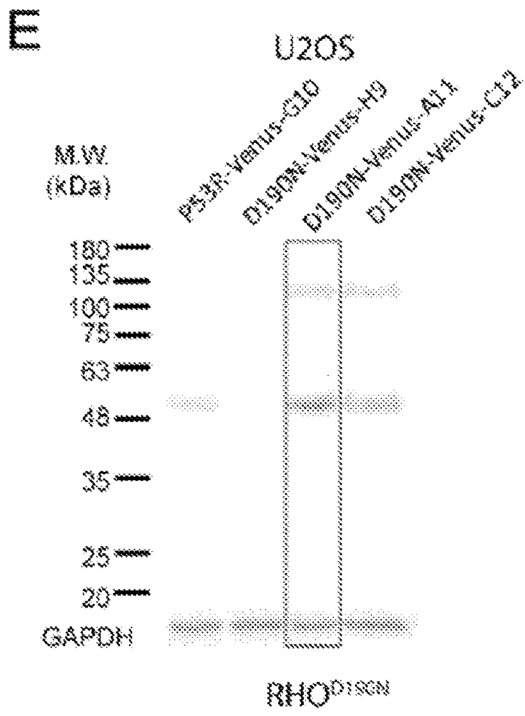
Figure 9A:
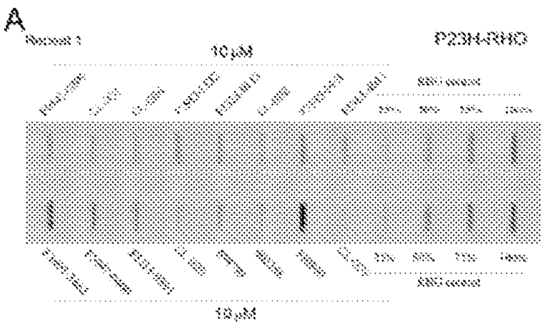
Figure 9B:
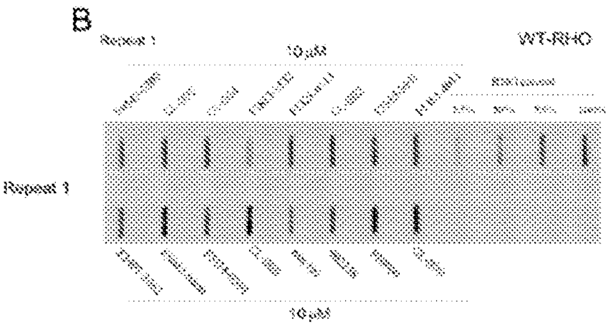
Figure 9C:
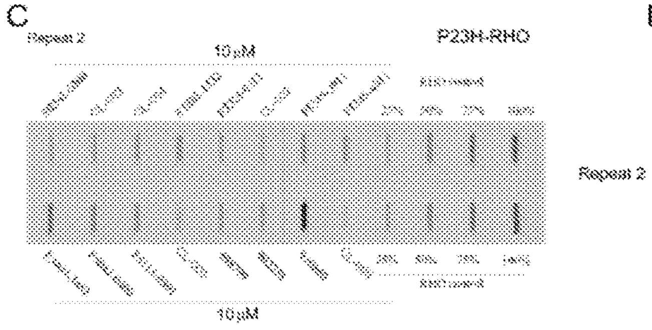
Figure 9D:
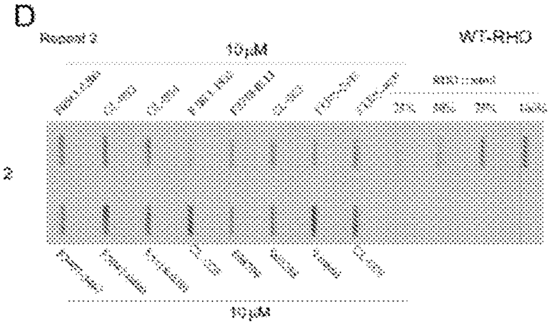
Figure 9E:
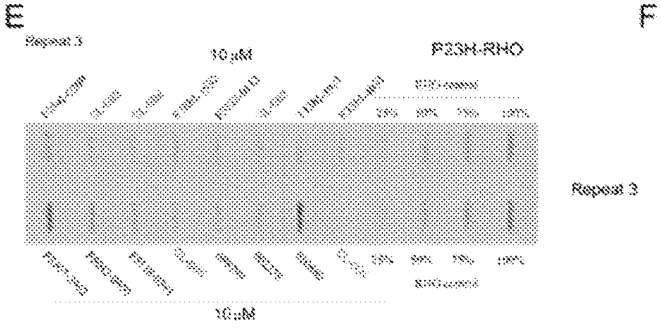
Figure 9F:
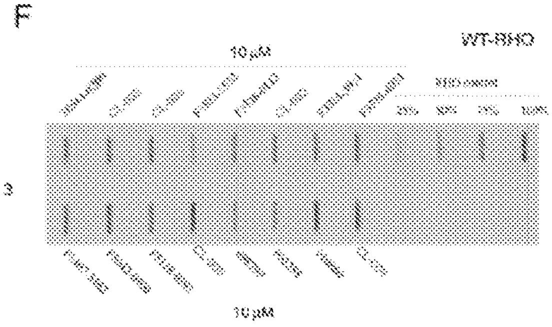
Figure 9G:
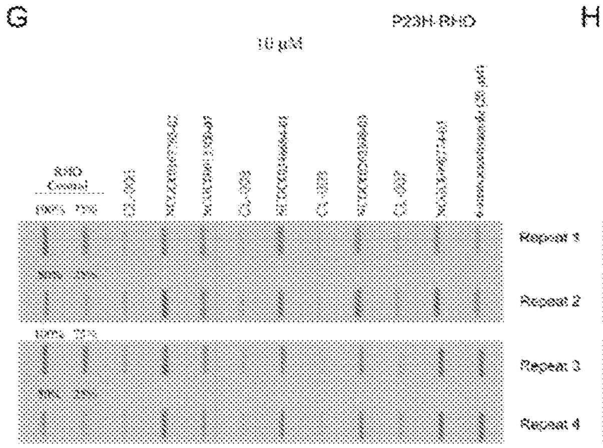
Figure 9H:
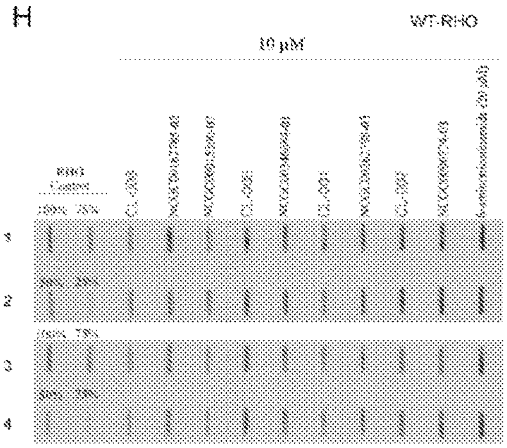

Because autophagy is known to regulate the clearance of protein aggregates via lysosomal activity, we then asked whether MTX treatment affects autophagy in $Rho^{P23H/+}$ knock-in mice, a commonly used animal model of RP. We administered 25 pmol of MTX by an IVI to one eye at PND 15 and an equal volume of PBS as vehicle control in the other eye. To determine whether autophagy flux was affected by MTX, we immunoblotted the LC3 and SQSTM1/p62 in the retinae after 48 h of treatments (FIG. 5). LC3-II is the lipidated form of LC3 that is incorporated in the autophagosomes, and SQSTM1/p62 is a known cargo of autophagy flux. Compared to PBS control, MTX treatment led to a decrease of SQSTM1/p62 level (FIG. 5B) and an increase of LC3-II (FIG. 5C), suggesting MTX increased autophagy flux in vivo.

One IVI of MTX Increased ERG Response and Retinal Rhodopsin Level in the $Rho^{P23H/+}$ Mice Photoreceptors of the $Rho^{P23H/+}$ mice undergo a period of fast degeneration from PND 15 to one month of age, and they die at a slower rate afterward. We tested the effect of MTX treatment on the retinal function and structure during the fast phase of retinal degeneration in the $Rho^{P23H/+}$ mice. We administered 25 or 100 pmol of MTX to one eye of these mice at PND 15 by an IVI and an equal volume of PBS as vehicle control in the other eye, and recorded scotopic and photopic full-field ERGs of these mice at PND 32. These two doses were estimated based on the volume of the mouse eyeball, and efficacious concentration of MTX in vitro. Exemplary scotopic ERG responses at 10 $cd \cdot s/m^2$ showed that the a- and b-waves of 25 pmol MTX-treated $Rho^{P23H/+}$ mouse eyes were higher than the PBS and non-treated groups (FIG. 6A). Multi-flash scotopic ERG measurements confirmed that both a- and b-waves of 25 pmol MTX-treated $Rho^{P23H/+}$ eyes were significantly higher than the PBS or non-treated eyes, whereas 100 pmol MTX-treated eyes showed no effect (FIGS. 6B&C). The 25 pmol MTX-treated $Rho^{P23H/+}$ eyes also showed higher photopic ERG responses than PBS treated or non-treated eyes (FIG. 6D), but the 100 pmol of MTX did not show any effects. The ratio of scotopic and photopic b- to a-wave amplitudes were not affected by MTX treatment, suggesting the functional increase of b waves by 25 pmol MTX was mainly due to the increased photoreceptor function, but not the independently increased bipolar cell responses (FIG. 13A-B). The PBS-treated group showed no difference in scotopic or photopic responses to the non-treated group, suggesting that a single IVI was safe and did not affect visual function.

To examine the retinal structure and rhodopsin homeostasis, we immunostained the retinal cryosection from these treated mice (euthanized at PND 33) with the anti-rhodopsin antibody labeling the OS, and Hoechst33342 for nucleus staining. As previously reported, the non-treated $Rho^{P23H/+}$ retina at PND 33 showed significantly shorter OS layer, reduced rhodopsin level and about half of nucleus number in the ONL compared to $Rho^{+/+}$ retina, supporting that rhodopsin homeostasis was disrupted and retinal degeneration occurred in the $Rho^{P23H/+}$ mice at one month of age (FIG. 6E-J&Q-R and FIGS. 13C-D & 14). The 25 pmol MTX-treated $Rho^{P23H/+}$ retinae showed a significant increase in the total rhodopsin level and rhodopsin in the OS, compared to PBS control on the superior side, but not the inferior side (FIGS. 6K-Q, and FIGS. 13C-D & 14). No change in ONL nucleus number was seen on either side of the $Rho^{P23H/+}$ retina by treatment of MTX (FIG. 6R), suggesting one IVI of 25 pmol MTX may not be sufficient to protect the $Rho^{P23H/+}$ mice from the fast period of retinal degeneration. PBS-treated retinae showed no difference in total rhodopsin level or localization, nor the ONL nucleus number, compared to untreated $Rho^{P23H/+}$ retinae, confirming that one IVI itself is safe and does not change retinal morphology (FIG. 6H-M&Q-R and FIG. 13C-D). Combining the ERG and IHC results, we conclude that a single IVI of 25 pmol MTX improved ERG responses in the $Rho^{P23H/+}$ eyes by increasing the functional rhodopsin level on the superior side of the retina that was not due to increased number of rod photoreceptors.

Multiple IVIs of MTX Increased ERG Response and Rhodopsin Level as Well as Photoreceptor Cell Numbers in the $Rho^{P23H}$+ Mice We then asked whether multiple administrations of MTX improved its efficacy in restoring rhodopsin homeostasis and preserving photoreceptors in the $Rho^{P23H/+}$ mice (FIG. 7). Thus, we performed four weekly IVIs of MTX to the $Rho^{P23H/+}$ mouse eyes starting at PND 15, followed by ERG recordings at PND 44 and euthanasia of the animals at PND 46 for IHC. The multi-flash scotopic and photopic b-waves of the MTX treated eyes were significantly increased compared to PBS control group (FIG. 7A-D). Photopic b-waves of 100 pmol MTX-treated $Rho^{P23H/+}$ eyes were also higher than the PBS group at higher flash intensities, even though they were not as high as the 25 pmol MTX group (FIG. 7D). The ERG recordings showed that multiple IVIs of MTX improved visual function compared to vehicle control. However, weekly IVIs of the vehicle showed reduction of both scotopic and photopic responses compared to untreated control (FIG. 7A-D), suggesting the weekly IVIs compromised the visual function of $Rho^{P23H/+}$ mice.

The IHC of $Rho^{P23H/+}$ retinae treated with four IVIs of 25 pmol MTX showed significantly higher levels of rhodopsin in the OS, lower level of rhodopsin in the ONL, and higher number of nucleus number in the ONL, on the superior side, but not the inferior side, in comparison to the PBS group (FIGS. 7E-O and FIGS. 13E-F & 15D). The results suggested that four IVIs of 25 pmol MTX increased folded rhodopsin in the OS and decreased mislocalized rhodopsin in the ONL on the superior side of the retina, even though we cannot distinguish the WT rhodopsin from the mutant. Compared to one injection of 25 pmol MTX, we found four weekly IVIs of MTX showed higher efficacy in retina protection, which preserved more ONL nucleus number on the superior side compared to the PBS group, but one MTX injection did not. However, four weekly IVIs of PBS showed reduced total rhodopsin level and lower nucleus number in the ONL of the $Rho^{P23H/+}$ retinae, compared to untreated control, confirming an adverse side effect by the multiple weekly IVIs that is also seen in the ERG responses (FIGS. 7E-J & N-O). Future optimization of IVI intervals or change in the treatment route is needed for long-term MTX treatment.

Therapeutic strategies for RP at different stages are different, depending on the surviving photoreceptor number at the time of intervention. To restore vision for the late-stage RP, many efforts have been devoted to varieties of techniques including stem cell therapies, optogenetics, and retina prosthetic developments to re-build visual responses in the retinae where most photoreceptors are gone. Gene therapy has made a substantial breakthrough for treating autosomal recessive blindness mainly by delivery of the functional gene locally that is lost due to genetic mutations when retinal structures are still largely maintained. Alternatively, gene delivery of neurotrophic factors by adeno-associated virus such as ciliary neurotrophic factor and cone-rod derived neurotrophic factor showed protective effects that delayed rod and cone death in animal models of RP, respectively. In complementation to gene therapy, we are looking for pharmacological interventions targeting the early events in the rods before they die, so that the retinal structure and function can be preserved, and vision can be maintained at the early- or mid-stages of RP. Specifically, we are targeting adRP, where rod death is not due to insufficiency of a gene's function, but rather the dominant-negative effect of the mutated gene, such as RHO. Thus, the goal of this study is to develop preventive therapies targeting the early- and mid-stages of adRP caused by misfolded rhodopsin. Importantly, we discovered a novel activity of MTX, an FDA-approved drug, that upregulated misfolded rhodopsin degradation and improved visual function, preserved retinal structure from the fast period of retinal degeneration in the animal model of RP. Potentially, this misfolded protein degradation pathway upregulated by MTX may not be restricted to the clearance of rhodopsin alone that could be applied to other misfolded protein associated blindness such as myocilin-associated primary open-angle glaucoma.

The molecular pathways regulating the protein homeostasis of G protein coupled receptors are not well understood. By screening both novel and pharmacologically active small molecule compounds, we were able to explore the chemical genetics and find out the most relevant molecular pathways that regulate rhodopsin homeostasis. Here, we identified 5 compounds that increased misfolded rhodopsin degradation on the HTS campaign of 68,979 small molecules: CL-001 and CL-007 are pan-cyclin-dependent kinase inhibitors; CL-005 is a stabilizer of HIF1α; CL-009 (MTX) is an inhibitor of folic acid metabolism; and only CL-002 is an unknown chemical without reported pharmacological activities. Although this study only focused on MTX for the mechanisms of action and in vivo effect, exploring potential roles of CKDs or other kinases, as well as modulators of HIF1α in mediating misfolded rhodopsin degradation are exciting future directions that may lead to a better understanding of membrane protein degradation.

MTX is water-soluble and it has been intravitreally administered as an off-tag treatment for inflammatory ocular diseases such as retina uveitis. Thus, the novel activity of MTX in the selective clearance of the P23H rhodopsin and its retinal protective effects in the $Rho^{P23H/+}$ mice make this drug with a therapeutic potential to be repurposed for the treatment of RHO-associated adRP.

MTX showed clear in vitro activity in the selective clearance of the P23H rhodopsin. Thus, it is counter-intuitive to observe an increase of rhodopsin level on the superior side of the $Rho^{P23H/+}$ mouse retinae after a single or multiple IVIs of MTX. Most of the rhodopsin immunostain is on the OS of MTX-treated $Rho^{P23H/+}$ mouse retinae (FIGS. 6 & 7), suggesting that the increased rhodopsin by MTX is adequately folded and transported to the targeted site. Considering the heterozygous background of the knock-in mice we tested here and that anti-rhodopsin antibody cannot distinguish P23H from WT rhodopsin, MTX's activity in increasing the folded rhodopsin level in the OS can be due to its selective clearance of P23H rhodopsin in vivo. Indeed, we saw an increased autophagy flux after an IVI of MTX in the $Rho^{P23H/+}$ mice, suggesting MTX may enhanced the misfolded rhodopsin degradation via inducing autophagy. To test this postulation, we determined the effect of MTX treatment on P23H rhodopsin level in the $Rho^{P23H/P23H}$ mice by an IVI of 25 pmol MTX at PND 15 followed by retinal immunoblotting at 24, 48 and 72 h after treatment. However, due to the low protein level of P23H rhodopsin in the $Rho^{P23H/P23H}$ mice (about 1/200 of rhodopsin compared to the $Rho^{+/+}$ retina), and high variations between individual animals, we did not see consistently and statistically significant difference of P23H rhodopsin by treatment of MTX, compared to PBS control (data not shown).

Spatial difference in retinal degeneration is known in the animal models of RP as well as in RP patients, but we are not clear why the inferior side of the retina degenerate faster than the superior side in RP. Interestingly, we observed repetitive asymmetric efficacy of MTX treatment to the $Rho^{P23H/+}$ retinae only on the superior side. This spatial difference in response to drug treatment has also been seen in IVI of neurotrophic factors to a rodent model of RP. Differential gene expression or light exposure between the superior and inferior retinae could contribute to the spatial susceptibility of MTX treatment.

The reason for MTX showed better retinal protection at 25 pmol than 100 pmol requires further investigation. One potential explanation could be the cytotoxicity of MTX at higher dose that may counter act with its protective effect by clearing out misfolded rhodopsin. Retinal damages were observed in rabbits with intravitreal injection of 1.76 μmol MTX (about 1 mM final concentration in vitreous, considering rabbit's vitreous cavity is about 1.5 mL). Mouse vitreous volume is about 5.3 μL, thus 100 pmol of MTX will yield an initial vitreous concentration of 18.9 μM, whereas 25 pmol of MTX administration gave about 4.7 μM vitreous concentration ($EC_{50}$ of MTX is about 3.3 μM in vitro). Even though we did not see obvious retinal degeneration caused by 100 pmol MTX, this result indicates that a thorough toxicity study of MTX is required for our future study. A transcriptome analysis by RNA-seq will also be an important future direction to understand the molecular pathways altered by MTX.

Caution should be taken with multiple IVIs, because our results demonstrate that four weekly IVIs of sterile PBS accelerated retinal degeneration in the $Rho^{P23H/+}$ mice compared to the untreated control. However, the four-dose MTX treated retinae showed increased photoreceptor numbers compared to PBS control, whereas one injection of MTX did not have this effect, suggesting one injection is not sufficient for long-term retinal protection in RP. A future development of optimized IVI intervals or a slow-release formula is required for long-term treatment with MTX to avoid adverse effects by IVIs.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

---

Having described the invention, we claim:

1. A method of promoting clearance of misfolded ocular proteins in a subject in need thereof, the method comprising: administering to the subject a therapeutically effective amount of a compound selected from:

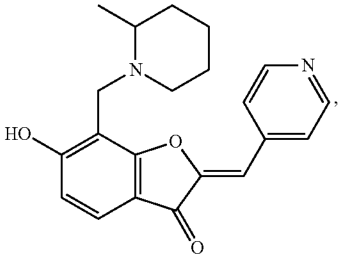,

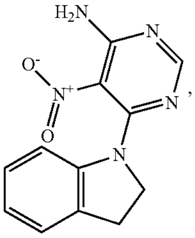,

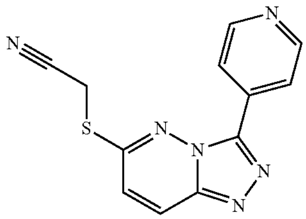,

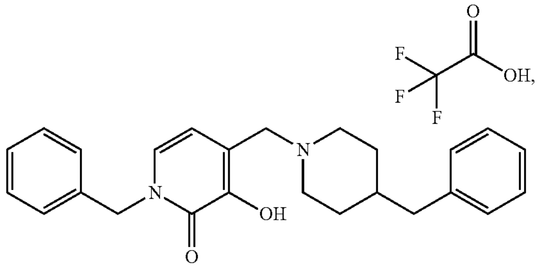,

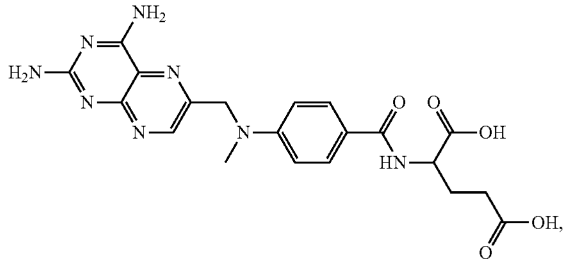, a pharmaceutically acceptable salt, tautomer, or solvate thereof, or combinations thereof, wherein the subject has a non syndromic autosomal dominant retinitis pigmentosa associated with or caused by the misfolded ocular protein.

2. The method of claim 1, wherein the compound is selected from:

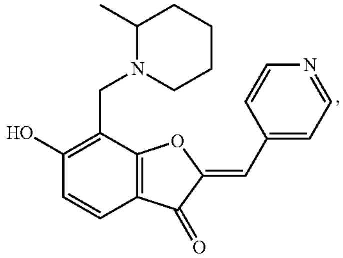,

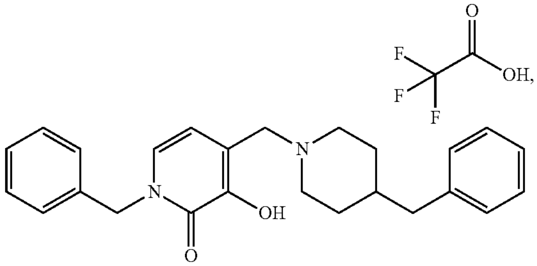,

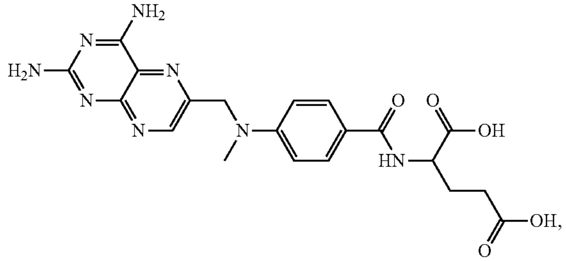, a pharmaceutically acceptable salt, tautomer, or solvate thereof, or combinations thereof.

3. The method of claim 1, wherein the compound is administered to the subject at early stage or mid stage of the non syndromic autosomal dominant retinitis pigmentosa.

4. The method claim 1, wherein the misfolded ocular protein is a misfolded opsin.

5. The method of claim 1, wherein the misfolded ocular protein is a misfolded opsin protein that comprises a mutation in its amino acid sequence.

6. The method of claim 5, wherein the mutation is at least one of P23H, C110Y, D190N, T17M, P347S, or P267L.

7. The method of claim 1, wherein the therapeutically effective amount is an amount effective to accelerate the degradation of the misfolded ocular protein, improve ocular protein homeostasis, improve or preserve visual function, inhibit photoreceptor cell death, and/or improve or preserve retinal structure.

8. The method of claim 7, wherein the improvement or preservation in visual function include an improvement or preservation of photopic electroretinogram (ERG) response.

9. The method of claim 7, the wherein the improvement or preservation in retinal structure is an improvement or preservation of outer nuclear layer (ONL) thickness.

10. The method of claim 1, wherein the compound is administered by at least one of topical administration, systemic administration, intravitreal injection, and intraocular delivery.

11. A method of treating an inherited ocular disorder associated with or caused by a misfolded ocular protein in a subject in need thereof, the method comprising: administering to the subject a therapeutically effective amount of a compound selected from:

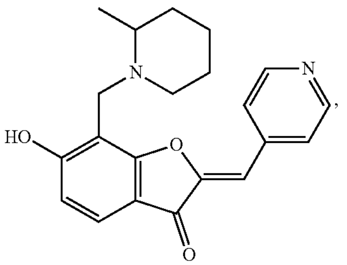

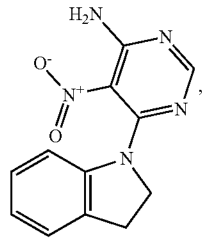

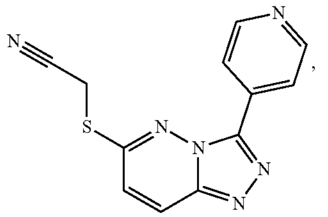

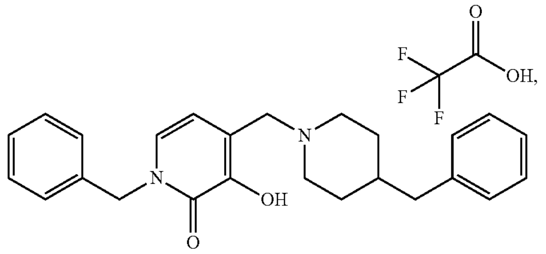

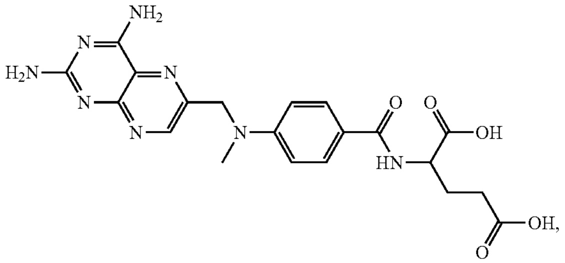

a pharmaceutically acceptable salt, tautomer, or solvate thereof, or combinations thereof, wherein the subject has a non syndromic autosomal dominant retinitis pigmentosa associated with or caused by the misfolded ocular protein.

12. The method of claim 11, wherein the compound is selected from:

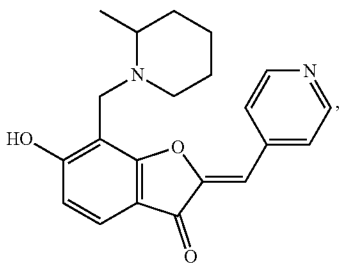

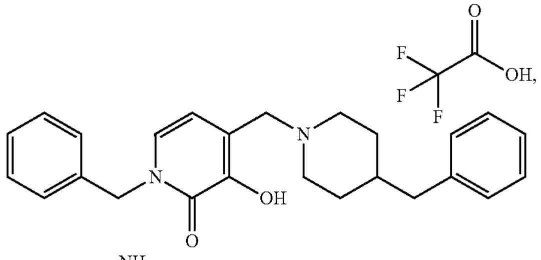

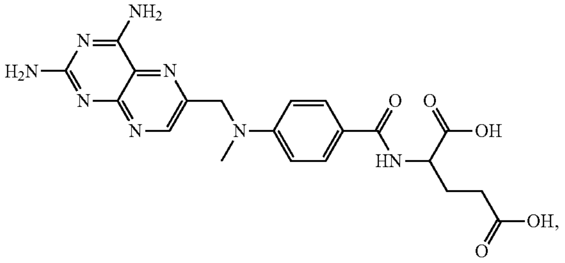

a pharmaceutically acceptable salt, tautomer, or solvate thereof, or combinations thereof.

13. The method of claim 11, wherein the compound is administered to the subject at early stage or mid stage of the non syndromic autosomal dominant retinitis pigmentosa.

14. The method of claim 11, wherein the misfolded ocular protein is a misfolded opsin.

15. The method of claim 11, wherein the misfolded ocular protein is a misfolded opsin protein that comprises a mutation in its amino acid sequence.

16. The method of claim 15, wherein the mutation is at least one of P23H, C110Y, D190N, T17M, P347S, or P267L.

17. The method of claim 11, wherein the therapeutically effective amount is an amount effective to accelerate the degradation of the misfolded ocular protein, improve ocular protein homeostasis, improve or preserve visual function, inhibit photoreceptor cell death, and/or improve or preserve retinal structure.

18. The method of claim 17, wherein the improvement or preservation in visual function include an improvement or preservation of photopic electroretinogram (ERG) response.

19. The method of claim 17, the wherein the improvement or preservation in retinal structure is an improvement or preservation of outer nuclear layer (ONL) thickness.

20. The method of claim 11, wherein the compound is administered by at least one of topical administration systemic administration, intravitreal injection, and intraocular delivery.

* * * * *

```
                          SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1

cccttctcca acgtcacagg                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2

tgaggaagtt gatggggaag c                                                 21

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3

accttctaca atgagctgcg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4

ctggatggct acgtacatgg                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5

ggtagcactg ttgggcatct                                                   20

<210> SEQ ID NO 6
<211> LENGTH: 14
```

-continued

```
<212> TYPE: DNA
<213> ORGANISM: Artificial Sequence
<220> FEATURE:
<223> OTHER INFORMATION: Synthetic Construct

<400> SEQUENCE: 6

acagagacaa gctc                                                    14
```